(12) United States Patent
Algers et al.

(10) Patent No.: US 12,409,077 B2
(45) Date of Patent: Sep. 9, 2025

(54) STRUCTURES COMPRISING PARTICLES AND PROCESSES FOR MAKING SAME

(71) Applicant: The Procter & Gamble Company, Cincinnati, OH (US)

(72) Inventors: John Daniel Algers, Montgomery, OH (US); Christopher Philip Bewick-Sonntag, Cincinnati, OH (US); John David Norcom, Cincinnati, OH (US); Michael Joseph Page, Cincinnati, OH (US); Christopher Michael Young, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/615,054

(22) Filed: Mar. 25, 2024

(65) Prior Publication Data

US 2024/0225913 A1    Jul. 11, 2024

Related U.S. Application Data

(63) Continuation of application No. 17/513,965, filed on Oct. 29, 2021, now abandoned.

(60) Provisional application No. 63/107,648, filed on Oct. 30, 2020.

(51) Int. Cl.
    *A61F 13/15*    (2006.01)
    *D01D 5/098*    (2006.01)

(52) U.S. Cl.
    CPC ..... *A61F 13/15658* (2013.01); *D01D 5/0985* (2013.01); *A61F 2013/15406* (2013.01)

(58) Field of Classification Search
    None
    See application file for complete search history.

(56) References Cited

U.S. PATENT DOCUMENTS

| | | | |
|---|---|---|---|
| 4,865,596 A * | 9/1989 | Weisman | A61L 15/18 604/368 |
| 5,858,292 A | 1/1999 | Dragoo et al. | |
| 6,086,950 A | 7/2000 | Masaki et al. | |
| 2002/0177376 A1 | 11/2002 | Welch et al. | |
| 2007/0045905 A1 * | 3/2007 | Venturino | D04H 1/43835 425/81.1 |
| 2009/0192481 A1 | 7/2009 | Dodge et al. | |
| 2016/0355950 A1 | 12/2016 | Young et al. | |
| 2017/0164810 A1 | 6/2017 | Wang et al. | |
| 2019/0284740 A1 | 9/2019 | Zampollo et al. | |
| 2022/0133548 A1 | 5/2022 | Algers et al. | |

FOREIGN PATENT DOCUMENTS

| | | |
|---|---|---|
| EP | 2679208 A1 | 1/2014 |
| WO | 0033783 A1 | 6/2000 |
| WO | 2018091453 A1 | 5/2018 |

OTHER PUBLICATIONS

Search Report and Written Opinion for PCT/US2021/072101 dated Feb. 25, 2022, 13 pages.
All Office Actions; U.S. Appl. No. 17/513,965, filed Oct. 29, 2021.

* cited by examiner

*Primary Examiner* — Alexander M Weddle
(74) *Attorney, Agent, or Firm* — James E. Oehlenschlager

(57) ABSTRACT

Structures, for example fibrous structures, such as absorbent material, for example absorbent core material including particles, for example super absorbent polymer particles (SAP particles), and processes for making same are provided.

17 Claims, 25 Drawing Sheets

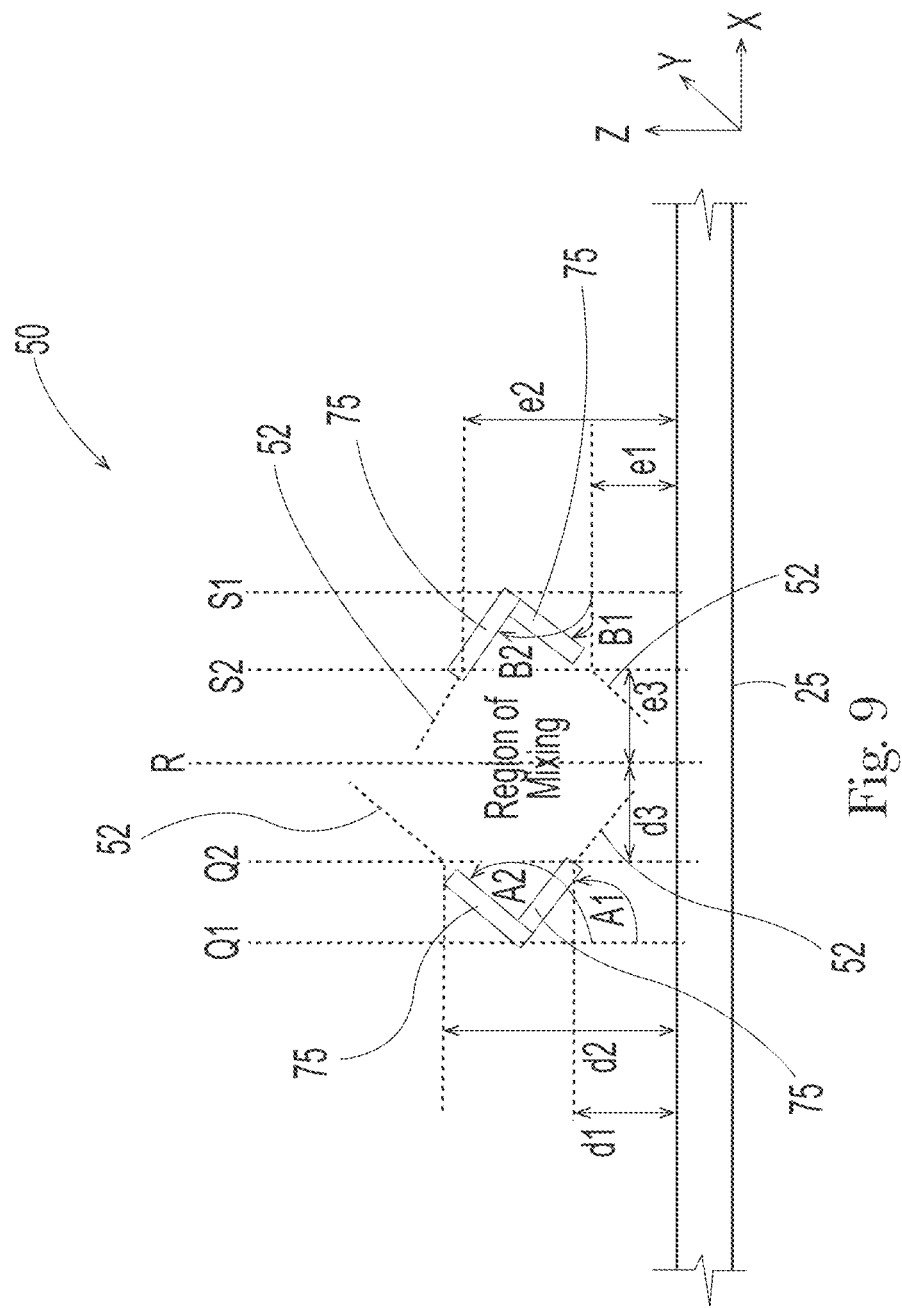

STRUCTURES COMPRISING PARTICLES AND PROCESSES FOR MAKING SAME

FIELD OF THE INVENTION

The present invention relates to structures, for example fibrous structures, such as absorbent material, for example absorbent core material comprising particles, and more particularly to fibrous structures comprising particles, for example super absorbent polymer particles (SAP particles), and processes for making same.

BACKGROUND OF THE INVENTION

For many hygienic applications, it is beneficial to integrate particles, such as SAP particles, of different size, shape, density, Stokes Number, and/or mass into a single structure, for example a fibrous structure, such as an absorbent material, for example an absorbent core material, to meet all desired performance requirements. These desired performance requirements could include a combination of mechanical properties such as softness and/or flexibility, and fluid handling properties for protection against leaks and to keep skin dry when in contact with the structure and/or products containing the structure.

In addition to the incorporation of particles into the structures, formulators have incorporated non-particle solid additives, such as fibers, for example pulp fibers.

Known non-limiting examples of solid additives (particles and/or non-particles), for inclusion in the structure, for example fibrous structure, such as absorbent core material, include fibers, such as: 1) pulp fibers for providing absorbency, flexibility and/or softness to the structure, for example fibrous structure, such as an absorbent core material; 2) SAP particles to provide sufficient capacity for liquid retention (e.g. urine or menses) to the structure, for example fibrous structure, such as an absorbent core material; 3) perfume particles to provide scent generation; 4) odor controlling particles for controlling odors; 5) abrasive particles for providing abrasive properties to the structure, for example fibrous structure, such as an absorbent core material; and 6) other inorganic and/or organic particles. However, known processes of integrating solid additives, such as fibers and/or particles of different size, shape, and density and/or solid additives, such as fibers and/or particles that exhibit different Stokes Numbers, for example pulp fibers and SAP particles, into single structures, for example fibrous structures, such as an absorbent core material, have been less than successful due to negatives associated with the resulting structures. It is believed that the problems associated with using known processes of integrating such solid additives into such structures relate, at least partially, to the use of a mixed solid additive stream, for example an air stream comprising mixed solid additives, for example fibers, such as pulp fibers, and particles, such as SAP particles, in the process for making the structure. Such a mixed solid additive stream containing a mixture of solid additives of different size, shape, and/or density and/or different Stokes Numbers results in different trajectories of the different solid additives based on their size, shape, density and/or Stokes Number and results in unacceptable formation of the structure, for example fibrous structure, such as an absorbent core material because the fibrous structure may exhibit a higher density, for example greater than 0.2 g/cm$^3$ and/or the different solid additives may not be sufficiently integrated, distributed, and/or be captured within the structure.

Prior Art FIG. 1A illustrates an example of a known process for integrating solid additives; namely, particles and non-particle solid additives, for example fibers, into a single structure, for example a fibrous structure, such as an absorbent material, for example an absorbent core material. As shown in Prior Art FIG. 1A, the process 10, oftentimes referred to as a coform process and/or a spinform process, comprises two meltblown polymer filament streams 12 each stream formed by extruding a molten thermoplastic material into converging high velocity gas via knife edge dies 14 and a mixed solid additive stream 16 comprising a mixture of fibers 18, for example pulp fibers, and particles 20, for example SAP particles, that impinge the two meltblown filament streams 12 where the two meltblown filament streams 12 converge. The mixed solid additive stream 16 is injected into the two meltblown filament streams 12 at an impingement zone 22 wherein the two meltblown filament streams 12 converge. The fibers 18 and particles 20 exhibit different size, shape, and/or density and different Stokes Numbers. The two meltblown filament streams 12 each comprise a plurality of meltblown filaments 24. The two meltblown filament streams 12 and the mixed solid additive stream 16 are all open to ambient air and pressure. In other words, the streams 12 and 16 are not under a controlled environment and/or closed environment and/or enclosed in an enclosure, which can create negatives with the process, both formation of the structure and hygiene of the process.

Due, at least in part, to the difference in the Stokes Numbers for the fibers 18, for example wood pulp fibers that exhibit a relatively low Stokes Number, and the particles 20, for example SAP particles that exhibit relatively high Stokes Number, the air stream conveying and delivering the mixed solid additive stream 16 to the impingement zone 22 is unable to prevent at least a portion of the particles 20 from ending up on the top T and bottom B of the structure 26, for example fibrous structure, such as absorbent material, as shown in Prior Art FIG. 1B. Since the particles 20 exhibit a higher, for example significantly higher, Stokes Number than the fibers 18, the particles 20 are prone to random trajectories and thus is a non-controlled distribution of the particles that result in the particles 20 being present at higher concentrations near the upstream and downstream edges of the mixed solid additive stream 16 unlike the fibers 18 which tend to be more uniformly dispersed or more concentrated in the inner portion of the mixed solid additive stream 16. Having the particles 20, for example SAP particles, concentrated at the top T and bottom B of the structure 26 raises safety and hygiene concerns due to the loose particles 20 readily becoming separated from the structure 26 since they are not entrained sufficiently within the plurality of interentangled filaments 24 of the structure 26. Further, this known prior art process results in structures, for example fibrous structures, such as absorbent material, for example absorbent core material that exhibit a random arrangement of the particles within and/or on the resulting structure.

The problems described above with respect to the prior art process 10 as shown in Prior Art FIG. 1A and the resulting structure 26 as shown in Prior Art FIGS. 1B and 1C can be addressed by modifying the process conditions to ensure that a higher concentration of meltblown filaments 24 are present at one or more of the top T and bottom B of the structure 26 to sufficiently retain the particles 20 within the structure 26 without negatively impacting the other desired properties of the structure 26. However, these modifications fail to address the non-controlled distribution of the particles 20 and the random arrangement of the particles 20 in the composite fluid stream and ultimately the resulting structure 26. Further, higher concentrations of meltblown filaments 24 in the top T and/or bottom B of the structure 26 may lessen the integrity and/or mixing of the particles and filaments in the overall the structure 26 by having lower concentrations of meltblown filaments in other parts of the structure 26 and/or prevent fibers 18 and/or particles 20 from becoming dislodged from the structure 26 during material handling of the structure 26, such as winding, slitting, unwinding, and converting into a finished absorbent material, such as a finished absorbent core material.

In addition, if the concentration (meaning amount and/or level, for example mass per unit volume and/or % by weight) of meltblown filaments 24 is too high on one or both sides (top T and/or bottom B), then the meltblown filaments 24 may create a fluid barrier at the structure's surface or surfaces. Such a fluid barrier will increase fluid acquisition times and/or reduce the performance, for example absorbency performance, of the structure 26 by inhibiting the structure's ability to absorb fluids.

In light of the foregoing, the Prior Art FIG. 1A process 10 and its resulting structure 26 as shown in Prior Art FIG. 1B exhibit negatives that need to be solved.

Likewise, the process 10 as shown in Prior Art FIG. 2A also exhibits negatives that need to be solved. The process 10 as shown in Prior Art FIG. 2A is another example of a known process for integrating solid additives into a single structure, for example a fibrous structure, such as an absorbent material, for example an absorbent core material. Unlike the known process described above and in Prior Art FIG. 1A, the process 10 shown in Prior Art FIG. 2A is performed under a controlled environment and/or closed environment and/or enclosed or substantially enclosed in an enclosure 28. As shown in Prior Art FIG. 2A, the process 10, comprises a single meltblown polymer filament stream 12 formed by extruding a molten thermoplastic material via a filament source 30, in this case a multi-row capillary die and at least one mixed solid additive stream 16 comprising a mixture of fibers 18, for example pulp fibers, sourced from a fiber source (not shown) and particles 20, for example SAP particles, sourced from a particle source (not shown). The process 10 of Prior Art FIG. 2A may comprise one or more solid additive streams 32, for example a fiber stream as shown in Prior Art FIG. 2A and/or mixed solid additive streams 16, for example fibers 18 and particles 20, that are added to the single meltblown polymer filament stream 30 comprising a plurality of meltblown filaments 24. The fibers 18 and particles 20 exhibit different size, shape, and/or density and different Stokes Numbers. As a result, the fibers 18 and particles 20 exhibit differences in their inertia also. Therefore, in order to achieve good mixing of the fibers 18 and particles 20, one would need a relatively straight path between the point of mixing and the collection device. In the case of the process 10 of Prior Art FIG. 2A, the path traveled by the mixed solid additive stream 16 is not relatively straight due to one or more bends in the path. Such bends result in separation between with fibers 18 and the particles 20 due to different Stokes Numbers, which leads to poor mixing of the fibers 18 and particles 20 within the mixed solid additive stream 16 and is considered a non-controlled distribution of the particles 20, which results in a random arrangement of the particles within and/or on the resulting structure 26.

In addition to the poor mixing of the fibers 18 and particles 20 by the process 10 of Prior Art FIG. 2A, the resulting structure 26 from the process 10 of Prior Art FIG. 2A as shown in Prior Art FIGS. 2B-2D contains substantially all of the particles 20 on one side, for example the top T side or portion of the resulting structure 26 as shown in Prior Art FIGS. 2B and 2C or the bottom B side or portion of the resulting structure 26 as shown in Prior Art FIG. 2D.

Even though individual SAP particles may follow slightly different trajectories depending on their respective individual sizes, shapes, densities, and Stokes Numbers, small and large SAP particles all still separate from the fibers during formation of the structure thus resulting in negatives in the structure.

In light of the foregoing, the Prior Art FIG. 2A process 10 and its resulting structure 26 as shown in Prior Art FIG. 2B exhibit negatives that need to be solved.

Commercially available SAP particles are typically manufactured in a way that leads to a large distribution in particle size. Typical particle sizes are between 30 µm to 800 µm. Having both large and small particles in the SAP particles can be advantageous. The benefits of smaller particle is typically faster rate of absorption due to a higher surface-to-volume ratio. However, they tend to have a smaller capacity (liquid stored per gram of SAP material) and also have a tendency to create gel blocking. Gel blocking is detrimental to absorbent core material as it reduces the permeability and blocks passage ways for fluid to be spread within the absorbent structure to be blocked resulting in poor absorption and increased risk of fluid over flowing an article or wet sensation while wearing the product.

Conversely, the benefit of larger SAP particles is that they tend to have a higher capacity per gram and so are more cost efficient to store a certain amount of liquid and they are also less likely to gel block. However, rate of absorption tends to be lower.

The difference in absorption performance between small and large particles has resulted in the SAP particle size distribution being a key factor for fluid handling performance of absorbent articles. (reference typical optimization of fluid handling performance with g SAP per pad, and also z-direction gradient of concentration. Using only absolute levels of SAP particles, and concentration in z-direction does not solve the inherent trade-off between small and large particles)

To get the best performance out of a given particle size distribution, i.e. obtain the maximum absorption speed advantages and gram per gram capacity while preventing gel blocking, it would be highly advantageous to separate the small particles (for speed of acquisition but prone to gel blocking) from the large particles.

In particular it would be highly advantageous to enable a supply of SAP particles with a wide size distribution, and then introduce them into a filament matrix such that the smaller particles preferentially locate towards one side, for example the bottom, where gel blocking is less of a concern, and preferentially locate larger particles towards the opposite side, for example the top, where permeability is important and significant presence of small SAP particles could be detrimental to permeability and performance. This is particularly true in product applications where the fluid enters in several insults or over a longer time period where gel blocking of one insult can cause the next insult to not absorb well into the structure or in the case of a menstrual product if fluid is preferentially absorbed at the top, closer to the body, leaving a wet wearing sensation. The effect of particle size distribution would be separate from the simple effects of controlling z-direction gradient of SAP concentration, i.e. structures that have a more uniform particle size distribution at any given plane in the z-direction of the substrate.

Fibrous structures comprising SAP particles are known in the art. For example, prior art coform processes utilizing converging air, knife-edge die technology for making such fibrous structures are known in the art. However, the problem associated with such known fibrous structures and prior art processes is that the random distribution of the SAP particles throughout such known fibrous structures, especially in the z-direction, for example throughout the thickness of such known fibrous structures, is substantially uniform with respect to the SAP particle average particle size. In other words, large SAP particles and small SAP particles are mixed and distributed randomly and substantially uniformly throughout such known fibrous structures, especially in the z-direction, for example throughout the thickness of such known fibrous structures. Such a random and substantially uniform distribution throughout the known fibrous structures results in negatives associated with the absorbent performance of such known fibrous structures. In other words, the presence of smaller size SAP particles near one side of the fibrous structure; namely, the side of the fibrous structure that is intended to receive the initial insult of liquid, such as urine and/or menses when the fibrous structure is utilized as an absorbent core, results in the smaller size SAP particles absorbing the liquid and creating gel blocking, which prevents at least a portion if not a substantial amount of the liquid from penetrating further into the thickness of the fibrous structure for the absorbent core.

Formulators have attempted to correct these negatives associated with such known fibrous structures by starving the side of the known fibrous structures of SAP particles such that there are less SAP particles (large and small particle size) near the side of the fibrous structure that receives the initial insult and thus mitigates the gel blocking problem. However, the SAP particles throughout the thickness of the fibrous structure continues to contain a random and substantially uniform mixture of large and small particle size SAP particles, there is no gradient of particle sizes of SAP particles within the thickness of the known fibrous structures, which still results in less than superior absorbent performance of the fibrous structures when utilized as absorbent cores. A further problem with removal of SAP particles entirely from the body facing side surface is the benefits in dryness that SAP particles can deliver while wearing a product when used in moderation close to the body to article interface.

Another problem seen in prior art processes as discussed above is the problem with the integrating mixed solid additives, such as two or more different (by size, shape, density, and/or Stokes Number) solid additives, for example fibers, such as pulp fibers, and particles, such as SAP particles, into a structure, such as a fibrous structure, for example an absorbent material, such as an absorbent core material. Such known processes fail to effectively control the distribution of the solid additives, for example high Stokes Number solid additives, in particular the particles, within the resulting structure and/or fail to effectively control the concentration of such solid additives throughout the resulting structure such that the particles are arranged in the resulting structure in a non-random arrangement.

Accordingly, there is a need for a process for integrating particles, such as SAP particles, into a structure, such as a fibrous structure, for example an absorbent material, such as an absorbent core material, that provides a controlled distribution of the particles resulting in a structure comprising a non-random arrangement of the particles within the structure and/or provides non-random arrangement of concentrations of such particles throughout the resulting structure as well as resulting structures that overcome the negatives associated with known fibrous structures comprising particles.

SUMMARY OF THE INVENTION

The present invention fulfills the needs described above by providing a novel process for integrating a plurality of particles into a plurality of fibrous elements, for example filaments and/or fibers, for example a stream of a plurality of filaments, such as a fluid stream comprising a plurality of fibrous elements, for example filaments, wherein a stream of a plurality of particles, for example a fluid stream comprising a plurality of particles, are mixed and/or added to the fluid stream comprising the plurality of fibrous elements, for example filaments, by a controlled particle distribution process creating a non-random arrangement of the plurality of particles in the resulting composite fluid stream comprising the plurality particles and the plurality of fibrous elements, for example the plurality of filaments. Further, the resulting structure, for example a fibrous structure, such as an absorbent material, for example an absorbent core material formed upon collecting the composite fluid stream onto a collection device also exhibits a non-random arrangement of the plurality of the particles in the resulting structure.

One solution to the problem identified above is a novel process for introducing, such as mixing and/or adding, particles, for example a fluid stream comprising a plurality of particles (a particle stream), into a fluid stream comprising a plurality of fibrous elements, for example a plurality of filaments, (a fibrous element stream and/or filament stream) in a controlled distribution, for example by controlling the angle and/or velocity at which the plurality of particles from the fluid stream comprising the plurality of particles are introduced (mixed and/or added) into the filament stream such that a composite fluid stream comprising a non-random arrangement of the particles in the filament stream results. If the composite fluid stream is collected on a collection device, a resulting structure, for example a fibrous structure, such as an absorbent material, for example an absorbent core material comprising a non-random arrangement of the particles in the structure is formed. In one example, the novel process makes a fibrous structure comprising particles, such as SAP particles, that are present within the fibrous structure, especially the z-direction of the fibrous structure, in other words the thickness of the fibrous structure, such that a gradient, for example a continuous gradient of the particle sizes of the SAP particles is present within at least a portion of the thickness of the fibrous structure. For example, the fibrous structure comprises SAP particles present within the thickness of the fibrous structure such that a higher concentration (meaning amount and/or level, for example mass per unit volume and/or % by weight) of larger size SAP particles relative to smaller size SAP particles and/or less total smaller size SAP particles, are present near the side of the fibrous structure that will receive an initial insult of liquid, for example urine and/or menses, when the fibrous structure is used as an absorbent core in an absorbent article. By having this arrangement of sizes of SAP particles, gel blocking is mitigated and/or inhibited due to the relatively lesser amount and/or actual lesser amount of smaller size SAP particles present in that side of the fibrous structure.

In one example of the present invention, a process for forming a composite fluid stream, the process comprising the step of mixing, for example commingling, such as coforming, a first fluid stream comprising a plurality of fibrous elements, for example filaments and/or fibers, such as filaments, for example water-insoluble fibrous elements, such as water-insoluble filaments, with a second fluid stream comprising a plurality of first particles, for example SAP particles, such that a composite fluid stream (comprising the fibrous elements and first particles) exhibiting a non-random arrangement of the plurality of first particles in the composite fluid stream is formed, and optionally or alternatively such that a composite fluid stream (comprising the fibrous elements and first particles) exhibiting a non-random arrangement of the plurality of first particles in the composite fluid stream is formed substantially simultaneous with collecting the composite fluid stream on a collection device, and optionally, the step of collecting the composite fluid stream on a collection device, which may comprise a nonwoven web material, such as a pre-existing nonwoven web material, for example a top sheet, such as a secondary topsheet, such that a fibrous structure exhibiting a non-random arrangement of the plurality of first particles in the fibrous structure is formed, is provided.

In another example of the present invention, a process for making a fibrous structure, the process comprising the steps of:
  a. providing a plurality of filaments;
  b. providing a plurality of particles wherein the particles exhibit a broad range of particle size distribution, for example wherein the plurality of particles exhibit an average particle size distribution of about 300 μm and/or wherein the plurality of particles exhibit a range of particle sizes from about 45 μm to about 710 μm and/or greater than 250 μm and/or greater than 400 μm and/or greater than 500 μm and/or greater than 600 μm and/or greater than 700 μm (for example the plurality of particles may comprise particles having a particle size of about 700 μm and particles having a particle size of about 45 μm); and
  c. commingling the plurality of filaments with the plurality of particles;
  d. collecting the commingled plurality of filaments and plurality of particles on a collection device to form a fibrous structure, such that the plurality of particles are dispersed in the fibrous structure, in a non-random arrangement (for example based on the particle's size, shape, density, mass, Stokes Number), is provided.

In another example of the present invention, a structure, for example a fibrous structure, that is made by the process of the present invention, is provided.

In another example of the present invention, a structure, for example fibrous structure, comprising a plurality of fibrous elements, for example filaments and/or fibers, such as filaments, and a plurality of first particles, for example SAP particles, wherein the plurality of first particles are arranged in the structure, for example fibrous structure, in a non-random arrangement, is provided.

In another example of the present invention, a fibrous structure comprising a plurality of filaments and a plurality of particles wherein the plurality of particles are present in the fibrous structure in a non-random arrangement (for example based on the particles' size, shape, density, mass, Stokes Number), is provided.

In another example of the present invention, a process according to any of the described processes of the present invention wherein the diameters, for example average diameters of the filaments as measured according to the Average Diameter Test Method described herein vary in the fibrous structure, for example vary by layers and/or by particle type inclusion and/or by beams laying down the filaments, with or without particles included.

In another example of the present invention, a process for making a particle-containing fibrous structure, the process comprising the steps of:
  a. adding a plurality of first particles to a first stream of first filaments having a first average diameter to form a first composite stream;
  b. collecting the first composite stream onto a collection device to form a first layer of the fibrous structure;
  c. adding a plurality of second particles to a second stream of second filaments having a second average diameter different from the first average diameter to form a second composite stream;
  d. collecting the second composite stream directly onto the first layer of the fibrous structure to form a layered fibrous structure comprising the first layer and a second layer formed from the second composite stream, is provided.

In yet another example of the present invention, the fibrous structures of the present invention exhibit a total fibrous structure (fibrous elements and particles) density of less than 0.2 g/cm$^3$ and/or less than 0.15 g/cm$^3$ and/or less than 0.1 g/cm$^3$.

Accordingly, the present invention provides a novel process for making a composite fluid stream comprising fibrous elements, for example filaments, and particles, for example SAP particles, and a novel structure, for example a fibrous structure, such as an absorbent material, for example an absorbent core material, made from such composite fluid stream and/or process.

BRIEF DESCRIPTION OF THE DRAWINGS

FIG. 9 is a schematic representation of an example of a process according to the present invention;

FIG. 14C is a schematic representation of the fibrous structure made from Process Example 1a;

DETAILED DESCRIPTION OF THE INVENTION

Definitions

Figure 1A:
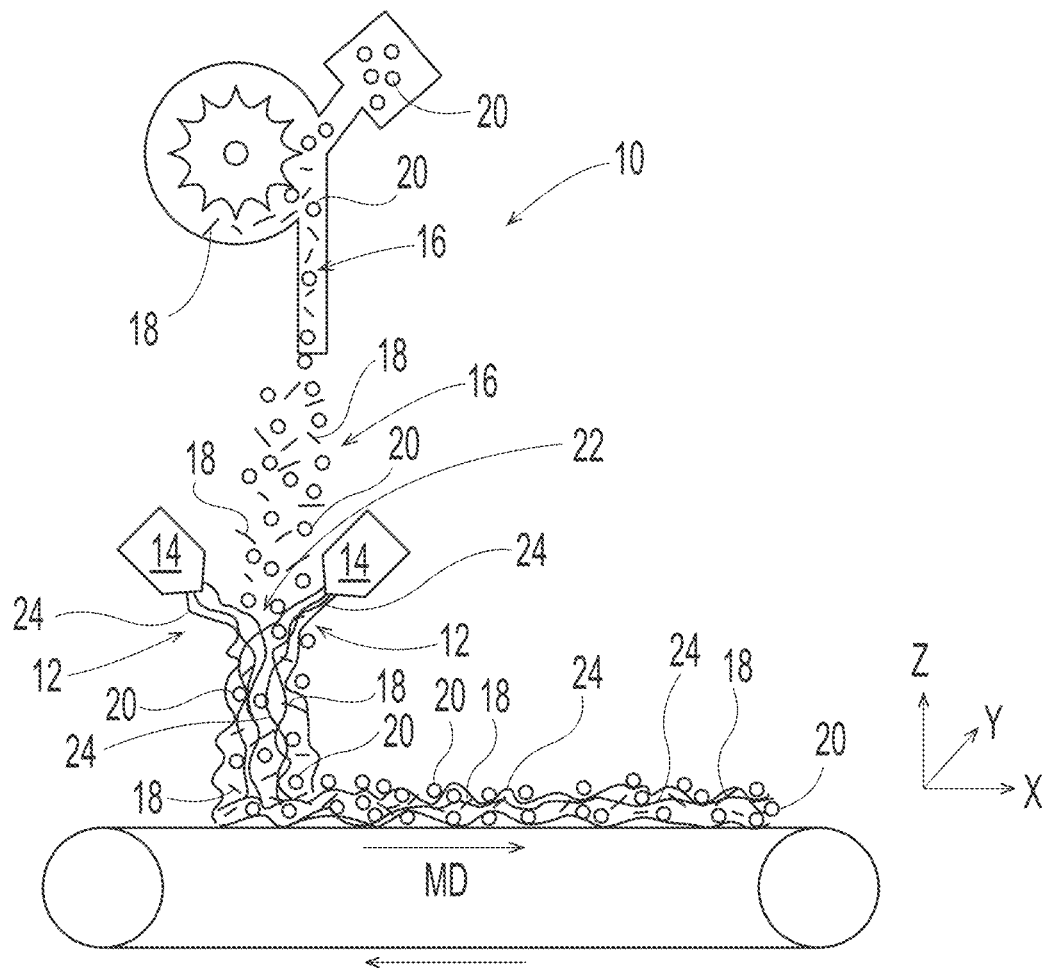
FIG. 1A is a schematic representation of an example of a prior art process for combining particles and fibrous elements.
Figure 1B:
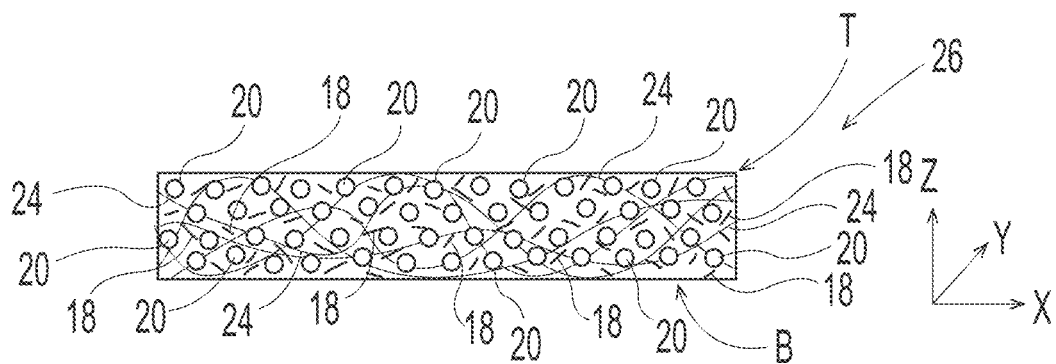
FIG. 1B is a schematic representation of an example of a prior art fibrous structure that can be produced by the prior art process of FIG. 1A.
Figure 1C:
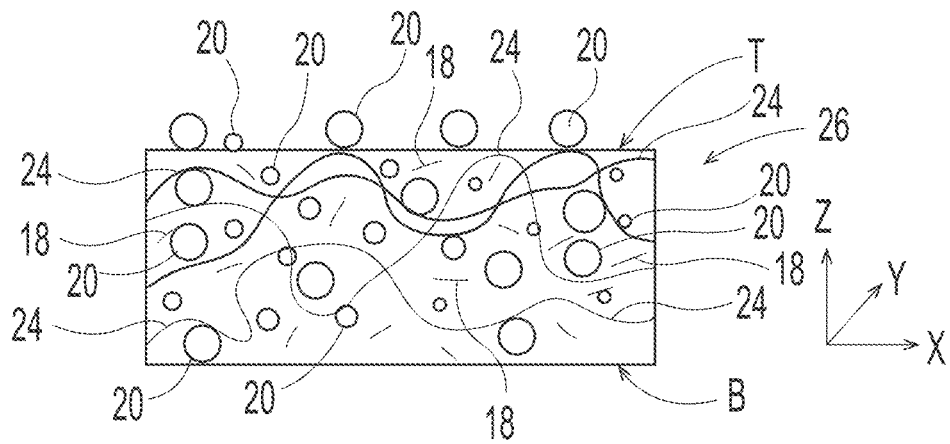
FIG. 1C is a schematic representation of another example of a prior art fibrous structure that can be produced by the prior art process of FIG. 1A.
Figure 2A:
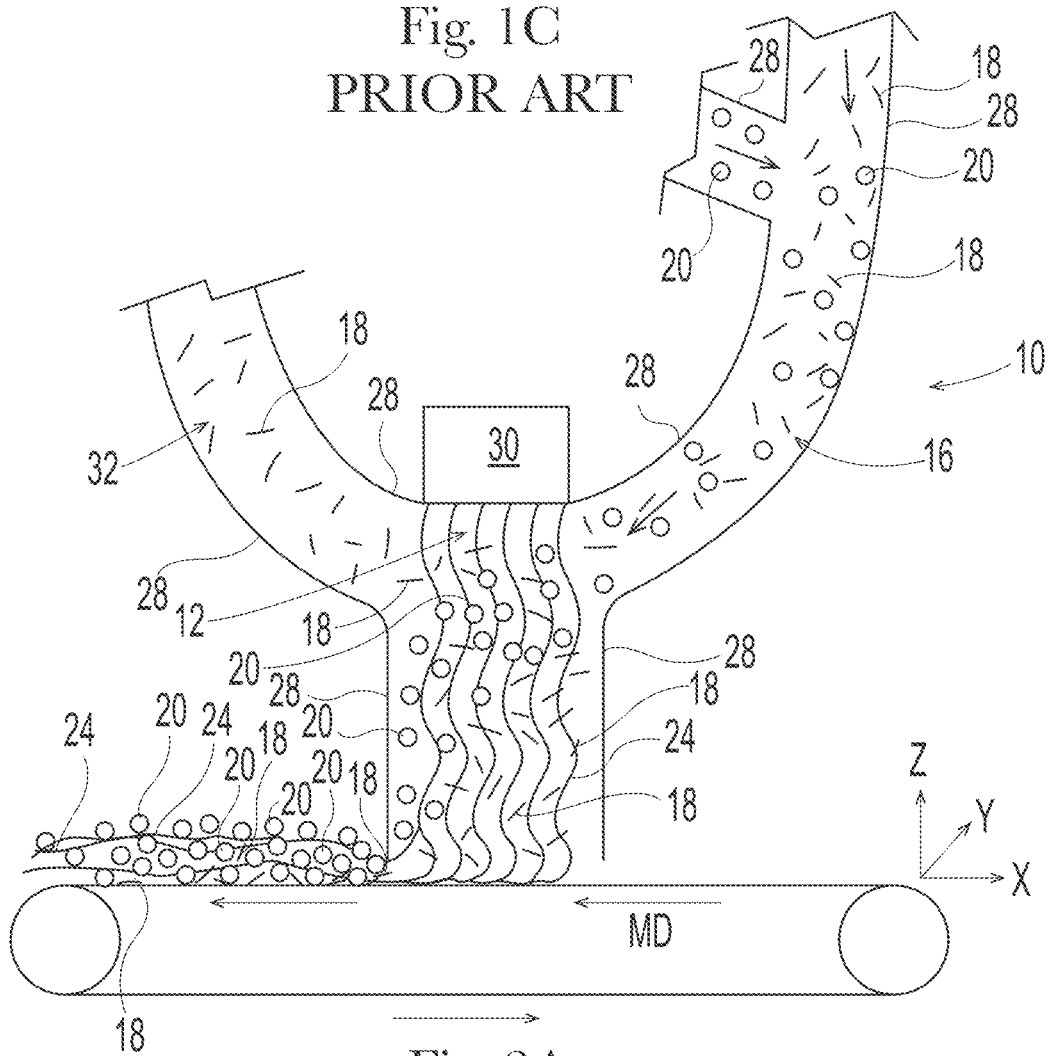
FIG. 2A is a schematic representation of an example of another prior art process for combining particles and fibrous elements.
Figure 2B:
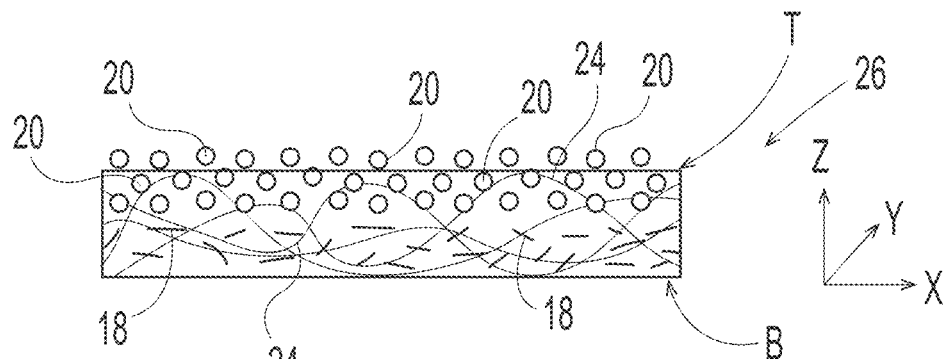
FIG. 2B is a schematic representation of an example of a prior art fibrous structure that can be produced by the prior art process of FIG. 2A.
Figure 2C:
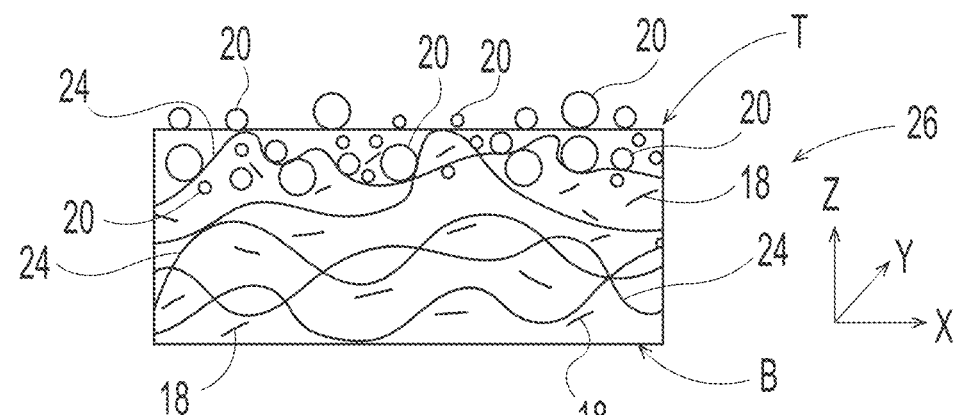
FIG. 2C is a schematic representation of another example of a prior art fibrous structure that can be produced by the prior art process of FIG. 2A.
Figure 2D:
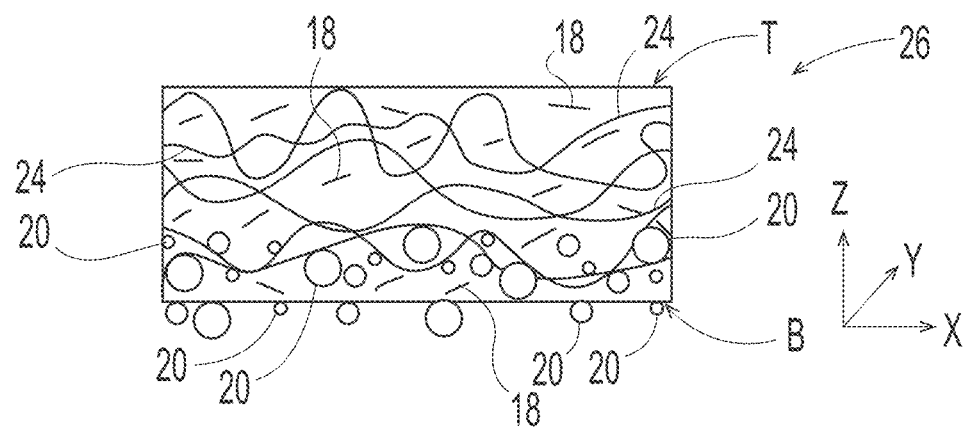
FIG. 2D is a schematic representation of another example of a prior art fibrous structure that can be produced by the prior art process of FIG. 2A.

"Non-random arrangement" as used herein with respect to 1) the presence of particles in a composite fluid stream, for example the presence of particles in a composite fluid stream comprising a plurality of fibrous elements, for example filaments and/or fibers, such as filaments, and a plurality of the particles, means that a) the particles are present in the composite fluid stream at different machine direction thickness locations in the composite fluid stream based on a particle characteristic selected from the group consisting of: size, shape, mass, density, Stokes Number, and mixtures thereof, for example size and/or Stokes Number; and/or b) the particles are present in a machine direction gradient in the composite fluid stream based on a particle characteristic selected from the group consisting of: size, shape, mass, density, Stokes Number, and mixtures thereof; and/or c) the particles are present in the composite fluid stream at one or more localized regions within the composition fluid stream's machine direction thickness (less than the composite fluid stream's entire or substantially entire machine direction thickness); and/or d) the particles are present in the composite fluid stream at different concentrations (amount and/or level, for example % by weight, for example based on composition of particle) in the composite fluid stream's machine direction thickness; and/or e) the particles are present in the composition fluid stream at one or more localized regions of the composite fluid stream's cross machine direction dimension (less than the composite fluid stream's entire or substantially entire cross machine direction dimension, for example the particles are present in one or more machine direction stripes); and/or 2) the presence of particles in a structure, for example a fibrous structure, such as an absorbent material, for example an absorbent core material, comprising a plurality of fibrous elements, for example filaments and/or fibers, such as filaments, and a plurality of the particles, means that a) the particles are present in the fibrous structure at different z-direction thickness locations in the fibrous structure based on a particle characteristic selected from the group consisting of: size, shape, mass, density, Stokes Number, and mixtures thereof, for example size and/or Stokes Number; and/or b) the particles are present in a z-direction gradient in the fibrous structure based on a particle characteristic selected from the group consisting of: size, shape, mass, density, Stokes Number, and mixtures thereof; and/or c) the particles are present in the fibrous structure at one or more localized regions within the fibrous structure's z-direction thickness (less than the fibrous structure's entire or substantially entire z-direction thickness); and/or d) the particles are present in the fibrous structure at different concentrations (amount and/or level, for example % by weight, for example based on composition of particle) in the fibrous structure's z-direction thickness; and/or e) the particles are present in the fibrous structure at one or more localized regions of the fibrous structure's cross machine direction dimension (less than the fibrous structure's entire or substantially entire cross machine direction dimension, for example the particles are present in one or more machine direction stripes; and/or f) the particles are present in the structure, for example a fibrous structure, in i) a z-direction distribution such that the particles within the structure exhibit a z-direction gradient based on the physical characteristics of the particles, such as size, shape, mass and/or Stokes Number; 2) a z-direction distribution and/or xy-direction distribution such that the particles within the structure, for example fibrous structure, are present within the structure, for example fibrous structure, at different concentration levels, for example in the z-direction and/or xy-direction; or 3) xy-direction distribution such that the particles are present in discrete zones within the structure, such zones may further exhibit z-direction distribution of particles within a zone such that the particles exhibit a z-direction gradient based on the physical characteristics of the particles, such as size, shape, mass and/or Stokes Number and/or such zones may further exhibit different concentration levels of particles within different zones.

"Fibrous structure" as used herein means a structure that comprises a plurality of filaments, for example a plurality of filaments and/or a plurality of fibers. In addition to the filaments, the fibrous structures may comprise other materials such as particles, for example SAP particles, and/or pulp fibers. In one example, a fibrous structure according to the present invention means an orderly arrangement of filaments and particles within a structure in order to perform a function, for example absorb liquids. In another example, a fibrous structure according to the present invention is a nonwoven. In one example, the fibrous structures of the present invention may comprise coform fibrous structures, meltblown fibrous structures, and spunbond fibrous structures so long as they contain particles. In one example, the fibrous structure is a non-hydroentangled fibrous structure. In another example, the fibrous structure is a non-carded fibrous structure.

In another example of the present invention, a fibrous structure comprises a plurality of inter-entangled fibrous elements, for example inter-entangled filaments, and particles dispersed between the inter-entangled filaments.

The fibrous structures of the present invention may be homogeneous, non-homogeneous, or layered. If layered, the fibrous structures may comprise at least two and/or at least three and/or at least four and/or at least five layers.

The fibrous structures of the present invention may exhibit basis weights of from about 75 gsm to about 2000 gsm and/or from about 75 gsm to about 1500 gsm and/or from about 100 to about 1000 gsm. In one example, the fibrous elements, for example filaments, are present in the fibrous structures of the present invention at a basis weight of from about 20 gsm to about 1000 gsm and/or from about 40 gsm to about 800 gsm and/or from about 75 gsm to about 700 gsm and/or from about 100 gsm to about 600 gsm. In one example, the particles, for example SAP particles, are present in the fibrous structures of the present invention at a basis weight of from about 10 gsm to about 1000 gsm and/or from about 20 gsm to about 700 gsm and/or from about 40 gsm to about 600 gsm and/or from about 100 gsm to about 600 gsm and/or from about 150 gsm to about 400 gsm.

"Multi-fibrous element fibrous structure" as used herein means a fibrous structure that comprises filaments and fibers, for example a coform fibrous structure is a multi-fibrous element fibrous structure.

"Mono-fibrous element fibrous structure" as used herein means a fibrous structure that comprises only fibers or filaments, for example a meltblown fibrous structure, such as a scrim, respectively, not a mixture of fibers and filaments.

"Coform fibrous structure" as used herein means that the fibrous structure comprises a mixture of filaments, such as filaments, for example meltblown filaments, such as thermoplastic filaments, for example polypropylene filaments, and SAP particles, and optionally pulp fibers, for example wood pulp fibers. The filaments, for example filaments and the SAP particles, and optionally the pulp fibers are commingled together to form the coform fibrous structure. The coform fibrous structure may be associated with one or more meltblown fibrous structures and/or spunbond fibrous structures, which form a scrim (or scrim layer that is deposited, for example spun directly onto a surface of a fibrous structure of the present invention that is being concurrently formed or that is already pre-formed and/or spun directly onto a collection device prior to a fibrous structure of the present invention being formed (via spinning) directly on a surface of the scrim layer (in one example the scrim may be present at a basis weight of greater than 0.5 gsm to about 5 gsm and/or from about 1 gsm to about 4 gsm and/or from about 1 gsm to about 3 gsm and/or from about 1.5 gsm to about 2.5 gsm), such as on one or more surfaces of the coform fibrous structure.

The coform fibrous structure of the present invention may be made via a suitable coforming process.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol filaments and/or polyvinyl alcohol derivative filaments, and thermoplastic polymer filaments, such as polyesters, for example polyethylene terephthalate (PET), nylons, polyolefins such as polypropylene filaments, polyethylene filaments, and polypropylene and polyethylene copolymer filaments, and biodegradable or compostable thermoplastic fibers such as polylactic acid filaments, polyhydroxyalkanoate filaments, polyesteramide filaments, and polycaprolactone filaments. The filaments may be monocomponent or multicomponent, such as bicomponent filaments. In one example, the filaments are monocomponent filaments.

The filaments may be made via spinning, for example via meltblowing and/or spunbonding, from a polymer, for example a thermoplastic polymer, such as polyolefin, for example polypropylene and/or polyethylene, and/or polyester, for example polyethylene terephthalate (PET), and mixtures thereof. Filaments are typically considered continuous or substantially continuous in nature.

The filaments of the present invention may be spun from polymer melt compositions via suitable spinning operations, such as meltblowing and/or spunbonding and/or they may be obtained from natural sources such as vegetative sources, for example trees.

The filaments of the present invention may be monocomponent and/or multicomponent. For example, the filaments may comprise bicomponent fibers and/or filaments. The bicomponent fibers and/or filaments may be in any form, such as side-by-side, core and sheath, islands-in-the-sea and the like.

"Meltblowing" is a process for producing filaments directly from polymers or resins using high-velocity air or another appropriate force to attenuate the filaments before collecting the filaments on a collection device, such as a belt, for example a patterned belt or molding member. In a meltblowing process the attenuation force is applied in the form of high speed air as the material (polymer) exits a die or spinnerette.

"Spunbonding" is a process for producing filaments directly from polymers by allowing the polymer to exit a die or spinnerette and drop a predetermined distance under the forces of flow and gravity and then applying a force via high velocity air or another appropriate source to draw and/or attenuate the polymer into a filament.

"Fiber" as used herein means an elongate particulate as described above that exhibits a length of less than 5.08 cm (2 in.) and/or less than 3.81 cm (1.5 in.) and/or less than 2.54 cm (1 in.). Pulp fibers, for example wood pulp fibers typically exhibit a length of from about 0.7 mm to about 2.5 mm.

Fibers are typically considered discontinuous in nature. Non-limiting examples of fibers include pulp fibers, such as wood pulp fibers, and synthetic staple fibers such as polypropylene, polyethylene, polyester, copolymers thereof, rayon, lyocell, glass fibers and polyvinyl alcohol fibers.

Staple fibers may be produced by spinning a filament tow and then cutting the tow into segments of less than 5.08 cm (2 in.) thus producing fibers; namely, staple fibers.

"Pulp fibers" as used herein means fibers that have been derived from vegetative sources, such as plants and/or trees.

In one example of the present invention, "pulp fiber" refers to papermaking fibers. In one example of the present invention, a fiber may be a naturally occurring fiber, which means it is obtained from a naturally occurring source, such as a vegetative source, for example a tree and/or plant, such as trichomes. Such fibers are typically used in papermaking and are oftentimes referred to as papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to fibrous structures made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. Also applicable to the present invention are fibers derived from recycled paper, which may contain any or all of the above categories of fibers as well as other non-fibrous polymers such as fillers, softening agents, wet and dry strength agents, and adhesives used to facilitate the original papermaking.

In one example, the wood pulp fibers are selected from the group consisting of hardwood pulp fibers, softwood pulp fibers, and mixtures thereof. The hardwood pulp fibers may be selected from the group consisting of: tropical hardwood pulp fibers, northern hardwood pulp fibers, and mixtures thereof. The tropical hardwood pulp fibers may be selected from the group consisting of: *eucalyptus* fibers, *acacia* fibers, and mixtures thereof. The northern hardwood pulp fibers may be selected from the group consisting of: cedar fibers, maple fibers, and mixtures thereof.

In addition to the various wood pulp fibers, other cellulosic fibers such as cotton fibers, cotton linters, rayon, lyocell, trichomes, seed hairs, rice straw, wheat straw, bamboo, and bagasse fibers can be used in this invention. Other sources of cellulose in the form of fibers or capable of being spun into fibers include grasses and grain sources.

"Trichome" or "trichome fiber" as used herein means an epidermal attachment of a varying shape, structure and/or function of a non-seed portion of a plant. In one example, a trichome is an outgrowth of the epidermis of a non-seed portion of a plant. The outgrowth may extend from an epidermal cell. In one embodiment, the outgrowth is a trichome fiber. The outgrowth may be a hairlike or bristle-like outgrowth from the epidermis of a plant.

Trichome fibers are different from seed hair fibers in that they are not attached to seed portions of a plant. For example, trichome fibers, unlike seed hair fibers, are not attached to a seed or a seed pod epidermis. Cotton, kapok, milkweed, and coconut coir are non-limiting examples of seed hair fibers.

Further, trichome fibers are different from non-wood bast and/or core fibers in that they are not attached to the bast, also known as phloem, or the core, also known as xylem portions of a non-wood dicotyledonous plant stem. Non-limiting examples of plants which have been used to yield non-wood bast fibers and/or non-wood core fibers include kenaf, jute, flax, ramie and hemp.

Further trichome fibers are different from monocotyledonous plant derived fibers such as those derived from cereal straws (wheat, rye, barley, oat, etc), stalks (corn, cotton, sorghum, *Hesperaloe funifera*, etc.), canes (bamboo, bagasse, etc.), grasses (esparto, lemon, sabai, switchgrass, etc), since such monocotyledonous plant derived fibers are not attached to an epidermis of a plant.

Further, trichome fibers are different from leaf fibers in that they do not originate from within the leaf structure. Sisal and abaca are sometimes liberated as leaf fibers.

Finally, trichome fibers are different from wood pulp fibers since wood pulp fibers are not outgrowths from the epidermis of a plant; namely, a tree. Wood pulp fibers rather originate from the secondary xylem portion of the tree stem.

"Particle" as used herein means a solid material, such as a powder, granule, agglomerate, encapsulate, microcapsule, and/or prill. The shape of the particle can be in the form of spheres, rods, plates, tubes, squares, rectangles, discs, stars, or have regular or irregular random forms such as a globular form. The particles of the present invention, at least those of at least 44 µm, can be measured by the Particle Size Distribution Test Method described herein. For particles that are less than 44 µm, a different test method may be used, for example light scattering, to determine the particle sizes less than 44 µm, for example perfume microcapsules that typically range from about 15 µm to about 44 µm and/or about 25 µm in size.

As used herein, a particle is not a fiber as defined herein, however, particles may comprise recycled materials derived from fibers, for example as a result of fibers being processed, for example recycled, by grinding fibers into a finely-divided solid and re-incorporating said finely-divided solids into agglomerates, granules or other particle forms.

In one example, the particles of the present invention may comprise recycled material, compostable material, and/or biodegradable material.

The particles of the present invention may comprise SAP particles, perfume particles, odor controlling particles (such as zeolites, charcoal, activated charcoal, beta-cyclodextrin and mixtures thereof), abrasive particles (such as silica), and thickening, gelling particles, for example blood clotting material particles, such as chitosan, alginates, coagulants and other naturally occurring gelling and/or thickening particles. In one example, the particles comprise SAP particles, especially when the structure, for example fibrous structure of the present invention will be utilized as an absorbent material, such as an absorbent core material.

"SAP particles" as used herein is a material that absorbs liquids, for example urine and/or menses, by transfer of the liquids across the periphery of the material forming a gelatinous substance, which imbibes the liquids and tightly holds the liquids. In one example, SAP particles retain greater than 5 times their weight of deionized water when subjected to centrifugal forces of less than or equal to 3000 G's for 10 to 15 minutes. In comparison, typically capillary absorbents retain about 1 times their weight under similar conditions. Non-limiting examples of SAP particles include crosslinked polyacrylic acids and/or crosslinked carboxymethyl cellulose.

SAP particle comprises a synthesized, cross-linked polymeric material that can absorb and retain, via hydrogen bonding and/or chemical absorption into its polymer chains (chemical storage) tens or even hundreds of times its own weight in aqueous fluid. SAP particles are now commonly (although not exclusively) made from the polymerization of acrylic acid blended with sodium hydroxide in the presence of an initiator to form a poly-acrylic acid sodium salt (sometimes referred to as sodium polyacrylate). Other non-limiting examples of materials that may be used to make SAP particles include polyacrylamide copolymer, ethylene maleic anhydride copolymer, cross-linked carboxymethyl-cellulose, polyvinyl alcohol copolymers, cross-linked polyethylene oxide, and starch grafted copolymer of polyacrylonitrile and biological blood binding and/or blood clotting material particles agents such as alginates. Current manufacturing sources of SAP particles suitable for use in the processes and structures, for example absorbent material, described herein include (but are not limited to) Nippon Shokubai (Osaka, Japan), BASF (Ludwigshafen (on the Rhine), Germany) and Evonik Industries (Essen, North Rhine-Westphalia, Germany).

In one example, the SAP particles comprise a highly crosslinked sodium polyacrylate that results in the SAP particles absorbing and retaining liquids, such as urine and/or menses, even under moderate pressure. Such SAP particles are suitable for absorbent materials that can included in diapers, feminine care products, and/or adult incontinence products for example.

In another example, the SAP particles comprise a lightly crosslinked sodium polyacrylate that results in the SAP particles absorbing liquids, such as urine and/or menses, but release under moderate pressure. Such SAP particles are suitable for absorbent materials that can be included in floor cleaning pads, for example.

In one example, the SAP particles may comprise recycled material, compostable material, and/or biodegradable material.

In one example, the first particles, for example SAP particles may comprise water-insoluble particles.

In one example, the first particles, for example SAP particles may comprise water swellable particles.

Smaller SAP particles, for example SAP particles exhibiting an average particle size of less than 300 µm and/or less than 200 µm and/or less than 100 µm absorb liquids, for example urine and/or menses, faster than larger SAP particles, for example SAP particles exhibiting an average particle size of greater than 400 µm and/or greater than 500 µm and/or greater than 600 µm.

"Stokes Number" or Stk is defined mathematically as $$Stk = \frac{t_p}{t_o}$$

"Particle Time Constant" or $t_p$ is defined mathematically as $$t_p = \frac{\rho_d d_d^2}{18\mu_g}$$

where $\rho_d$ is the particle ("solid additive") density, $d_d$ is the geometric mean of the major and minor particle axes, and $\mu_g$ is the viscosity of the fluid carrying the particle, for example air.

"Fluid Time Constant" or $t_o$ is defined mathematically as $$t_o = \frac{l_o}{v_o}$$

where $l_o$ is the length of interest in a region of analysis and $v_o$ is the bulk velocity in the region of analysis "Basis Weight" as used herein is the weight per unit area of a sample reported in lbs/3000 ft$^2$ or g/m$^2$ (gsm) and is measured according to the Basis Weight Test Method described herein.

"Machine Direction" or "MD" as used herein means the direction parallel to the flow of the fibrous structure through the fibrous structure making machine and/or sanitary tissue product manufacturing equipment.

"Cross Machine Direction" or "CD" as used herein means the direction parallel to the width of the fibrous structure making machine and/or sanitary tissue product manufacturing equipment and perpendicular to the machine direction.

"Different" as used herein with respect to particles, means two or more particles exhibit different properties for example different sizes, shapes, densities, masses, Stokes Numbers, and/or compositions.

"Ply" as used herein means an individual, integral fibrous structure.

"Plies" as used herein means two or more individual, integral fibrous structures disposed in a substantially contiguous, face-to-face relationship with one another, forming a multi-ply sanitary tissue product. It is also contemplated that an individual, integral fibrous structure can effectively form a multi-ply sanitary tissue product, for example, by being folded on itself.

"X" or "Y" or "xy", and "Z" or "z" designate a conventional system of Cartesian coordinates, wherein mutually perpendicular coordinates "X" and "Y" define a reference X-Y (xy) plane, and "Z" defines an orthogonal to the X-Y plane. "Z-direction" designates any direction perpendicular to the X-Y plane. Analogously, the term "Z-dimension" means a dimension, distance, or parameter measured parallel to the Z-direction. When an element, such as, for example, a molding member curves or otherwise deplanes, the X-Y plane follows the configuration of the element.

"Non-elastic" as used herein means a material does not exhibit elastic properties and/or elasticity and/or elastomeric.

"Particle size distribution span" as used herein means the (D90−D10)/D50×100%.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Process for Making a Fibrous Structure

Figure 3A:
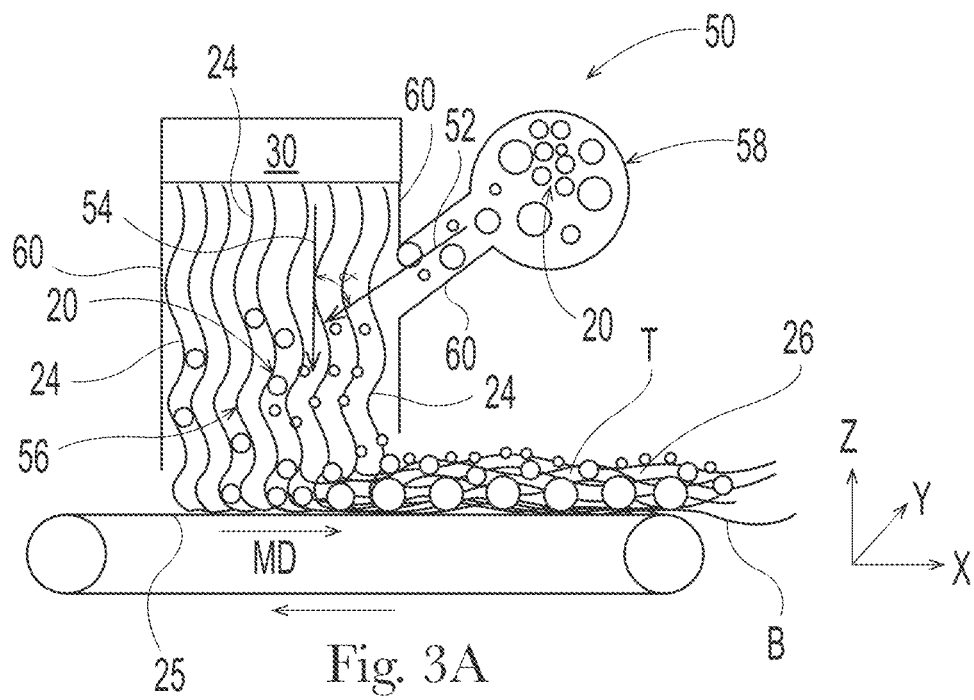
FIG. 3A is a schematic representation of an example of a process according to the present invention.

In one example as shown in FIG. 3A, an inventive process 50 of the present invention is a process for controlling the distribution of particles 20 within a structure 26, for example a fibrous structure, such as an absorbent material, for example an absorbent core material. In one example the fibrous structure made by the process of the present invention exhibits the properties and comprises the components suitable for use in the process of the present invention. The process 50 comprises the steps of commingling a particle stream 52 (a fluid stream comprising a plurality of particles 20) (represented by an arrow) comprising a plurality of particles 20 with a filament stream 54 (a fluid stream comprising a plurality of filaments 24) (represented by an arrow) comprising a plurality of filaments 24 to form a composite fluid stream 56 (composite stream 56) and collecting the composite stream 56 on a collection device 25, for example a belt, such that a structure 26, for example a fibrous structure, such as an absorbent material, for example an absorbent core material that exhibits a non-random arrangement of the plurality of particles 20 in the structure is formed.

The plurality of particles 20 may be introduced into the process 50 by a particle source 58, for example a hopper, by way of the particle stream 52 originating from the particle source 58.

The plurality of filaments 24 may be introduced into the process 50 by a filament source 30, for example a die, such as a meltblow die and/or spunbond die, for example a knife edge die or a multi-row capillary die, examples of which are available from Biax-Fiberfilm Corporation of Greenville, WI, by way of the filament stream 54 originating from the filament source 30.

The particle stream 52 may intersect the filament stream 54 at an angle α during the process 50. Angle α may range from about 5° to about 130° and/or from about 10° to about 110° and/or from about 20° to about 90° and/or from about 40° to about 90°.

In one example, the particle stream 52 and filament stream 54 intersect and commingle in a closed environment and/or substantially closed environment, for example an enclosure (housing) 60, such as a coforming box, such that the filament source 30 and optionally the particle source 58 are connected to and are in fluid communication with the enclosure 60 as shown for example in FIG. 3A.

Figure 3B:
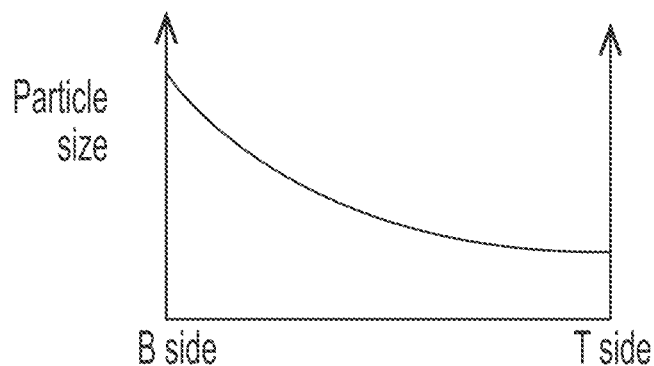
FIG. 3B is a schematic representation of a distribution of particles based on particle size that can be produced by the process of FIG. 3A.
Figure 3C:
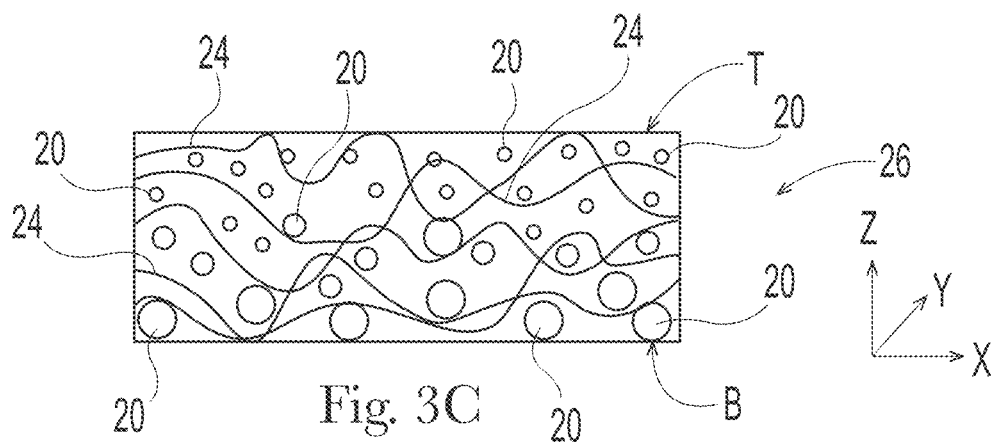
FIG. 3C is a schematic representation of an example of a fibrous structure according to the present invention that can be produced by the process of FIG. 3A.

Further, as shown in FIG. 3A, the process 50 may be arranged as a single-sided, single-injection of the plurality of particles 20, which produces a structure 26, for example a fibrous structure, such as an absorbent material, for example an absorbent core material that exhibits a non-random arrangement (a controlled distribution or designed distribution) particle size distribution of particles 20 as shown in FIGS. 3B and 3C. The non-random arrangement particle size distribution creates a structure, such as a fibrous structure, for example an absorbent material, such as an absorbent core material that exhibits a continuous gradient of relatively large particles, for example relatively higher Stokes Number particles on and/or near one side (the bottom B side) and relatively small particles, for example relatively lower Stokes Number particles on and/or near the opposite side (the top T side).

Figure 4A:
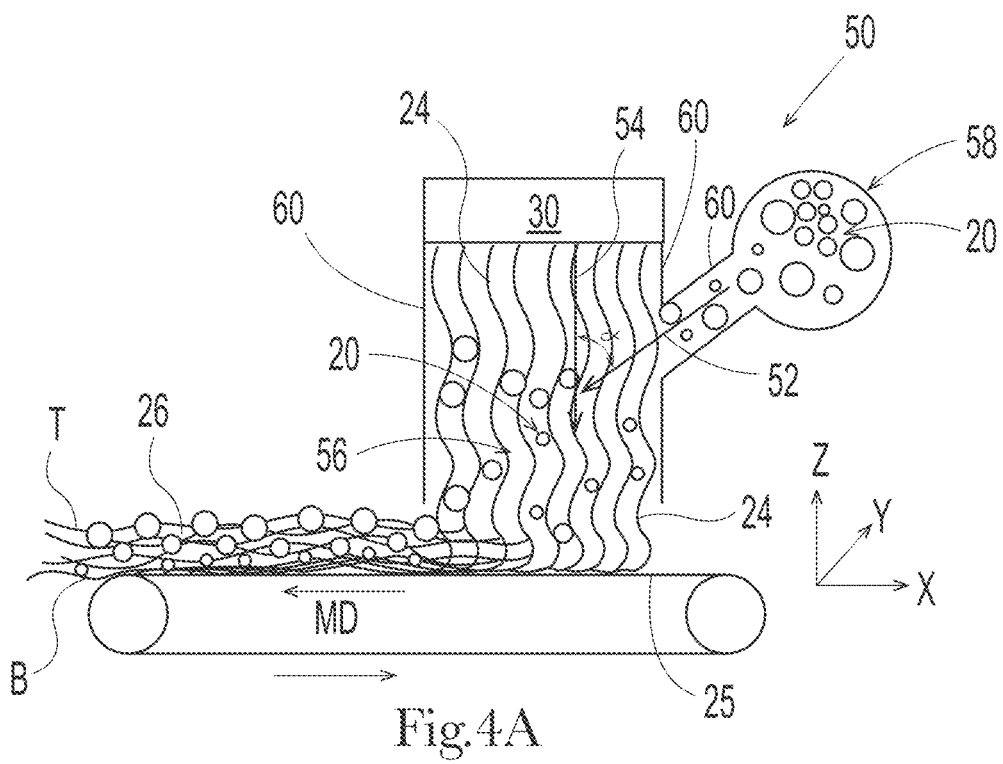
FIG. 4A is a schematic representation of another example of a process according to the present invention.

In another example as shown in FIG. 4A, an inventive process 50 of the present invention is a process for controlling the distribution of particles 20 within a structure 26, for example a fibrous structure, such as an absorbent material, for example an absorbent core material. The process 50 comprises the steps of commingling a particle stream 52 (represented by an arrow) comprising a plurality of particles 20 with a filament stream 54 (represented by an arrow) comprising a plurality of filaments 24 to form a composite stream 56 and collecting the composite stream 56 on a collection device 25, for example a belt, such that a structure 26, for example a fibrous structure, such as an absorbent material, for example an absorbent core material that exhibits a non-random arrangement of the plurality of particles 20 in the structure is formed.

The plurality of particles 20 may be introduced into the process 50 by a particle source 58, for example a hopper, by way of the particle stream 52 originating from the particle source 58.

The plurality of filaments 24 may be introduced into the process 50 by a filament source 30, for example a die, such as a meltblow die and/or spunbond die, for example a knife edge die or a multi-row capillary die, examples of which are available from Biax-Fiberfilm Corporation of Greenville, WI, by way of the filament stream 54 originating from the filament source 30.

The particle stream 52 may intersect the filament stream 54 at an angle α during the process 50. Angle α may range from about 5° to about 130° and/or from about 10° to about 110° and/or from about 20° to about 90° and/or from about 40° to about 90°.

In one example, the particle stream 52 and filament stream 54 intersect and commingle in a closed environment, for example an enclosure (housing) 60, such as a coforming box, such that the filament source 30 and optionally the particle source 58 are connected to and are in fluid communication with the enclosure 60 as shown for example in FIG. 4A.

Figure 4B:
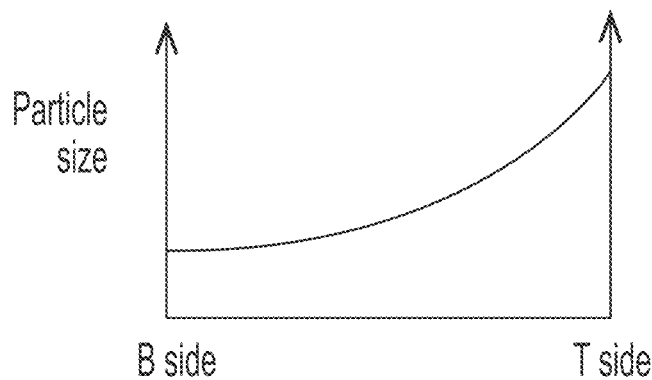
FIG. 4B is a schematic representation of a distribution of particles based on particle size that can be produced by the process of FIG. 4A.
Figure 4C:
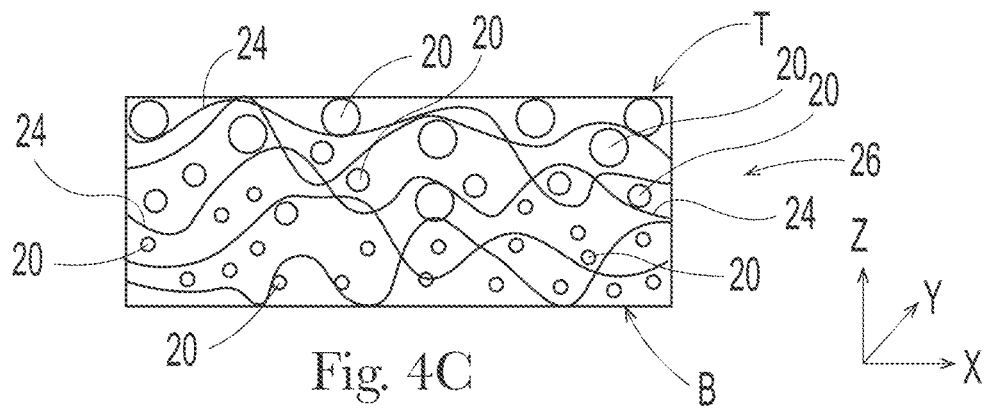
FIG. 4C is a schematic representation of an example of a fibrous structure according to the present invention that can be produced by the process of FIG. 4A.

Further, as shown in FIG. 4A, the process 50 may be arranged as a single-sided, single-injection of the plurality of particles 20, which produces a structure, for example a fibrous structure, such as an absorbent material, for example an absorbent core material that exhibits a non-random arrangement (a controlled distribution or designed distribution) particle size distribution as shown in FIGS. 4B and 4C. The non-random arrangement particle size distribution creates a structure, such as a fibrous structure, for example an absorbent material, such as an absorbent core material that exhibits a continuous gradient of relatively large particles, for example relatively higher Stokes Number particles on and/or near one side (the top T side) and relatively small particles, for example relatively lower Stokes Number particles on and/or near the opposite side (the bottom B side).

In another example, the process 50 may be arranged as a single-sided, dual-injection (not shown) of the plurality of particles 20 such that two different particle streams 52 (a first particle stream and a second particle stream), which may comprise different particles 20 are introduced into the filament stream 54. The intersection of the different particle streams 52 with the filament stream 54 may occur at the same spot or different spots along the filament stream 54. In still another example, the process 50 may be arranged as a single-sided, multi-injection of the plurality of particles 20 such that multiple (three or more) different particle streams 52, which may comprise different particles are introduced into the filament stream 54. The intersection of the different particle streams 52 with the filament stream 54 may occur at the same spot and/or different spots along the filament stream 54. The non-random arrangement (controlled distribution or designed distribution) particle size distributions for the single-sided, dual-injection and/or the single-sided, multi-injection processes 50 would look similar to FIGS. 3B and 3C or 4B and 4C.

Figure 5A:
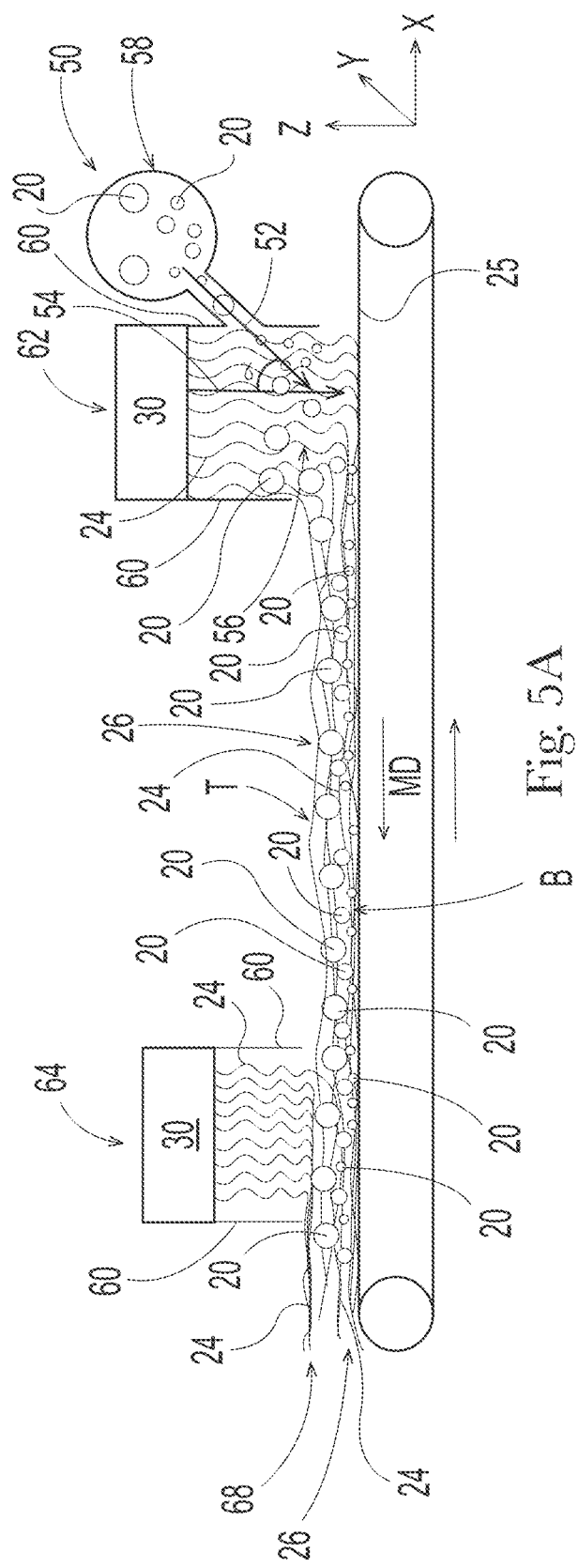
FIG. 5A is a schematic representation of another example of a process according to the present invention.
Figure 5B:
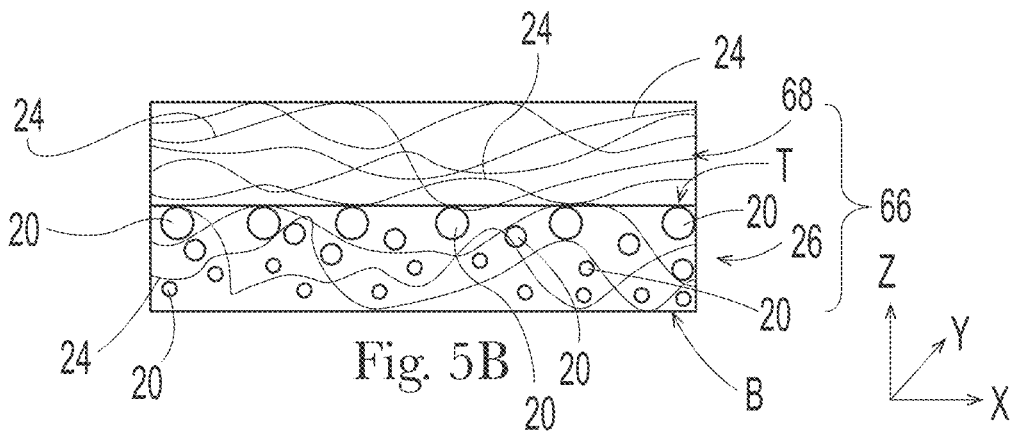
FIG. 5B is a schematic representation of an example of a fibrous structure according to the present invention that can be produced by the process of FIG. 5A.

In even another example of the present invention, as shown in FIG. 5A, the process 50 comprises a first beam 62 comprising a filament source 30 and a particle source 58 as described above with respect to FIG. 4A. Operation of the first beam 62 like the process described above with respect to FIG. 4A results in a resulting structure 26 comprising a non-random arrangement of particles 20, for example a continuous gradient of particle sizes of the particles 20 within the resulting structure 26. As shown in FIG. 5A, the resulting structure 26 comprises a continuous gradient of particle sizes with larger size particles near the top T side and smaller size particles near the bottom B side. After forming the resulting structure 26, the top T side surface of the resulting structure 26 is then contacted with a second plurality of filaments 24 spun from a second filament source 30 from a second beam 64 creating a layered structure 66, for example a fibrous structure, such as an absorbent material, for example an absorbent core material, as shown in FIG. 5B. The second plurality of filaments 24 are spun directly onto the top T side surface of the resulting structure 26 to form a layer of filaments 24, which may function as a scrim layer 68 to help retain the particles 20 within the resulting structure 26. In the case of FIG. 5B, the average fiber diameter of the filaments 24 in the resulting structure 26 and the filaments 24 in the scrim layer 68 are the same or substantially the same.

Figure 5C:
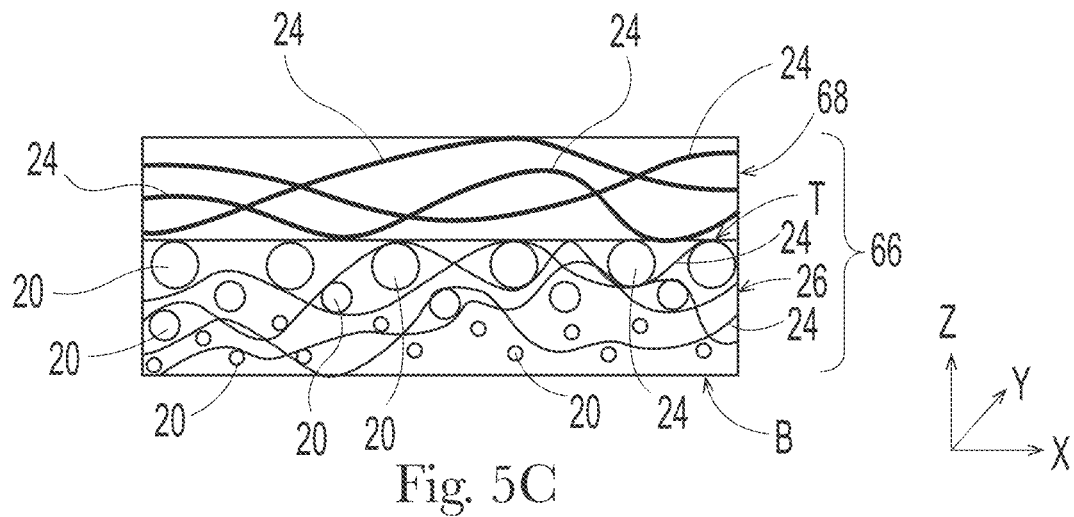
FIG. 5C is a schematic representation of another example of a fibrous structure according to the present invention that can be produced by the process of FIG. 5A.
Figure 5D:
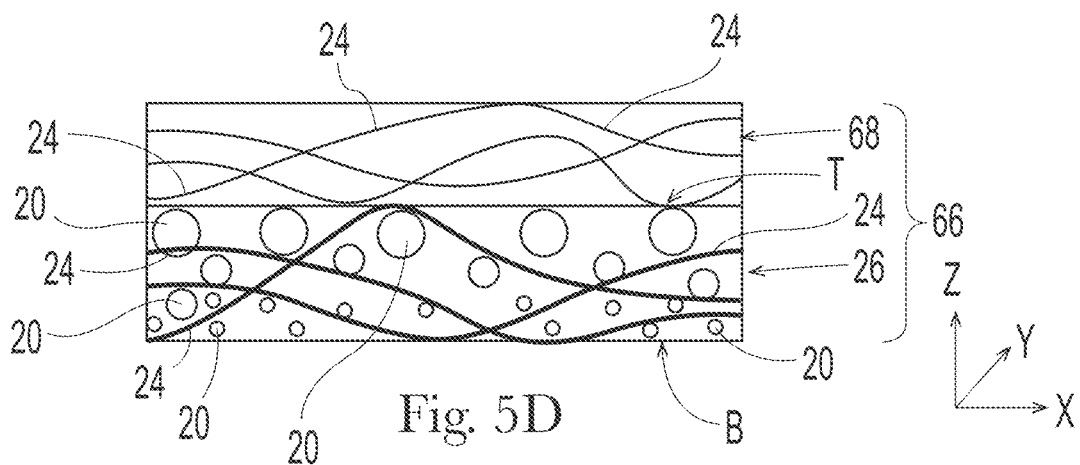
FIG. 5D is a schematic representation of another example of a fibrous structure according to the present invention that can be produced by the process of FIG. 5A.

The layered structures 66 shown in FIGS. 5C and 5D may also be formed by the process 50 of FIG. 5A by producing different average fiber diameter filaments 24 from at least two different beams. FIG. 5C shows an example of a layered structure 66 where the first beam 62 produces filaments 24 exhibiting a smaller average fiber diameter than the filaments 24 produced by the second beam 64, which creates the scrim layer 68. The particles 20 in the layered structure 66 of FIG. 5C are present in the resulting structure 26 in a non-random arrangement, for example a continuous gradient of particle sizes. FIG. 5D shows another example of a layered structure 66 where the first beam 62 produces filaments 24 exhibiting a larger average fiber diameter than the filaments 24 produced by the second beam 64, which creates the scrim layer 68. The particles 20 in the layered structure 66 of FIG. 5D are present in the resulting structure 26 in a non-random arrangement, for example a continuous gradient of particle sizes.

Figure 6A:
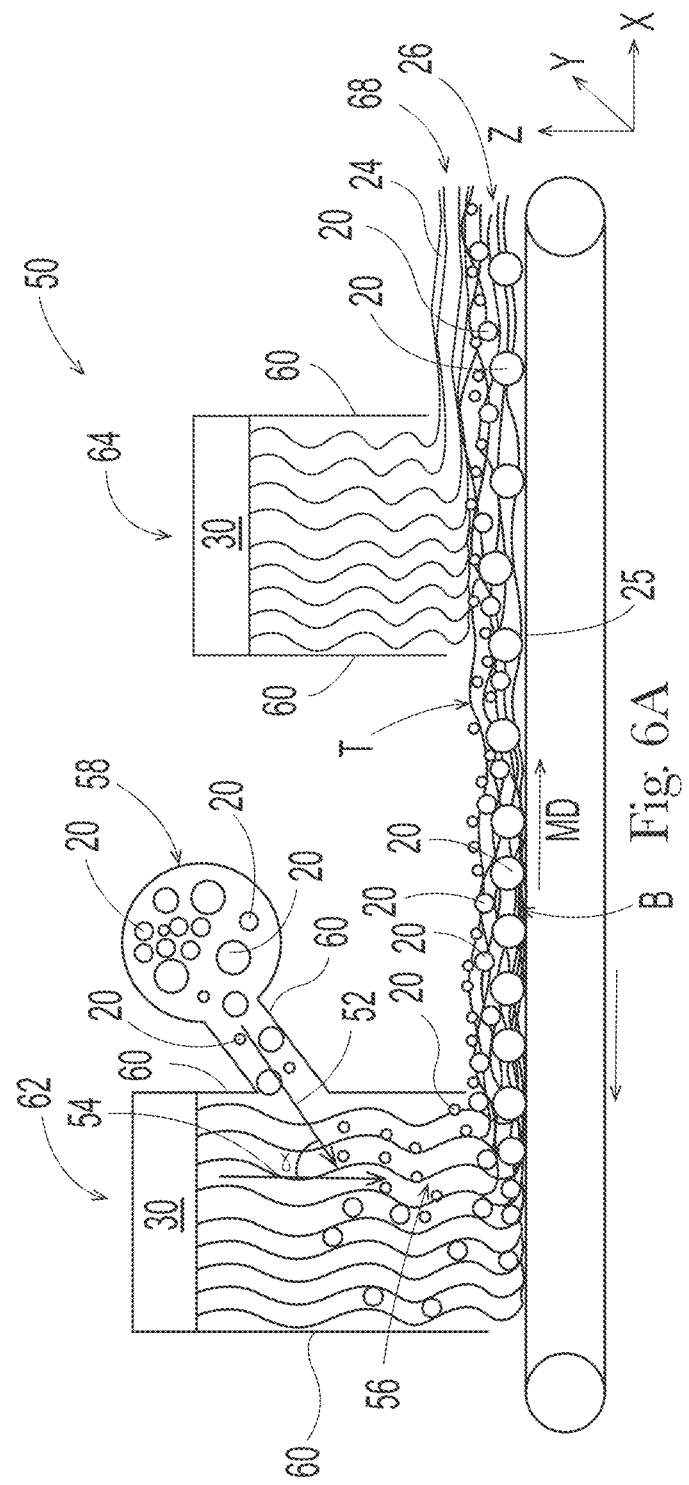
FIG. 6A is a schematic representation of another example of a process according to the present invention.
Figure 6B:
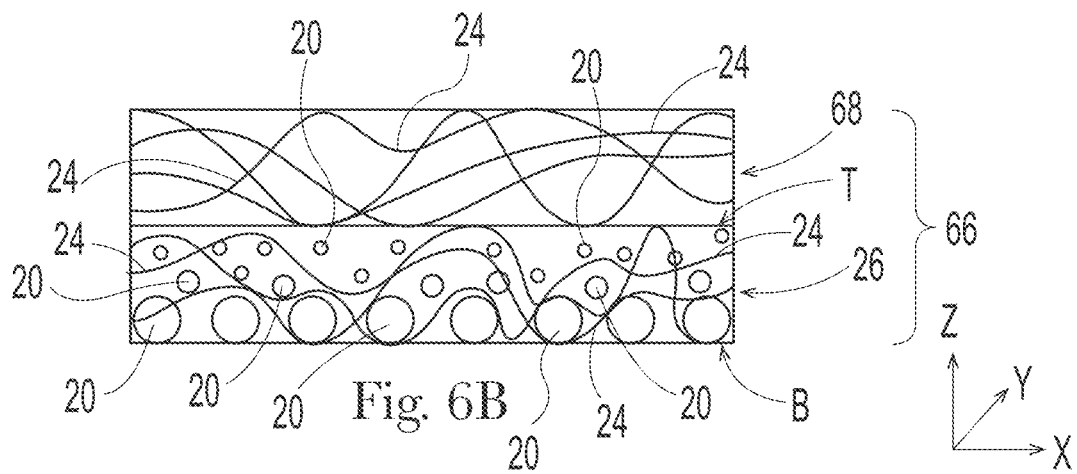
FIG. 6B is a schematic representation of an example of a fibrous structure according to the present invention that can be produced by the process of FIG. 6A.

In even yet another example of the present invention, as shown in FIG. 6A, the process 50 comprises a first beam 62 comprising a filament source 30 and a particle source 58 as described above with respect to FIG. 3A. Operation of the first beam 62 like the process described above with respect to FIG. 3A results in a resulting structure 26 comprising a non-random arrangement of particles 20, for example a continuous gradient of particle sizes of the particles 20 within the resulting structure 26. As shown in FIG. 6A, the resulting structure 26 comprises a continuous gradient of particle sizes with larger size particles near the bottom B side and smaller size particles near the top T side. After forming the resulting structure 26, the top T side surface of the resulting structure 26 is then contacted with a second plurality of filaments 24 spun from a second filament source 30 from a second beam 64 creating a layered structure 66, for example a fibrous structure, such as an absorbent material, for example an absorbent core material, as shown in FIG. 6B. The second plurality of filaments 24 are spun directly onto the top T side surface of the resulting structure 26 to form a layer of filaments 24, which may function as a scrim layer 68 to help retain the particles 20 within the resulting structure 26. In the case of FIG. 6B, the average fiber diameter of the filaments 24 in the resulting structure 26 and the filaments 24 in the scrim layer 68 are the same or substantially the same.

Figure 6C:
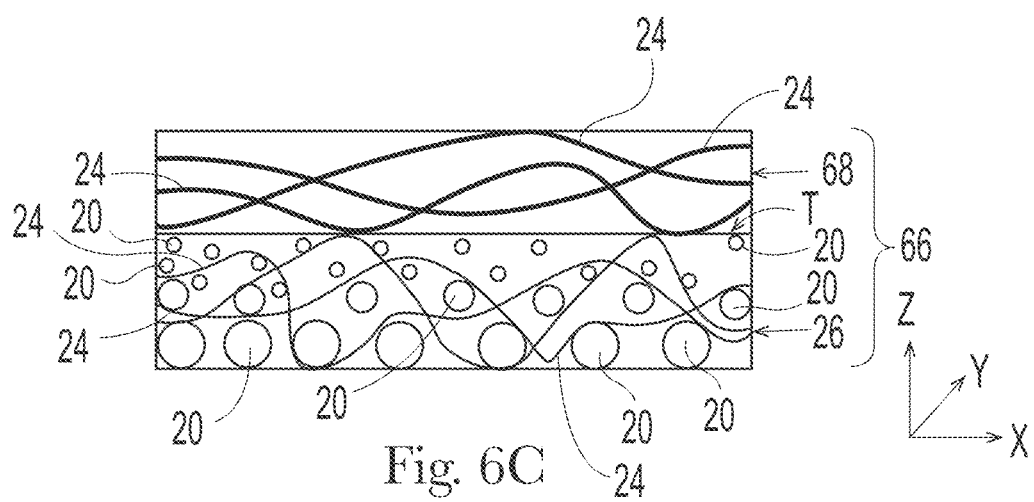
FIG. 6C is a schematic representation of another example of a fibrous structure according to the present invention that can be produced by the process of FIG. 6A.
Figure 6D:
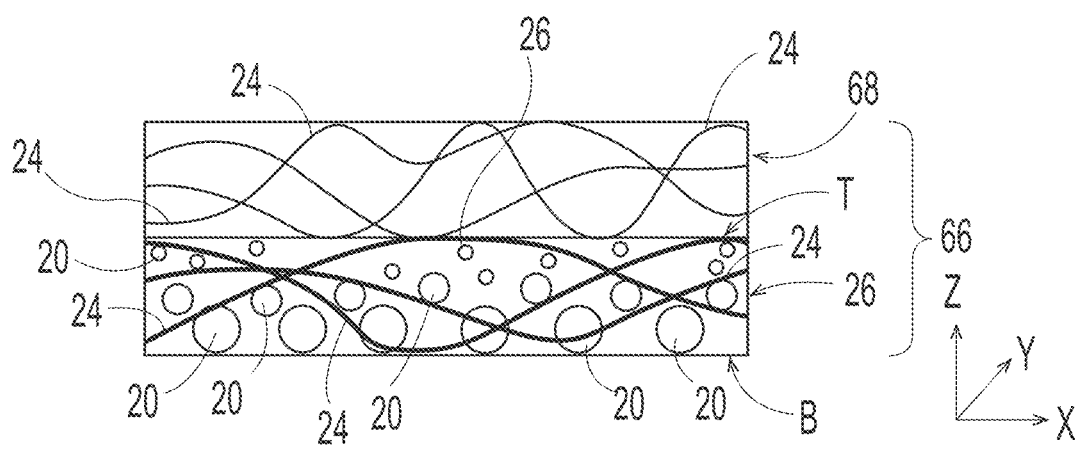
FIG. 6D is a schematic representation of another example of a fibrous structure according to the present invention that can be produced by the process of FIG. 6A.

The layered structures 66 shown in FIGS. 6C and 6D may also be formed by the process 50 of FIG. 6A by producing different average fiber diameter filaments 24 from at least two different beams. FIG. 6C shows an example of a layered structure 66 where the first beam 62 produces filaments 24 exhibiting a smaller average fiber diameter than the filaments 24 produced by the second beam 64, which creates the scrim layer 68. The particles 20 in the layered structure 66 of FIG. 6C are present in the resulting structure 26 in a non-random arrangement, for example a continuous gradient of particle sizes. FIG. 6D shows another example of a layered structure 66 where the first beam 62 produces filaments 24 exhibiting a larger average fiber diameter than the filaments 24 produced by the second beam 64, which creates the scrim layer 68. The particles 20 in the layered structure 66 of FIG. 6D are present in the resulting structure 26 in a non-random arrangement, for example a continuous gradient of particle sizes.

Figure 7A:
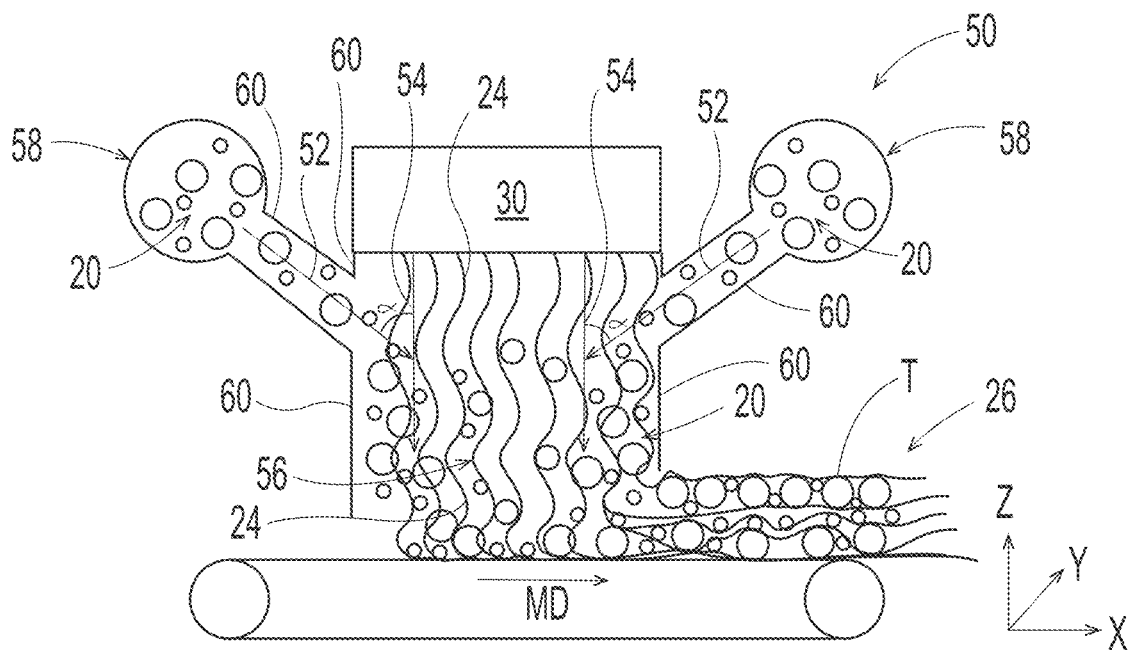
FIG. 7A is a schematic representation of another example of a process according to the present invention.
Figure 7B:
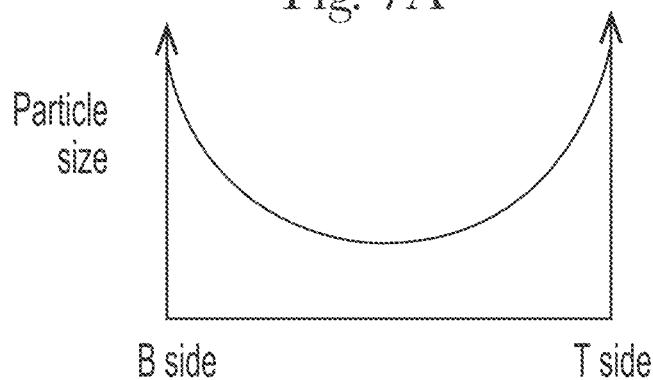
FIG. 7B is a schematic representation of a distribution of particles based on particle size that can be produced by the process of FIG. 7A.
Figure 7C:
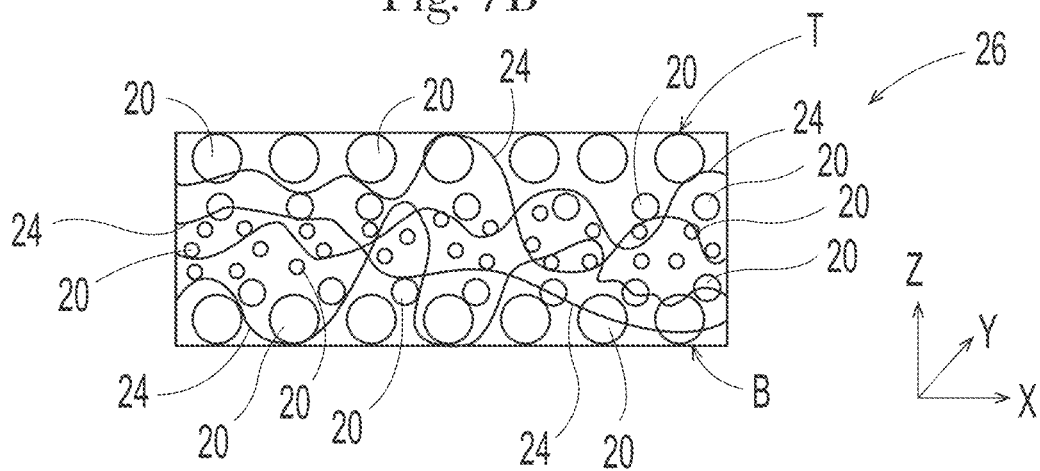
FIG. 7C is a schematic representation of an example of a fibrous structure according to the present invention that can be produced by the process of FIG. 7A.

In yet another example as shown in FIG. 7A, the process 50 may be arranged as a double-sided, dual-injection of the plurality of particles 20 where a first particle stream 52 is introduced on one side of the enclosure 60, such as the upstream side of the enclosure 60 and/or process 50 and a second particle stream 52 is introduced on another side of the enclosure 60, such as the downstream side of the enclosure 60 and/or process 50. Such a process 50 as shown in FIG. 7A produces a structure, for example a fibrous structure, such as an absorbent material, for example an absorbent core material that exhibits a non-random arrangement (a controlled distribution or designed distribution) particle size distribution as shown in FIGS. 7B and 7C. The non-random arrangement particle size distribution creates a structure, such as a fibrous structure, for example an absorbent material, such as an absorbent core material that exhibits a continuous gradient of relatively large particles, for example relatively higher Stokes Number particles on and/or near one side (for example the top T side) and relatively small particles to and through the center, for example relatively lower Stokes Number particles, and then relatively large particles, for example relatively higher Stokes Number particles, which may be the same, similar, or different from the large particles on and/or near the top T side, on and/or near the opposite side (for example the bottom B side). In another example, the process 50 may be arranged as a double-sided, dual-injection of the plurality of particles 20 such that two different particle streams 52, which may comprise different particles are introduced into the filament stream 54. The intersection of the different particle streams 52 with the filament stream 54 may occur at the same spot or different spots along the filament stream 54. In still another example, the process 50 may be arranged as a double-sided, multi-injection of the plurality of particles 20 such that multiple (three or more) different particle streams 52, which may comprise different particles are introduced into the filament stream 54. The intersection of the different particle streams 52 with the filament stream 54 may occur at the same spot and/or different spots along the filament stream 54.

Figure 8A:
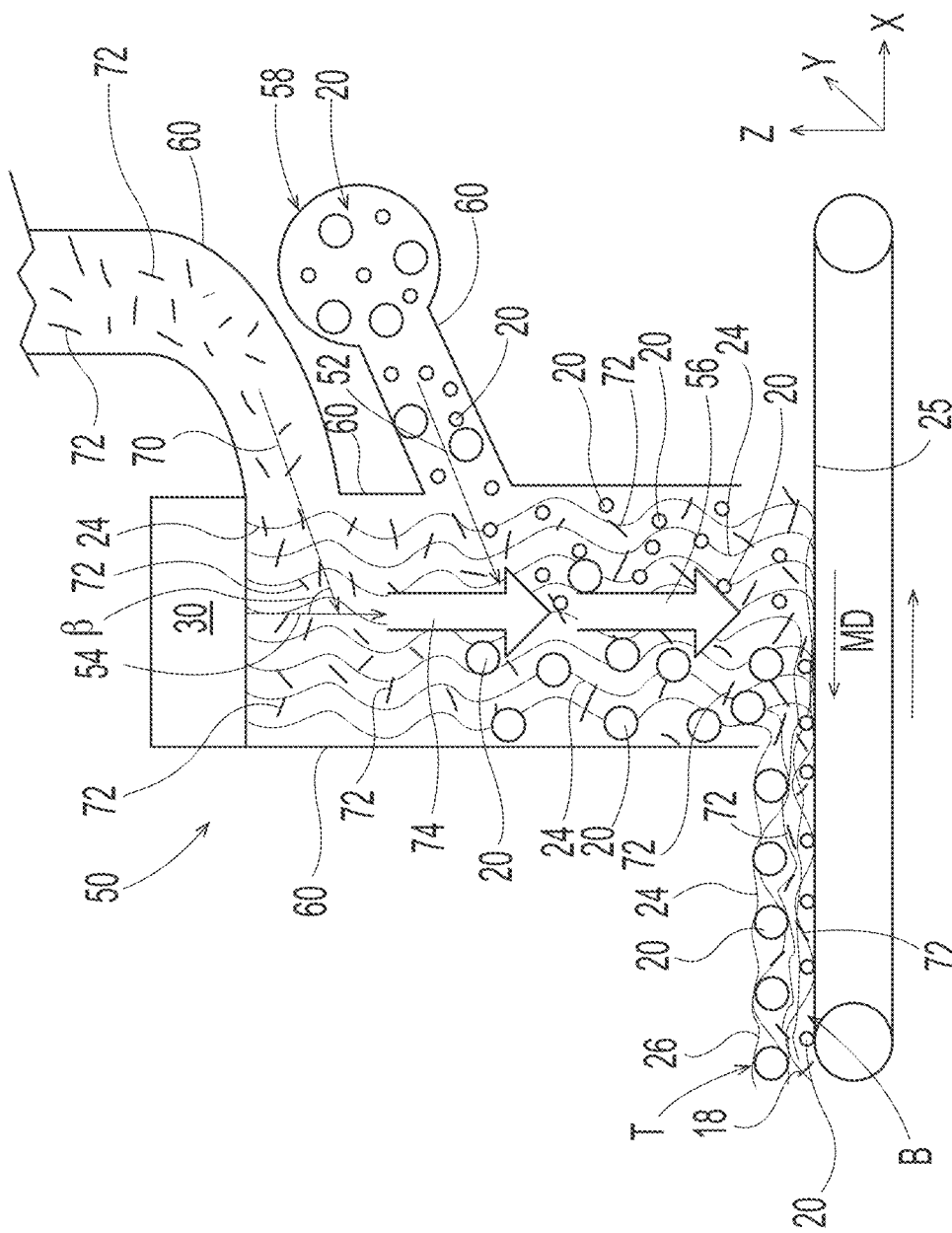
FIG. 8A is a schematic representation of another example of a process according to the present invention.

In addition to the controlled distribution of particles provided by the process of the present invention, the process 50 of the present invention as shown in FIG. 8A may optionally include, the addition of a non-particle solid additive stream 70 comprising a plurality of non-particle solid additives 72, for example fibers, such as pulp fibers, for example wood pulp fibers into the filament stream 54 and/or the composite stream 56. In one example, the non-particle solid additives 72, such as fibers, are kept separate from the particles 20 prior to introduction into the enclosure 60 and/or prior to commingling with the filaments 24. Likewise, the particles 20 are kept separate from the non-solid additive particles 72, for example fibers, prior to introduction into the enclosure 60 and/or prior to commingling with the filaments 24.

As shown in FIG. 8A, an example of a process 50 of the present invention comprises the steps of: a) commingling a stream of filaments 54 comprising a plurality of filaments 24 with a stream of non-particle solid additives 70 comprising a plurality of non-particle solid additives 72, for example fibers, such as pulp fibers, for example wood pulp fibers to form a mixed stream 74 comprising a plurality of filaments 24 and a plurality of non-particle solid additives 72; b) commingling a stream of particles 52 comprising a plurality of particles 20 as described above with the mixed stream 74 to form a composite stream 56 and collecting the composite stream 56 on a collection device 25, for example a belt, such that a structure 26, for example a fibrous structure, such as an absorbent material, for example an absorbent core material that exhibits a non-random arrangement of the plurality of particles 20 in the structure is formed. Such a structure 26 comprises a plurality of filaments 24, a plurality of non-particle solid additives 72, and a plurality of particles 20. The resulting structure 26 comprising a non-random arrangement of particles 20 in the resulting structure 26.

In the process 50 of the present invention as shown in FIG. 8A, the process 50 comprises the steps of commingling a non-particle solid additive stream 70 (represented by an arrow) comprising a plurality of non-particle solid additives 72 with a filament stream 54 (represented by an arrow) comprising a plurality of filaments 24 to form a mixed stream 74; commingling a particle stream 52 (represented by an arrow) comprising a plurality of particles 20 with the mixed stream 74 comprising a plurality of filaments 24 and a plurality of non-particle solid additives 72 to form a composite stream 56 comprising the plurality of particles 20, the plurality of non-particle solid additives 72, and the plurality of filaments 24; and collecting the composite stream 56 on a collection device 25, for example a belt, such that a structure 26, for example a fibrous structure, such as an absorbent material, for example an absorbent core material that exhibits a non-random arrangement of the plurality of particles 20 in the structure is formed.

The plurality of particles 20 may be introduced into the process 50 by a particle source 58, for example a hopper, by way of the particle stream 52 originating from the particle source 58.

The plurality of filaments 24 may be introduced into the process 50 by a filament source 30, for example a die, such as a meltblow die and/or spunbond die, for example a knife edge die or a multi-row capillary die, examples of which are available from Biax-Fiberfilm Corporation of Greenville, WI, by way of the filament stream 54 originating from the filament source 30.

The non-particle solid additives 72 may be introduced into the process 50 from a non-particle solid additive source (not shown), for example a hopper and/or a disintegrator, and/or a pickering roll, and/or a hammermill if one or more of the latter three examples if the non-particle solid additives 72 include fibers, such as pulp fibers, for example wood pulp fibers.

The particle stream 52 may intersect the filament stream 54 at an angle α during the process 50. Angle α may range from about 5° to about 130° and/or from about 10° to about 110° and/or from about 20° to about 90° and/or from about 40° to about 90°.

The non-particle solid additive stream 70 may intersect the filament stream 54 at an angle β during the process 50. Angle β may range from about 5° to about 130° and/or from about 10° to about 110° and/or from about 20° to about 90° and/or from about 40° to about 90°.

In one example, the non-particles solid additive stream 70, the filament stream 54, particle stream 52 and filament stream 54 intersect and commingle in a closed environment, for example an enclosure (housing) 60, such as a coforming box, such that the filament source 30 and optionally the particle source 58 are connected to and are in fluid communication with the enclosure 60 as shown for example in FIG. 3A.

Figure 8B:
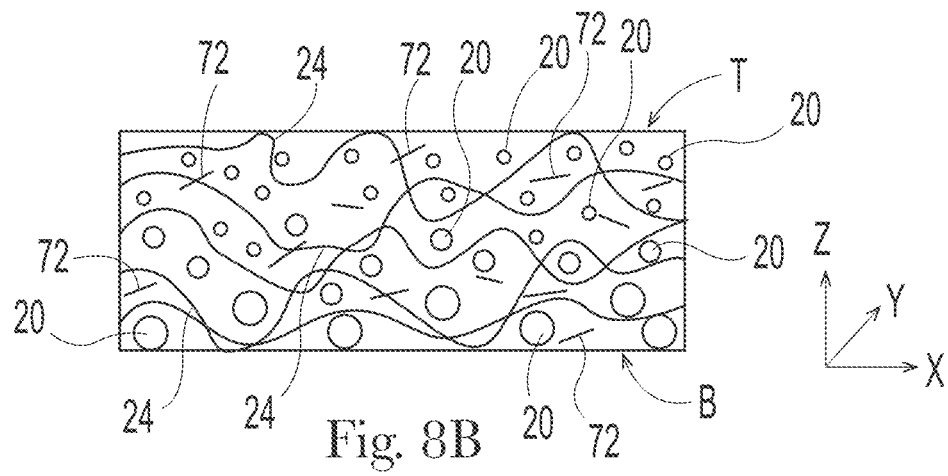
FIG. 8B is a schematic representation of an example of a fibrous structure according to the present invention that can be produced by the process of FIG. 8A.
Figure 8C:
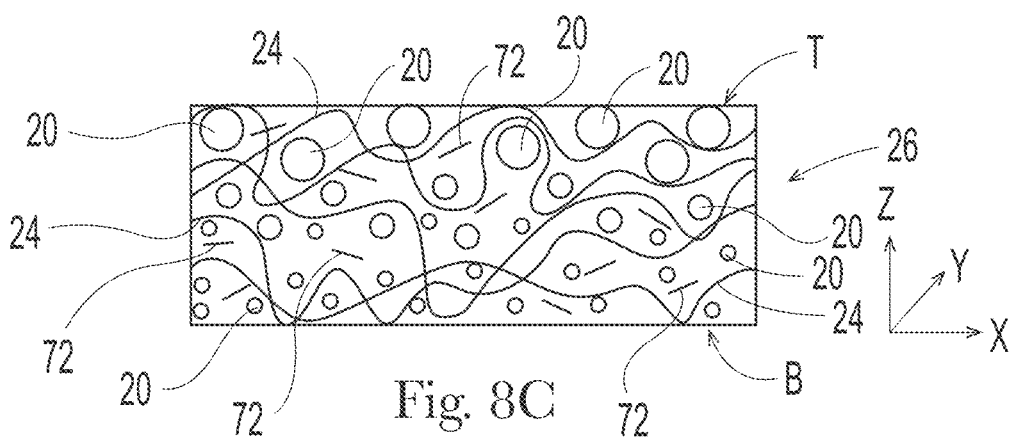
FIG. 8C is a schematic representation of another example of a fibrous structure according to the present invention that can be produced by the process of FIG. 8A.

Further, as shown in FIG. 8A, the process 50 may be arranged as a single-sided, single-injection of the plurality of particles 20, which produces a structure 26, for example a fibrous structure, such as an absorbent material, for example an absorbent core material that exhibits a non-random arrangement (a controlled distribution or designed distribution) particle size distribution of the particles 20 as shown in FIGS. 8B and 8C. The non-controlled distribution of the non-particle solid additives 72, for example fibers, such as pulp fibers, for example wood pulp fibers, results in a random and/or non-controlled arrangement of the non-particle solid additives 72 in the structure 26. The non-random arrangement particle size distribution creates a structure, such as a fibrous structure, for example an absorbent material, such as an absorbent core material that exhibits a continuous gradient of relatively large particles, for example relatively higher Stokes Number particles on and/or near one side (the bottom B side) and relatively small particles, for example relatively lower Stokes Number particles on and/or near the opposite side (the top T side) as shown in FIG. 8B, which would result from the set up shown in FIG. 8A if the MD direction was opposite that shown or alternatively, if the particle stream 52 was introduced on the opposite side of the enclosure 60. The resulting structure 26 as shown in FIG. 8C would result from the process 50 as shown in FIG. 8A where the structure 26, such as a fibrous structure, for example an absorbent material, such as an absorbent core material exhibits a continuous gradient of relatively large particles, for example relatively higher Stokes Number particles on and/or near one side (the top T side) and relatively small particles, for example relatively lower Stokes Number particles on and/or near the opposite side (the bottom B side) as shown in FIG. 8C.

Figure 8D:
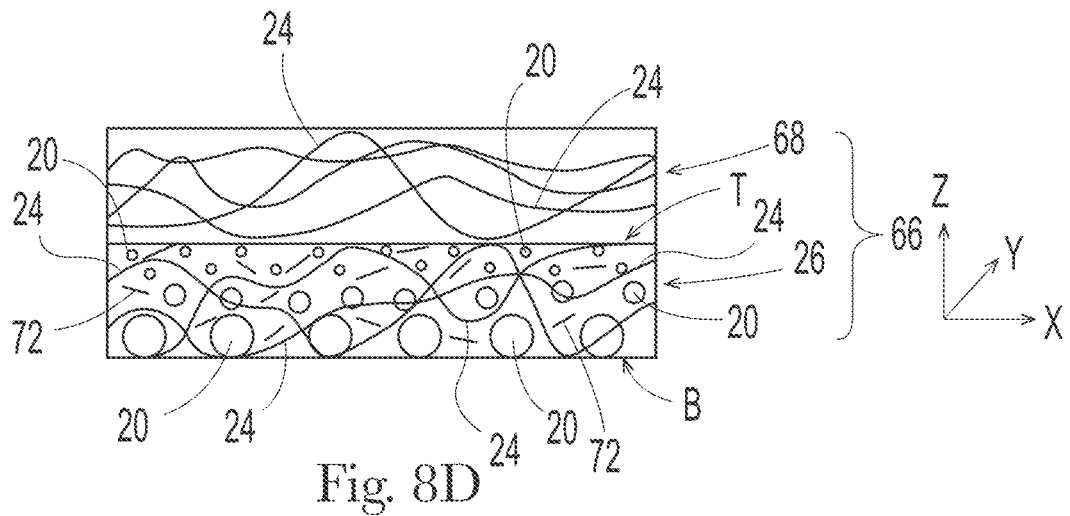
FIG. 8D is a schematic representation of another example of a fibrous structure according to the present invention that can be produced by the process of FIG. 8A.

The structure 26 shown in FIG. 8B may further include a scrim layer 68 by modifying the process shown in FIG. 6A by replacing the first beam 62 with the set up shown in FIG. 8A as modified to produce the structure 26 shown in FIG. 8B. The resulting layered structure 66 is illustrated in FIG. 8D.

Figure 8E:
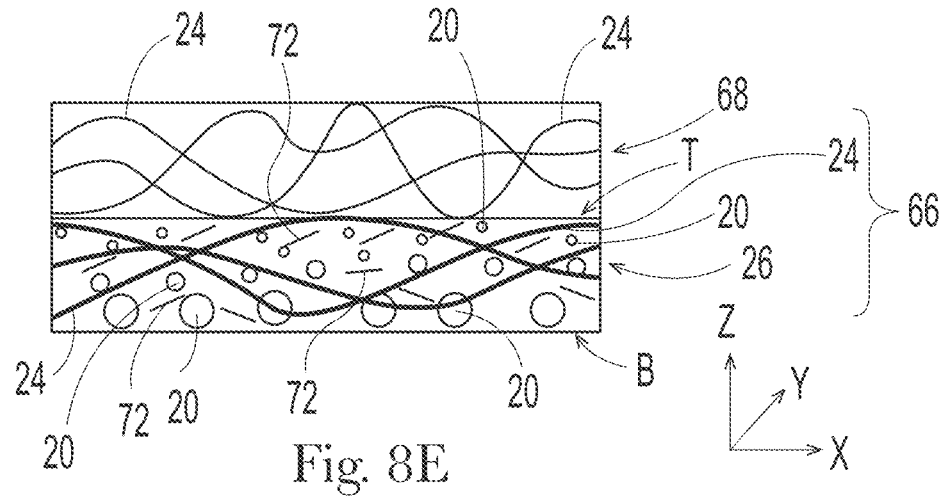
FIG. 8E is a schematic representation of another example of a fibrous structure according to the present invention that can be produced by the process of FIG. 8A.
Figure 8F:
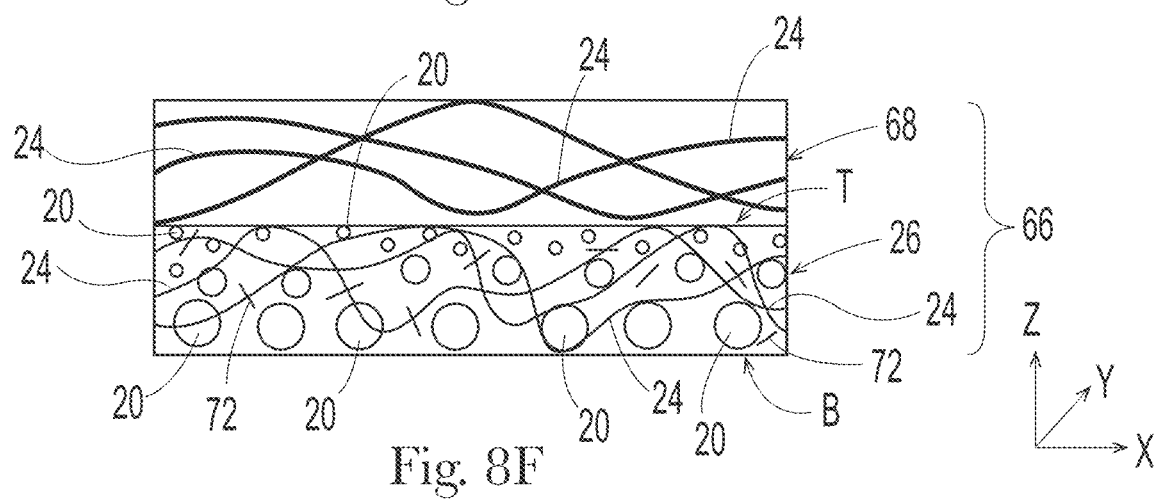
FIG. 8F is a schematic representation of another example of a fibrous structure according to the present invention that can be produced by the process of FIG. 8A.

The layered structure 66 may further include filaments 24 in the structure 26 layer and the scrim layer 68 that exhibit different average fiber diameters as described above. For example, FIG. 8E shows filaments 24 in the scrim layer 68 exhibiting a smaller average fiber diameter than the filaments 24 in the structure 26 layer. Likewise, FIG. 8F shows filaments 24 in the scrim layer 68 exhibiting a larger average fiber diameter than the filaments 24 in the structure 26 layer.

Figure 8G:
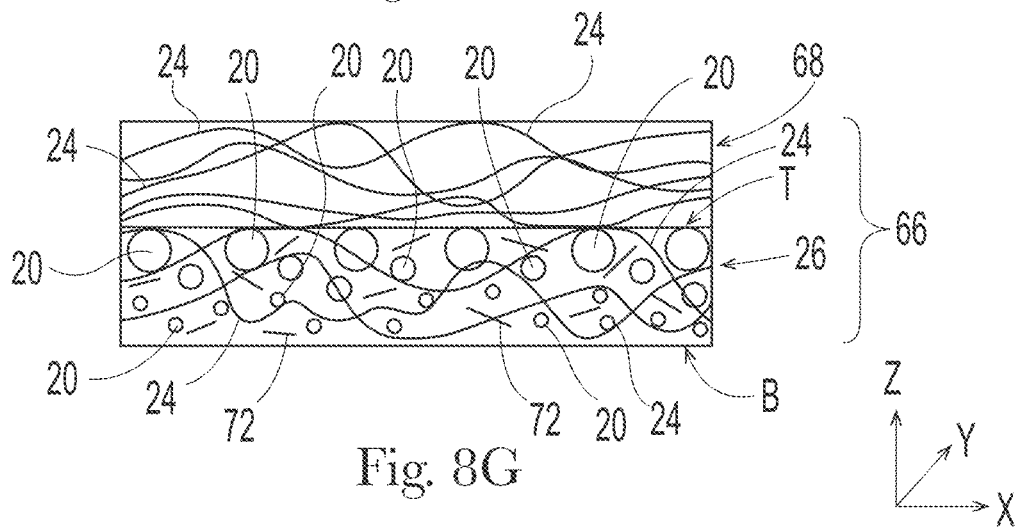
FIG. 8G is a schematic representation of another example of a fibrous structure according to the present invention that can be produced by the process of FIG. 8A.

The structure 26 shown in FIG. 8C may further include a scrim layer 68 by modifying the process shown in FIG. 5A by replacing the first beam 62 with the set up shown in FIG. 8A. The resulting layered structure 66 is illustrated in FIG. 8G.

Figure 8H:
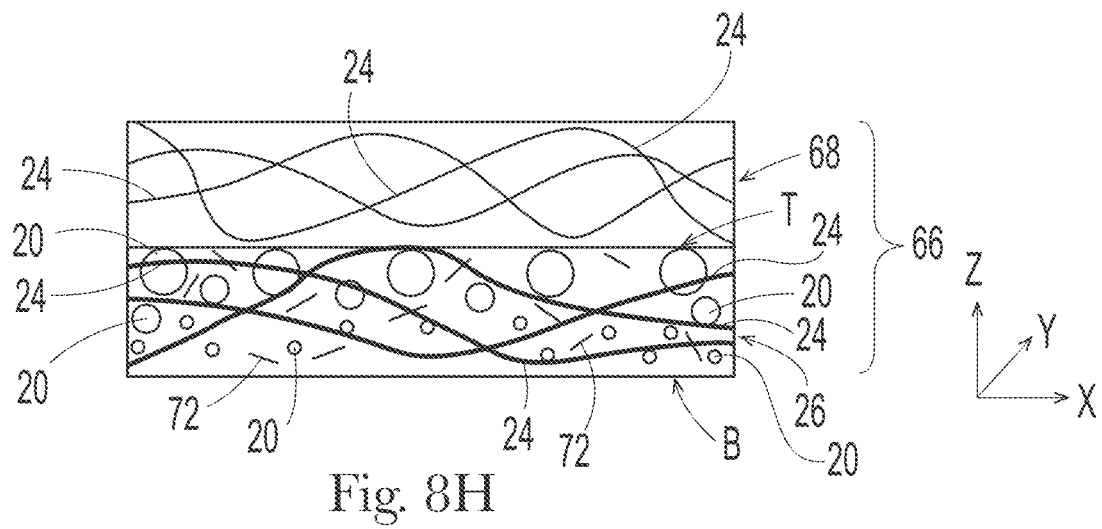
FIG. 8H is a schematic representation of another example of a fibrous structure according to the present invention that can be produced by the process of FIG. 8A.
Figure 8I:
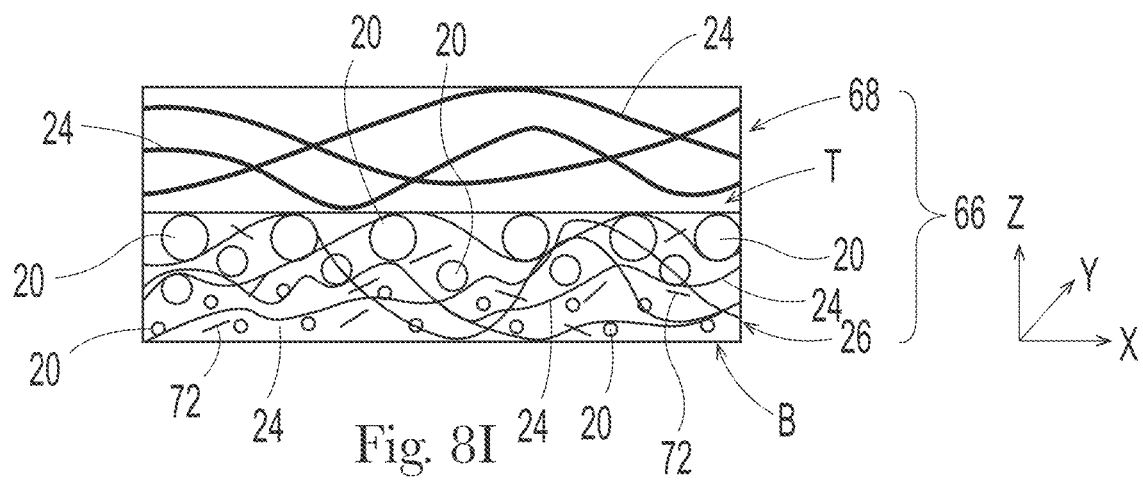
FIG. 8I is a schematic representation of another example of a fibrous structure according to the present invention that can be produced by the process of FIG. 8A.

The layered structure 66 may further include filaments 24 in the structure 26 layer and the scrim layer 68 that exhibit different average fiber diameters as described above. For example, FIG. 8H shows filaments 24 in the scrim layer 68 exhibiting a smaller average fiber diameter than the filaments 24 in the structure 26 layer. Likewise, FIG. 8I shows filaments 24 in the scrim layer 68 exhibiting a larger average fiber diameter than the filaments 24 in the structure 26 layer.

As discussed above, the average fiber diameters of filaments 24 produced from different filament sources 30, for example within the first beam 62 and the second beam 64, can be achieved for example by utilizing different velocities of attenuation air and/or different throughput of the polymer melt exiting the different filament sources 30.

Even though the processes 50 shown in FIGS. 5A and 6A only show exemplify two beams, the first beam 62 and the second beam 64, which makes a two layered structure 66, one or more additional beams, either a beam like the first beam 62 or a beam like the second beam 64 and/or both, may be added to the processes 50. For example if the process 50 comprises an additional beam like the second beam 64 that is positioned upstream (before) the first beam 62, then a first layer of a plurality of filaments 24 are spun onto the collection device 25 creating a first layer, for example a first scrim layer. The composite stream 56 from the first beam 62 would then be spun directly onto the first scrim layer and then a second scrim layer would be spun from the second beam 64 directly onto the layer formed from the composite stream 56 of the first beam 62 resulting in a three-layered structure with the structure 26 sandwiched between two scrim layers 68.

In one example, the angle α of intersection of the particle stream 52 with the filament stream 54 and/or the mixed stream 74 (depending on which process 50 embodiment is being operated) and/or the velocity of the fluid, such as air, carrying the particles 20 in the particle stream 52 can be varied and/or adjusted to control the distribution of the particles 20 within the process 50 and ultimately in the resulting structure 26, for example fibrous structure, such as an absorbent material, for example an absorbent core material such that a non-random arrangement of the plurality of particles 20 is created within the structure.

One or more particle streams 52 may be introduced into the filament stream 54 at any position within the enclosure 60 and/or process so long as the structure of the present invention is created. For example, one particle stream 52 may be introduced into the filament stream 54 at the upstream side of the enclosure 60 and/or process (for example substantially parallel to the MD). Likewise, a particle stream 52 may be introduced into the filament stream 54 at the downstream side of the enclosure 60 and/or process (for example substantially parallel to the MD).

In one example, the step of mixing the first fluid stream comprising a plurality of fibrous elements with the second fluid stream comprising a plurality of first particles occurs on the first fluid stream's upstream side at two or more positions.

In another example, the step of mixing the first fluid stream comprising a plurality of fibrous elements with the second fluid stream comprising a plurality of first particles occurs on the first fluid stream's downstream side at two or more positions.

In one example, the process further comprises the step of mixing a third fluid stream comprising a plurality of fibers with the first fluid stream comprising a plurality of fibrous elements. In one example, the step of mixing a third fluid stream comprising a plurality of fibers with the first fluid stream comprising a plurality of fibrous elements comprises commingling the plurality of fibers, for example pulp fibers, of the third fluid stream with the plurality of fibrous elements of the first fluid stream.

In one example, the process further comprises the step of mixing one or more additional fluid streams comprising a plurality of additional particles different from the plurality of first particles. In one example the plurality of additional particles comprises a composition different from the first particles' composition. In one example, at least one of the plurality of first particles exhibits a first Stokes Number that is different from at least one of the additional particles' Stokes Number.

In one example, the process further comprises the step of mixing a fourth fluid stream comprising a plurality of second particles with at least one of the first and second fluid streams. In one example, the plurality of second particles may be different from the plurality of first particles. In one example, the plurality of second particles may be the same as the plurality of first particles. In one example, the second and fourth fluid streams mix with the first fluid stream from different sides of the first fluid stream. In one example, the second fluid stream mixes with the first fluid stream from the downstream side of the first fluid stream and the fourth fluid stream mixes with the first fluid stream from the upstream side of the first fluid stream. In one example, the second fluid stream mixes with the first fluid stream from the drive side of the first fluid stream and the fourth fluid stream mixes with the first fluid stream from the downstream side of the first fluid stream. In one example, the second fluid stream mixes with the first fluid stream from the upstream side or the downstream side of the first fluid stream and the fourth fluid stream mixes with the first fluid stream from the upstream side and the downstream side of the first fluid stream.

In one example, the second and fourth fluid streams mix with the first fluid stream from same side of the first fluid stream.

In another example, the process further comprises the step of collecting the composite fluid stream on a collection device such that a fibrous structure exhibiting a non-random arrangement of the plurality of first particles in the fibrous structure is formed. In one example, the non-random arrangement of the plurality of first particles in the fibrous structure is based on a particle characteristic selected from the group consisting of: size, shape, mass, density, Stokes Number, and mixtures thereof. In one example, the particle characteristic is size, for example the non-random arrangement of the plurality of first particles in the fibrous structure comprises a first group of particles comprising at least a majority of larger size particles present in a first part of the fibrous structure's z-direction thickness and a second group of particles comprising at least a majority of smaller size particles present in a second part of the fibrous structure's z-direction thickness different from the first part and/or the first part of the fibrous structure's z-direction thickness is more proximate to one side of the fibrous structure than the second part and/or the second part of the fibrous structure's z-direction thickness is more proximate to one side of the fibrous structure than the first part and/or the first part of the fibrous structure's z-direction thickness is proximate to one side of the fibrous structure and the second part of the fibrous structure's z-direction thickness is proximate to the fibrous structure's opposite side.

In one example, the plurality of first particles in the fibrous structure is based on a particle characteristic Stokes Number, for example, the non-random arrangement of the plurality of first particles in the fibrous structure comprises a first group of particles comprising at least a majority of larger Stokes Number particles present in a first part of the fibrous structure's z-direction thickness and a second group of particles comprising at least a majority of smaller Stokes Number particles present in a second part of the fibrous structure's z-direction thickness different from the first part, such as the first part of the fibrous structure's z-direction thickness is more proximate to one side of the fibrous structure than the second part and/or the second part of the fibrous structure's z-direction thickness is more proximate to one side of the fibrous structure than the first part and/or the first part of the fibrous structure's z-direction thickness is proximate to one side of the fibrous structure and the second part of the fibrous structure's z-direction thickness is proximate to the fibrous structure's opposite side.

In one example, the non-random arrangement of the plurality of first particles in the fibrous structure is such that the plurality of first particles are present in a z-direction gradient in the fibrous structure based on a particle characteristic selected from the group consisting of: size, shape, mass, density, Stokes Number, and mixtures thereof, for example, particle characteristic is size. In one example, the z-direction gradient is a continuous gradient, for example, the continuous gradient is present throughout the entire z-direction thickness of the fibrous structure. In one example, the z-direction gradient is present in less than the entire z-direction thickness of the fibrous structure. In one example, the particle characteristic of the plurality of first particles is Stokes Number, for example, the z-direction gradient is a continuous gradient, for example wherein the continuous gradient is present throughout the entire z-direction thickness of the fibrous structure. In one example, the z-direction gradient is present in less than the entire z-direction thickness of the fibrous structure.

In one example, the fibrous structure comprises a homogeneous z-direction concentration of the first particles.

In one example, the fibrous structure comprises a non-homogeneous z-direction concentration of the first particles.

In one example, the fibrous structure comprises two or more different z-direction layers of concentration of the first particles.

In one example, the fibrous structure comprises two or more different xy-plane regions of the first particles based on a particle characteristic selected from the group consisting of: size, shape, mass, density, Stokes Number, and mixtures thereof. In one example, the two or more xy-plane regions of the first particles comprise two or more stripes of the first particles. In one example, at least one of the two or more stripes of the first particles exhibits a z-direction gradient of the first particles within the at least one stripe of the first particles based on a particle characteristic selected from the group consisting of: size, shape, mass, density, Stokes Number, and mixtures thereof.

In one example, the fibrous structure comprises two or more different xy-plane regions of the first particles based on different concentration levels of the first particles.

In one example, the fibrous structure comprises a first group of the plurality of first particles concentrated proximate a first third of the z-direction thickness of the fibrous structure and a second group of the plurality of first particles concentrated proximate the opposite third of the z-direction thickness of the fibrous structure, for example, the first group of the plurality of first particles exhibit a maximum particle size that is at least two times the maximum particle size of the second group of the plurality of first particles, such as wherein the first group of the plurality of first particles exhibit a maximum particle size that is at least three times the maximum particle size of the second group of the plurality of first particles.

In one example, the process further comprises the step of depositing a scrim layer on at least one surface of the fibrous structure, for example wherein the scrim layer comprises a plurality of scrim filaments, for example water-insoluble filaments and/or thermoplastic filaments, such as thermoplastic filaments comprising a polyolefin, for example, a polyolefin selected from the group consisting of: propylene, ethylene, copolymers thereof, and mixtures thereof.

In one example, the process comprises two or more of the steps of mixing a first fluid stream comprising a plurality of fibrous elements and a second fluid stream comprising a plurality of first particles.

In one example, the collection device of the process comprises a nonwoven web material.

In one example, the plurality of first particles are present in the fibrous structure at a basis weight of from about 10 gsm to about 1000 gsm.

In one example, the process for making a particle-containing fibrous structure, the process comprising the steps of:
 a. adding a plurality of first particles to a first stream of first filaments having a first average diameter to form a first composite stream;
 b. collecting the first composite stream onto a collection device to form a first layer of the fibrous structure;
 c. adding a plurality of second particles to a second stream of second filaments having a second average diameter different from the first average diameter to form a second composite stream;
 d. collecting the second composite stream directly onto the first layer of the fibrous structure to form a layered fibrous structure comprising the first layer and a second layer formed from the second composite stream.

In one example, the first average diameter is less than the second average diameter, for example, wherein the first average diameter is less than 6 μm and/or from about 2 to about 5 μm.

In one example, the second average diameter is 6 μm or greater, for example, wherein the second average diameter is from about 6 to about 10 μm.

In one example, the first stream of first filaments further comprises a plurality of first fibers, for example pulp fibers, such as wood pulp fibers.

In one example, the plurality of first fibers is commingled with the first stream of first filaments, for example, wherein the commingling of the plurality of fibers with the stream of filaments occurs contemporaneously with the addition of the plurality of first particles to the first stream of first filaments and/or wherein the commingling of the plurality of first fibers with the first stream of first filaments occurs prior to the addition of the plurality of first particles to the first stream of first filaments.

In one example, the step of adding a plurality of first particles to a first stream of first filaments occurs within an enclosure.

In one example, the step of adding a plurality of first particles to a first stream of first filaments occurs within a closed environment.

In one example, the step of adding a plurality of first particles to a first stream of first filaments occurs at an addition angle of from about 30° to about 120°.

In one example, the plurality of first particles are homogeneously distributed in the layered fibrous structure in a non-random arrangement of the plurality of first particles in the layered fibrous structure, for example, wherein the non-random arrangement is a layered distribution of the plurality of first particles in the fibrous structure based upon one or more different particle characteristics within the plurality of particles.

The controlled distribution of particles of the present invention allows particles 20 to be placed within the resulting structure, for example fibrous structure, such as an absorbent material, for example an absorbent core material where desired in the x, y, and z directions, for example in different regions and/or zones and/or stripes.

Further, the controlled distribution of particles of the present invention allows particles 20 to be placed within the resulting structure, for example fibrous structure, such as an absorbent material, for example an absorbent core material where desired in the x, y, and z directions, to create different regions and/or zones and/or stripes based on concentration (meaning amount and/or level, for example mass per unit volume and/or % by weight) of particles, types of particles, size of particles, densities of particles, mass of particles, Stokes Numbers of particles, and/or shapes of particles.

FIG. 9 is a schematic representation of an example of a process 50 of the present invention. Related Table 1 below defines elements of FIG. 9. As shown in FIG. 9, the introduction of the particles (not shown) from the particle stream 52 from a particle source (not shown) via a nozzle 75 and/or the filament stream 54 and/or the mixed stream 74 can be adjusted in a non-limiting manner such that the angle α may exhibit the range of angles described above.

TABLE 1

| Code in FIG. 9 | Definition | Examples |
| --- | --- | --- |
| Region of mixing | The volume enclosing the mixing of particles and fibrous elements, for example filaments and/or fibers, that create the composite fluid stream that when collected on the collection device forms the fibrous structure of the present invention. | About 100 mm to 800 mm length × 100 mm to 4000 mm depth × 100 mm to 1000 mm height, for example about 200 mm to about 600 mm and/or about 300 mm to about 500 mm length and about 100 mm to about 500 mm and/or about 200 mm to about 400 mm depth and about 200 mm to about 800 mm and/or about 400 mm to about 600 mm height. |
| Collection device (Collection belt) (25) | The collection device (collection belt) is the device that collects the composite fluid stream into a fibrous structure and provides a reference point for all distances and angles. The collection device is typically in a horizontal position but could also be positioned vertically or at an angle vs ground level. The collection device will typically have the shape of a single plane. However in case of a non-planar collection device, the angle of the collection device at the center of the laydown (line R) will serve as a reference point | Flat and horizontal, diagonal or vertical, flat or curved, in one example flat and horizontal through laydown area |

TABLE 1-continued

| Code in FIG. 9 | Definition | Examples |
|---|---|---|
| R | R is the hypothetical line that defines the center of the laydown. It defines the plane that separates the total mass of the laydown into two equal parts, one side upstream and one side downstream of the line. R is perpendicular to the collection belt | Centered in region of mixing or shifted towards 25 percentile of upstream side of region of mixing, or 75 percentile of downstream of mixing, for example about centered in region of mixing |
| Nozzles (75) | Device for injecting particles into the mixing region. It typically has the shape of a nozzle, typically with a width similar to, or slightly more narrow, than desired width of the laydown of the particles. Several nozzles can be used simultaneously to obtain the desired combination of distribution of various particles embedded in the fibrous structure.<br>The position of the nozzles can be changed both parallel to collection device as well as perpendicular to the collection device. Furthermore the angle of the nozzle, defined as a line between the tip of the nozzle and the pivot point of the nozzle, can be changed | Open slot (uniform laydown)<br>Partially open slot (to create zones in MD that contains high stokes particles)<br>Nozzle positioned in MD (injects in MD direction), for example open slot position in MD (injects particles in MD direction) |
| d1, d2 | The minimum and maximum distance between the tip of the nozzle and the collection device (downstream side of the region of mixing) | d1 = about 5 mm to about 20 mm, for example 10 mm, d2 = about 500 mm to about 2000 mm, for example 1000 mm (same as start of region of mixing in the above definition) |
| e1, e2 | The minimum and maximum distance between the tip of the nozzle and the collection device (upstream side of the region of mixing) | e1 = about 5 mm to about 20 mm, for example about 10 mm, e2 = about 100 mm to about 1000 mm, for example about 300 mm (same as start of region of mixing) |
| Q1 | Reference line perpendicular to the collection device that defines the pivot point of the of the nozzle on the downstream side of the mixing region | About 100 mm to about 500 mm |
| Q2 | Reference line perpendicular to the collection device that defines the position of the tip of the nozzle on the downstream side of the mixing region | |
| d3 | Distance between Q2 and R. | About 100 mm to 300 mm, for example about 200 mm |
| e3 | Distance between S2 and R. | About 100 mm to 300 mm, for example about 200 mm |
| Q2 | Reference line perpendicular to the collection device that defines the pivot point for the nozzle | |
| A1, A2 | The angle of a nozzle on downstream side of the region of mixing, defined as the angle between the line that intersect the pivot point of the nozzle and the tip of the nozzle vs the Q1, with 0 degrees for a nozzle that would be pointing down towards the collection device, and 45 degree pointing diagonally towards the mixing region | Between 5 and 130 degrees, for example 20-90 degrees |
| S1 | Reference line perpendicular to the collection device that defines the pivot point of the of the nozzle on the downstream side of the mixing region | |
| S2 | Reference line perpendicular to the collection device that defines the position of the tip of the nozzle on the downstream side of the mixing region | |
| B1, B2 | The angle of a nozzle at the upstream side of the region of mixing, defined as the angle between the line that intersect the pivot point of the nozzle and the tip of the nozzle vs the Q1, with 0 degrees for a nozzle that would be pointing down towards the collection device, and 45 degree pointing diagonally towards the mixing region | Between 5 and 130 degrees, for example 20-90 degrees |

The integration of particles into a fibrous element stream, for example a filament stream, to create a composite fluid stream comprising the fibrous elements, for example filaments, and the particles, and ultimately create a fibrous structure upon collection of the composite fluid stream on a collection device, is not trivial, especially when the particles are introduced through a separate fluid stream, for example air stream, comprising a plurality of the particles. Factors that may influence this integration may include one or more of the following: 1) mass flow, velocity and angle of all other airflows, for example the fluid stream comprising the fibrous elements, because the fluid stream of the fibrous elements may require different properties and conditions than the fluid stream comprising the particles; 2) the Stokes Number of the particles, which involves physical properties such as particle density, particle shape and particle size, will dictate the trajectory of each particle depending on the angle and velocity of the particle as it enters the region of mixing; and 3) the desired distribution of particles in the x,y,z dimensions of the resulting fibrous structure both in terms of particle intensity, for example concentration (such as mass ratio vs other materials at a given location) as well as particle size (such as non-uniform particle size distribution)

Figure 10:
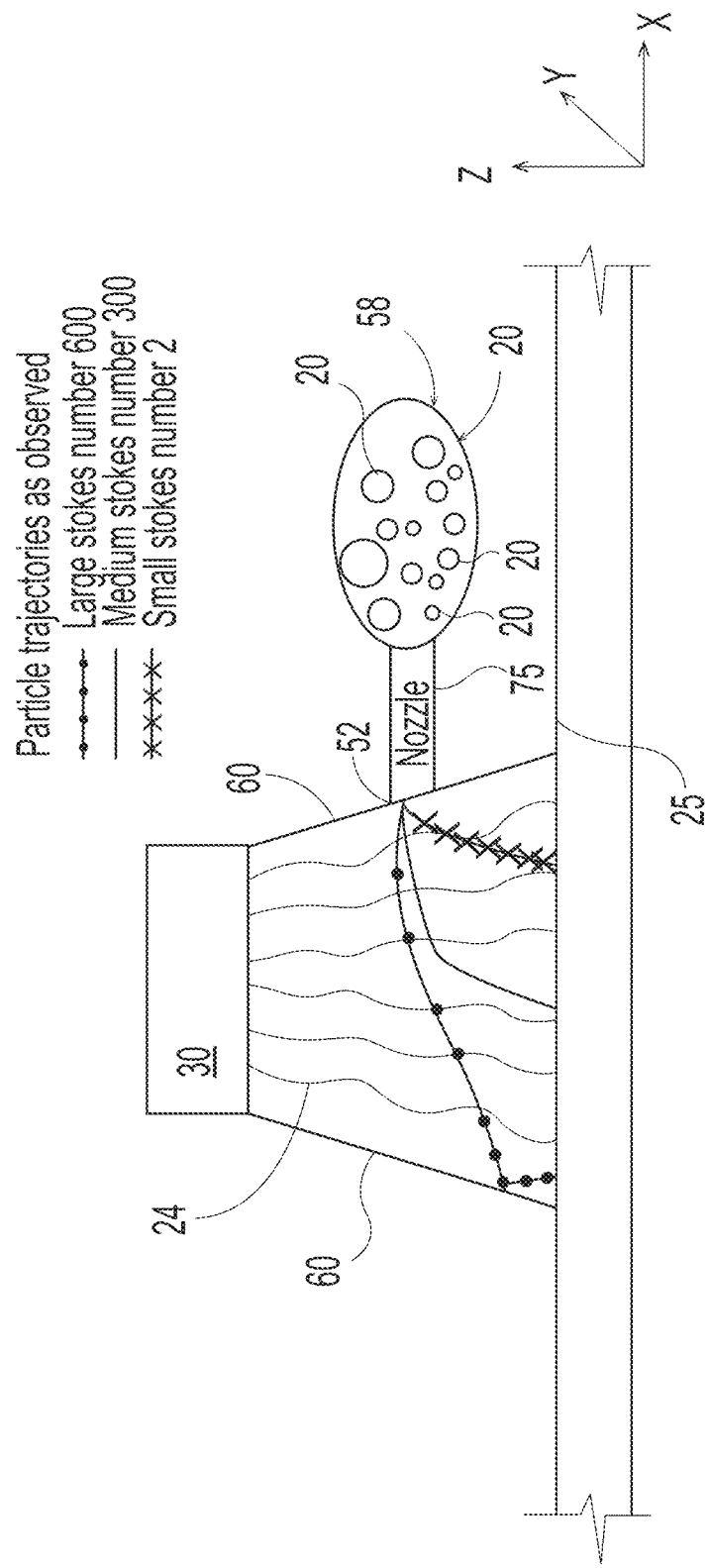
FIG. 10 is a schematic representation of an example of a process according to the present invention.
Figure 11:
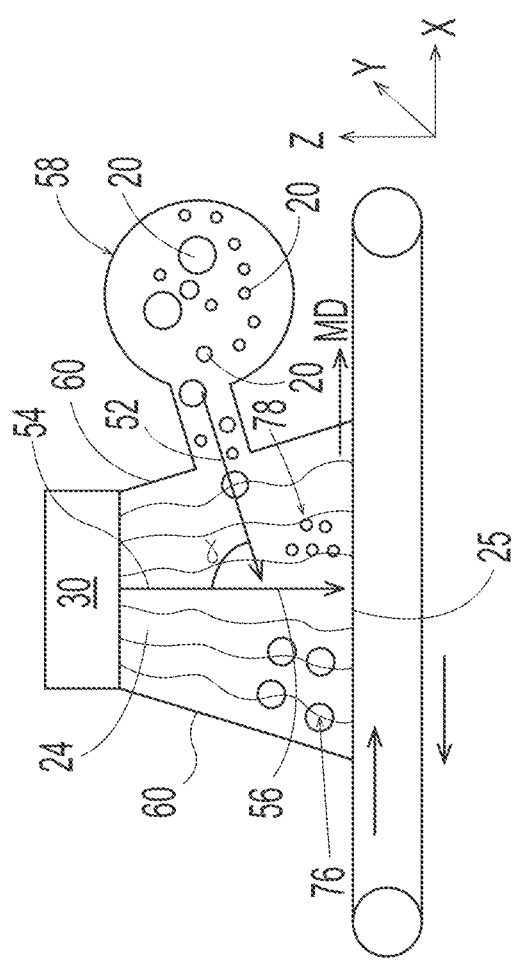
FIG. 11 is a schematic representation of an example of a process according to the present invention.

Some of the complexity in achieving the desired particle distribution is illustrated in FIG. 10 where a combination of fluid streams, for example air streams, to deliver fibrous elements, for example filaments 24 from a filament source 30, such as a die, and a particle fluid stream 52 (particle stream 52) comprising particles 20 is shown. The filament stream at the point of particle integration (particle fluid stream 52 mixing with the filaments 24) has a strong velocity profile, with the highest velocity in the center of the region of mixing, and lower on the upstream and downstream side of the center. The actual trajectory of each particle 20 injected by the nozzle 75, is a function of its Stokes Number. Each particle's 20 angular acceleration (i.e. how sharply the trajectory will bend towards the collection device) is then a function of the local air velocity. This results in a complex path of travel for the particles 20. In particular the larger Stokes Number particles 20 may accelerate towards the collection device in the upstream half of the mixing region. However if the velocity in the z-direction is higher than the surrounding air on the downstream side of the enclosure 60, it will decelerate in the z-direction creating an inflection point. Furthermore, physical constraints such as the presence of sidewalls of the enclosure 60 enclosing the region of mixing, may then result in larger particles bouncing on the downstream sidewall of the enclosure 60, resulting in larger particles being deposited further to the upstream side.

As shown in FIG. 11, the process of the present invention comprises the step of mixing a first fluid stream comprising a plurality of fibrous elements, for example a filament stream 54 comprising a plurality of filaments 24 with a second fluid stream comprising a plurality of first particles 20, for example a particle stream 52 such that a composite stream 56 exhibiting a non-random arrangement of the plurality of first particles 20 in the composite fluid stream 56 is formed. As shown in FIG. 11, the step of mixing occurs within an enclosure 60. The mixing may result the commingling of the filaments 24 and the particles 20, for example the step of mixing may be a coforming process. The mixing of the filament stream 54 with the particle stream 52 may occur at an angle α of from about 30° to about 120° and/or from about 45° to about 100° and/or from about 60° to about 90°. The particles 20 may exhibit a range of Stokes Numbers, for example a range of Stokes Numbers that exhibit at least a 50 unit difference and/or at least a 100 unit difference and/or at least a 150 unit difference and/or at least a 200 unit difference and/or at least a 250 unit difference. In one example, at least one particle 20 exhibits a size that is at least two times greater and/or at least three times greater than the size of at least one other particle 20. The introduction of the particle stream 52 may occur on the filament stream's upstream side and/or downstream side.

As shown in FIG. 11, in one example of the present invention, the mixing of the particles 20 with the filaments 24 results in a non-random arrangement of the particles 20 in the composite stream 56 based on a particle characteristic selected from the group consisting of: size, shape, mass, density, Stokes Number, and mixtures thereof. In one example, the particle characteristic is size. In one example, the non-random arrangement of the particles 20 in the composite stream 56 comprises a first group 76 of particles 20 comprising at least a majority of larger size particles 20 present in a first part of the composite stream's 56 machine direction thickness and a second group 78 of particles 20 comprising at least a majority of smaller size particles present in a second part of the composite stream's 56 machine direction thickness different from the first part. In one example, the first part of the composite stream's machine direction thickness is more proximate to the composite stream's 56 upstream side than the second part. In another example, the second part of the composite stream's 56 machine direction thickness is more proximate to the composite stream's 56 downstream side than the first part. In another example, the first part of the composite stream's 56 machine direction thickness is proximate to the composite stream's 56 upstream side and the second part of the composite stream's 56 machine direction thickness is proximate to the composite stream's 56 downstream side.

As shown in FIG. 11, in one example of the present invention, the mixing of the particles 20 with the filaments 24 results in a non-random arrangement of the particles 20 in the composite stream 56 based on Stokes Numbers of the particles 20. In one example, the non-random arrangement of the particles 20 in the composite stream 56 comprises a first group 76 of particles 20 comprising at least a majority of larger Stokes Number particles 20 present in a first part of the composite stream's 56 machine direction thickness and a second group 78 of particles 20 comprising at least a majority of smaller Stokes Number particles 20 present in a second part of the composite stream's 56 machine direction thickness different from the first part. In one example, the first part of the composite stream's 56 machine direction thickness is more proximate to the composite stream's 56 upstream side than the second part. In another example, the second part of the composite stream's 56 machine direction thickness is more proximate to the composite stream's 56 downstream side than the first part. In another example, the first part of the composite stream's 56 machine direction thickness is proximate to the composite stream's 56 upstream side and the second part of the composite stream's 56 machine direction thickness is proximate to the composite stream's 56 downstream side.

In another example, the non-random arrangement of the particles in the composite stream is such that the particles are present in a machine direction gradient in the composite stream based on a particle characteristic selected from the group consisting of: size, shape, mass, density, Stokes Number, and mixtures thereof. In one example, the particle characteristic is size. In another example the particle characteristic is Stokes Number. In one example, the machine direction gradient is a continuous gradient. In another example, the continuous gradient is present throughout the entire machine direction thickness of the composite stream. In another example, the machine direction gradient is present in less than the entire machine direction thickness of the composite stream.

a. Particles

The particle stream 52 may comprise less than 50% and/or less than 40% and/or less than 30% and/or less than 20% and/or less than 10% and/or less than 5% and/or less than 3% and/or 0% or about 0% by weight of non-particle solid additives, for example fibers, such as pulp fibers, for example wood pulp fibers.

The plurality of particles 20 of the particle stream 52 may exhibit a particle size distribution span of greater than 10% and/or greater than 15% and/or greater than 20% and/or greater than 25% and/or greater than 30% and/or greater than 35% and/or greater than 40% and/or greater than 45% and/or greater than 50%.

The plurality of particles 20 of the particle stream 52 may exhibit a range of Stokes Number, for example from about 50 to about 1000 and/or from about 80 to about 800 and/or from about 100 to about 600.

The plurality of particles 20 of the particle stream 52 may exhibit a Stokes Number difference of less that 1000 and/or less than 800 and/or less than 600 and/or less than 500 and/or less than 400.

The plurality of particles 20 of the particle stream 52 may exhibit a range of average volumes of from about 0.0001 mm$^3$ to about 0.001 mm$^3$ and/or from about 0.0002 mm$^3$ to about 0.0009 mm$^3$ and/or from about 0.0003 mm$^3$ to about 0.0009 mm$^3$ and/or from about 0.0005 mm$^3$ to about 0.0008 mm$^3$ and/or from about 0.0001 mm$^3$ to about 0.0008 mm$^3$ and/or from about 0.0001 mm$^3$ to about 0.0006 mm$^3$ as measured according to the μCT Test Method described herein.

The plurality of particles 20 of the particle stream 52 may exhibit an average volume difference of less than 0.001 mm$^3$ and/or less than 0.0008 mm$^3$ and/or less than 0.0006 mm$^3$ and/or less than 0.0005 mm$^3$ and/or less than 0.0004 mm$^3$ as measured according to the μCT Test Method described.

The plurality of particles 20 of the particle stream 52 may exhibit a range of densities of from about 0.1 g/cm$^3$ to about 2.5 g/cm$^3$ and/or from about 0.3 g/cm$^3$ to about 2.0 g/cm$^3$ and/or from about 0.5 g/cm$^3$ to about 2.0 g/cm$^3$ and/or from about 0.7 g/cm$^3$ to about 1.8 g/cm$^3$ and/or from about 0.8 g/cm$^3$ to about 1.8 g/cm$^3$ and/or from about 1.0 g/cm$^3$ to about 1.5 g/cm$^3$.

If the process comprises two or more particle streams 52 either in a single beam and/or in multiple beams, the particles 20 within the two or more particle streams 52 may be the same or different. In other words, the particles 20 within the two or more particle streams 52 may comprise different compositions and/or exhibit different densities and/or exhibit different particle characteristics, for example different particle characteristics selected from the group consisting of: size, shape, mass, density, Stokes Number, and mixtures thereof.

The plurality of particles 20 of the particle stream 52 may exhibit different shapes, for example regular and/or irregular shapes. In one example, the plurality of particles 20 exhibit different irregular shapes.

Figure 12:
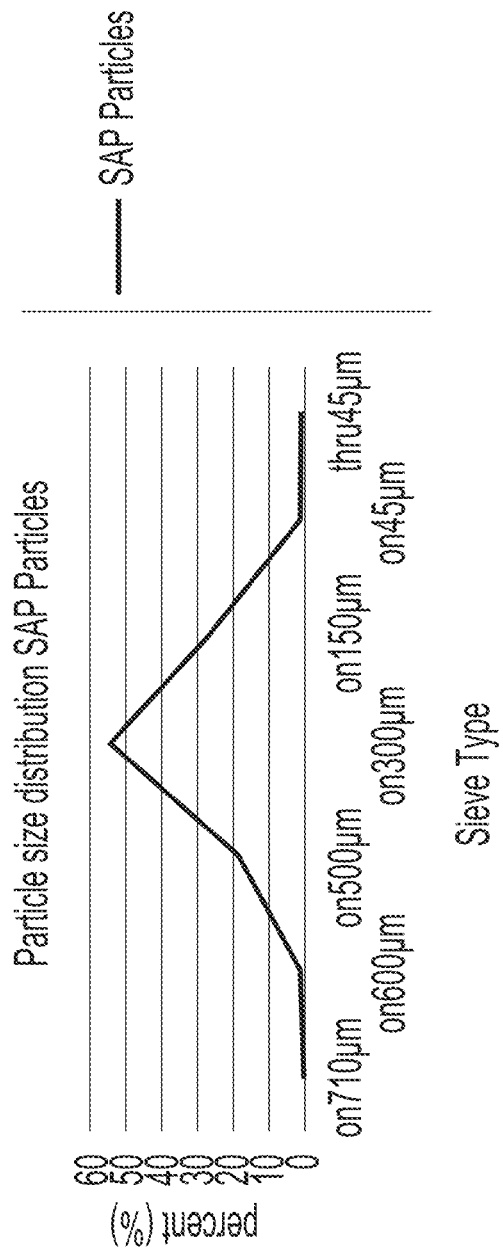
FIG. 12 is a particle size distribution profile of an example of a particle according to the present invention.

The plurality of particles 20 of the particle stream 52 may be derived from a particle material (not shown) that has been sieved, milled, and/or ground. FIG. 12 shows the Particle Size Distribution Profile of an example of a plurality of particles that have been sieved and have been measured according to the Particle Size Distribution Test Method described herein. In addition to the Particle Size Distribution Profile of FIG. 12, which shows that the plurality of particles 20 exhibit a D50 particle size of 300 μm, the plurality of particles 20 also exhibit the Stokes Numbers and Mass % Particle Sizes set forth below in Table 2.

TABLE 2

| Diameter (μm) | mass % of particle size | Stokes Number |
|---|---|---|
| 710 | 0.1 | 548 |
| 600 | 2.7 | 391 |
| 500 | 16.3 | 271 |
| 300 | 54.9 | 97 |
| 150 | 24.9 | 24 |
| 45 | 0.9 | 2 |

In addition, the particles of the present invention may further comprise tighter particle size distribution profiles such as are seen in colloidal SAP particles, which tend to be very spherical and exhibit a D50 of about 300 μm with a particle size range of from about 250 to 350 μm. Examples of such colloidal SAP particles are commercially available from Sumitomo.

The plurality of particles 20 of the particle stream 52 may comprise super absorbent polymer particles (SAP), perfume particles, abrasive particles, odor controlling particles, and mixtures thereof. In one example, the super absorbent polymer comprises carboxylic acid, for example crosslinked carboxylic acid.

The plurality of particles 20 of the particle stream 52 may comprise greater than 80% and/or greater than 90% and/or greater than 95% and/or about 100% and/or 100% by weight of super absorbent polymer particles.

The super absorbent polymer particles may exhibit particle sizes over a wide range. For reasons of industrial hygiene, average particle sizes smaller than about 30 microns are less desirable. Particles having a smallest dimension larger than about 2 mm may also cause a feeling of grittiness in the resulting structure, which is undesirable from a consumer aesthetics standpoint. Furthermore, rate of fluid absorption can be affected by particle size. Larger particles have very much reduced rates of absorption. In one example, super absorbent polymer particles have a particle size of from about 30 microns to about 2 mm for substantially all of the particles. "Particle Size" as used herein means the weighted average of the smallest dimension of the individual particles.

In one example, the plurality of particles exhibits a D50 particle size of from about 100 μm to about 5000 μm and/or from about 100 μm to about 2000 μm and/or from about 250 μm to about 1200 μm and/or from about 250 μm to about 850 μm as measured according to the Particle Size Distribution Test Method.

In one example, the plurality of particles are present in the structure at a basis weight of from about 10 gsm to about 1000 gsm.

In one example, the plurality of particles comprises first particles comprising a first composition and second particles comprising a second composition different from the first composition.

In one example, the plurality of particles comprises first particles exhibiting a first Stokes Number and second particles exhibiting a second Stokes Number different from the first Stokes Number, for example wherein the first Stokes Number is at least 20% and/or at least 30% different from the second Stokes Number.

b. Filaments

The filaments may comprise a polymer, for example a thermoplastic polymer, such as a thermoplastic polymer is selected from the group consisting of: polyolefins, polyesters, polyesteramides, polycaprolactones, polyhydroxyalkanoates, polylactic acids, and mixtures thereof. In one example, the thermoplastic polymer is a polyolefin, such as a polyolefin selected from the group consisting of: polypropylene, polypropylene copolymers, polyethylene, polyethylene copolymers, and mixtures thereof.

In one example, the thermoplastic polymer is a biodegradable thermoplastic polymer.

In one example, the thermoplastic polymer is a compostable thermoplastic polymer.

Non-limiting examples of suitable polypropylenes for making the filaments, for example filaments of the present invention are commercially available from LyondellBasell and Exxon-Mobil.

Any hydrophobic or non-hydrophilic materials within the coform fibrous structure, such as the thermoplastic filaments, for example the polypropylene filaments, may be surface treated and/or melt treated with a hydrophilic modifier. Non-limiting examples of surface treating hydrophilic modifiers include surfactants, such as Triton X-100. Non-limiting examples of melt treating hydrophilic modifiers that are added to the polymer composition (polymer melt), such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at any suitable level known in the art. In one example, the hydrophilic modifier is associated with the polymer composition, such as the hydrophobic and/or non-hydrophilic material within the polymer composition at a level of greater than 0% to less than about 20% and/or greater than 0% to less than about 15% and/or greater than 0.1% to less than about 10% and/or greater than 0.1% to less than about 5% and/or greater than 0.5% to less than about 3% by dry weight of the hydrophobic or non-hydrophilic material. In another example, the hydrophilic modifier may be present in the filaments at a level of from about 0.1% to about 10% and/or from about 0.5% to about 7% and/or from about 1% to about 5% by weight of the filaments.

c. Non-Particle Solid Additives

In one example, the non-particle solid additives of the present invention, for example fibers, such as pulp fibers, for example wood pulp fibers, may be selected from the group consisting of softwood kraft pulp fibers, hardwood pulp fibers, and mixtures thereof. Non-limiting examples of hardwood pulp fibers include fibers derived from a fiber source selected from the group consisting of: *Acacia*, *Eucalyptus*, Maple, Oak, Aspen, Birch, Cottonwood, Alder, Ash, Cherry, Elm, Hickory, Poplar, Gum, Walnut, Locust, Sycamore, Beech, *Catalpa, Sassafras, Gmelina, Albizia, Anthocephalus*, and *Magnolia*. Non-limiting examples of softwood pulp fibers include fibers derived from a fiber source selected from the group consisting of: Pine, Spruce, Fir, Tamarack, Hemlock, Cypress, and Cedar. In one example, the hardwood pulp fibers comprise tropical hardwood pulp fibers. Non-limiting examples of suitable tropical hardwood pulp fibers include *Eucalyptus* pulp fibers, *Acacia* pulp fibers, and mixtures thereof.

In one example, the wood pulp fibers comprise softwood pulp fibers derived from the kraft process and originating from southern climates, such as Southern Softwood Kraft (SSK) pulp fibers. In another example, the wood pulp fibers comprise softwood pulp fibers derived from the kraft process and originating from northern climates, such as Northern Softwood Kraft (NSK) pulp fibers.

The wood pulp fibers, when present in the process and/or structure of the present invention may be present at a weight ratio of softwood pulp fibers to hardwood pulp fibers of from 100:0 and/or from 90:10 and/or from 86:14 and/or from 80:20 and/or from 75:25 and/or from 70:30 and/or from 60:40 and/or about 50:50 and/or to 0:100 and/or to 10:90 and/or to 14:86 and/or to 20:80 and/or to 25:75 and/or to 30:70 and/or to 40:60. In one example, the weight ratio of softwood pulp fibers to hardwood pulp fibers is from 86:14 to 70:30.

In one example, the non-particle solid additives of the present invention comprise one or more trichomes. Non-limiting examples of suitable sources for obtaining trichomes, especially trichome fibers, are plants in the Labiatae (Lamiaceae) family commonly referred to as the mint family. Examples of suitable species in the Labiatae family include *Stachys byzantina*, also known as *Stachys lanata* commonly referred to as lamb's ear, woolly betony, or woundwort. The term *Stachys byzantina* as used herein also includes cultivars *Stachys byzantina* 'Primrose Heron', *Stachys byzantina* 'Helene von Stein' (sometimes referred to as *Stachys byzantina* 'Big Ears'), *Stachys byzantina* 'Cotton Boll', *Stachys byzantina* 'Variegated' (sometimes referred to as *Stachys byzantina* 'Striped Phantom'), and *Stachys byzantina* 'Silver Carpet'.

In another example, the non-particle solid additives of the present invention may comprise one or more super absorbent polymer fibers so long as the process and/or structure includes a plurality of particles according to the present invention.

d. Forming the Structure

To ultimately form the structures 26 of the present invention, the composite stream 56 comprising a plurality of filaments 24 and a plurality of particles 20 and optionally a plurality of non-particle solid additives 64 is collected on a collection device 25, for example a through-air-drying fabric or other fabric or a patterned molding member and/or a roller and/or a film and/or a pre-existing nonwoven web material, for example a top sheet, such as a secondary topsheet, which may be carried upon an additional collection device, such as a fabric. This step of collecting the composite stream 56 on the collection device 25 may comprise subjecting the resulting structure 26 while on the collection device 25 to a consolidation step whereby the structure 26, while present on the collection device 25, is pressed between a nip, for example a nip formed by a flat or even surface rubber roll and a flat or even surface or patterned, heated (with oil) or unheated metal roll.

The collection step onto the collection device may be vacuum assisted by a vacuum box under the collection device 25.

In one example, the filament source 30 of the process 50 may be meltblow die, for example a multi-row capillary die, a knife-edge die, and combinations thereof. In one example, the meltblown die is a multi-row capillary die. In one example, the multi-row capillary die comprises a plurality of filament-forming holes which is positioned coaxially within a fluid-releasing hole that provides attenuation air to the polymer exiting the filament-forming holes. The fluid-releasing hole may be concentrically or substantially concentrically positioned around the filament-forming hole. In one example, the fluid, for example attenuation air, exits one of more, for example each fluid-releasing hole parallel or substantially parallel to the filament exiting the one or more filament-forming holes.

In one example of the process 50 of the present invention, the process comprises the steps of:
a. providing a plurality of filaments;
b. providing a plurality of particles and optionally non-particle solid additives, wherein at least a portion of the plurality of solid additives comprises a plurality of particles, wherein the particles exhibit a broad range of particle size distribution; and
c. commingling the plurality of filaments with the plurality of solid additives;
d. collecting the commingled plurality of filaments and plurality of solid additives on a collection device to form a structure such that the plurality of particles are non-uniformly dispersed in the fibrous structure based upon their particle size.

In one example, the process comprises the steps of: a) providing a stream of filaments comprising a plurality of filaments, a stream of particles comprising a plurality of particles, for example a plurality of SAP particle, and optionally a stream of non-particle solid additives all streams being separate from one another and/or neat streams (for example less than 10% and/or less than 5% and/or less than 3% and/or about 0% and/or 0% by weight of material different from their respective materials); b) commingling the plurality of particles with the plurality of filaments; c) optionally commingling the plurality of non-particle solid additives with the plurality of filaments; d) collecting the filaments, particles, and optionally non-particle solid additives on a collection device to form a structure, such as a fibrous structure, for example an absorbent material, such as an absorbent core material.

In one example, the particles and non-particle solid additives, such as fibers, for example wood pulp fibers, may be introduced into the filament stream as a solid additive (particle and non-particle) stream. In such a case, the amount by weight of the non-particle solid additives may be relatively low compared to the amount by weight of the particles as described above. Further, the plurality of particles may exhibit at least one Stokes Number and the plurality of pulp fibers may exhibit at least one Stokes Number different from the at least one Stokes Number of the plurality of particles. In one example, at least one Stokes Number of the plurality of particles is at least 20% and/or at least 30% different from the at least one Stokes Number of the plurality of non-particle solid additives.

As described above, the step of commingling in the process may occur within an enclosure (housing), for example a forming box, such as a coforming box.

In one example, the step of commingling the plurality of filaments with the plurality of particles comprises introducing the plurality of particles into a stream of the plurality of filaments at an angle of from about 10° to about 170° and/or from about 20° to about 150° and/or from about 30° to about 130° and/or from about 30° to about 120° and/or from about 45° to about 100° and/or from about 60° to about 90° relative to the stream of the plurality of filaments.

In one example, the plurality of particles are non-uniformly distributed within the fibrous structure such that particles concentrated near one side of the fibrous structure exhibit a particle size that is at least two times the particle size of the particles concentrated near the opposite side of the fibrous structure. The plurality of particles may be non-uniformly distributed within the fibrous structure such that particles concentrated near one side of the fibrous structure exhibit a particle size that is at least three times the particle size of the particles concentrated near the opposite side of the fibrous structure.

In one example, the plurality of particles are non-uniformly distributed within the fibrous structure such that particles concentrated near a first third of the caliper of the fibrous structure exhibit a particle size that is at least two times the particle size of the particles concentrated near the opposite third of the caliper of the fibrous structure. The plurality of particles may be non-uniformly distributed within the fibrous structure such that particles concentrated near a first third of the caliper of the fibrous structure exhibit a particle size that is at least three times the particle size of the particles concentrated near the opposite third of the caliper of the fibrous structure.

Non-Limiting Process Examples for Making Structures of the Present Invention

Figure 13:
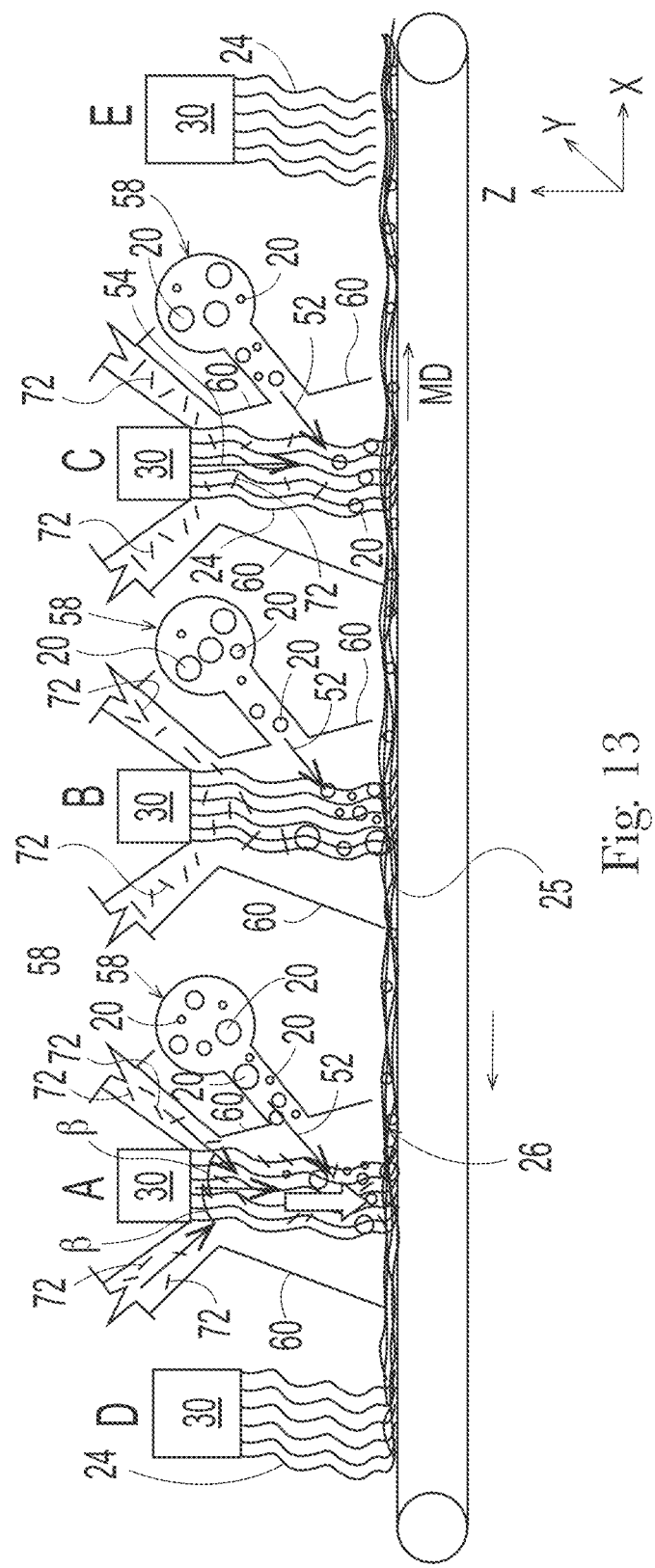
FIG. 13 is a schematic representation of an example of a process according to the present invention for use with Process Examples 1-6.

The following non-limiting examples, Process Examples 1-6, are made utilizing an example of a process 50 according to the present invention as shown in FIG. 13. FIG. 13 comprises multiple beams A-E, for example particle mixing beams A-C and scrim beams D-E. A given process may utilize one or more particle mixing beams A-C. Further, a given process may additionally use one or more scrim beams D-E. The various Process Examples 1-6 utilize different materials, different conditions, and/or different number of beams and/or configurations.

As shown in FIG. 13, the Process Examples 1-6 may utilize a single beam, two beams, three beams, and/or more, for example the beams may comprise simply a die to spin filaments onto the collection device and/or onto a surface of the particle-containing structure formed on the collection device or both, thus creating a scrim layer from the beam, which is referred to as a scrim beam.

For a multi-beam system, the following is defined: A series of beams, (beam A, beam B, beam C, etc.) with each beam letter defined by in which order it deposits material onto a collection device 25 (beam A lays down on naked collection belt or scrim layer riding on the collection belt or even on a pre-existing nonwoven web material riding on the collection belt, beam B lays down on material (for example fibrous structure) already deposited by beam A, beam C lays down material onto material already deposited by beam A and beam B.

Each beam integrates at least one or more different material classes,
Discrete short fibers=72 (e.g. semi-treated or fully treated pulp, EUC fibers, CS10 fibers, and mixtures thereof)
Continuous filaments=24 (e.g. meltblown fibers, such as PP, PE, other poly-olefins, PLA, PHA, block co-polymers, such as Vistamaxx)
Particles=20 (such as SAP, perfume microcapsules, odor controlling particles, abrasive particles). The particle delivery nozzle can be oriented in the CD on either the upstream or the downstream side of the beam and/or forming box (enclosure).

More than one nozzle can be installed in each beam, enabling combinations of particles and particle size, shape, mass, and/or Stokes Numbers gradients in machine direction thickness of composite stream and/or z-direction thickness of resulting fibrous structure produced by collecting the composite stream on the collection device 25. The nozzle can also be designed in such a way that only a section of the nozzle delivers particles, for example to create machine direction stripes in the resulting fibrous structure.

Each material 72, 24, and 20 in each beam, when present, can be controlled independently and can be the same or different material from one or more of the other beams. Each material can also be processed with different settings (angles, velocities e.g.). Also in a single beam, more than one type of particle can be delivered (injected).

Table 3 below sets forth an overview of the Process Examples 1a-6.

Process Examples Overview Table

| Example | Description | Utilization (problem solved) |
|---|---|---|
| 1a | Single beam, SAP particles concentrated in center layer, weak size gradient | Keep SAP particles away from surface for industrial hygiene, SAP utilization (less waste) and consumer safety |
| 1b | Single beam, SAP particles concentrated in center layer, SAP size gradient | Larger SAP particles towards top (consumer) for less gel blocking and better capillary gradient |
| 2 | Multi-beam, SAP particles size gradient and fiber size gradient, pulp type gradient | Spread liquid in x, y away from skin (small size, dryness) |
| 3 | Multibeam, low X-link SAP particles in surface layers, no SAP particles in center layer, use of pulp and fiber diameter to transport liquid from center to surface (pre-moisteded floor cleainig pad) | Large fluid holding capacity with effective fluid transfer to surface when cleaning (increase mileage of product) |
| 4 | Single beam depositing onto a pre-existing nonwoven web material such as a needlepunched, hydroentangled, air through bonded, spunbonded, carded resin bonded, and/or melt blown nonwoven web material. | Enables good hydraulic (fluid transport) continuity across the boundary between a Coformed fibrous structure and an adjacent Nonwoven Web Material as pulp fiber can interpenetrate minimizing liquid transport barriers for efficient liquid transport within an absorbent structure. |
| 5 | Dual beam with SAP particles integration from upstream side in first beam and downstream side in beam B | No grainy feel as larger SAP particles are primarily located in center layer. E.g. SAP particles with 0.6 mm (600 μm) diameter or greater will be noticeable against a user's skin, while SAP particles with 0.2 mm (200 μm) diameter or less will be much less noticeable against a user's skin. |
| 6 | Stripes of SAP particles in machine direction within fibrous structure. | Enable pads with SAP particles only in regions where needed (e.g. in center of pad) |

Process Example 1a (Low Basis Weight, 100 Gsm, Weak Size Gradient Distribution, No SAP Particles Close to Surface Regions—Localized Region of Particles):

Creation of a structure for intended use as absorbent system in hygienic disposable article, with approximately homogeneous size-distribution of SAP particles in z-direction. SAP is absent in the near-surface region to prevent SAP leaking from the material. A single beam in FIG. 13 is utilized for Process Example 1a. Optionally, one or more scrim beams may be utilized to produce a scrim on either or both sides of the structure formed by Process Example 1a. The details for Process Example 1a are set forth below in Table 4.

TABLE 4

| Beam | Beam A (bottom layer of product) ELN AW4841-1A | Beam B: Not used | Beam C: Not used |
|---|---|---|---|
| Material Class 72 (discrete fibers such as pulp) | Material: SSK semi-treated pulp (Golden Isle 4725). Process: Mass flow set to deliver 70 gsm to collection belt | | |
| Material Class 24 (continuous filaments such as melt-blown PP) | Material: PP blend: LB 650W PP 27.5% MFR 500 LB 650X PP 47.5% MFR 1200 Exxon 3155 MFR 35 20% Hydrofilic melt additive 5% Process: Spinning conditions set to deliver 30 gsm to collection belt, and air velocities set to deliver app 3.5 mm diameter (average). | | |
| Material Class 20 (particles such as SAP) | Material: Nippon Shokubai Co Ltd, Gr. L705/Nippon/ 90711868 (wide particle size distribution) Process: SAP federate adjusted to deliver 25 gsm on collection | | |

TABLE 4-continued

| Beam | Beam A (bottom layer of product) ELN AW4841-1A | Beam B: Not used | Beam C: Not used |
|---|---|---|---|
|  | belt. Nozzle in CD position at upstream side of beam, angled at 60-90 degrees, app 8 m/s air velocity | | |

Figure 14A:
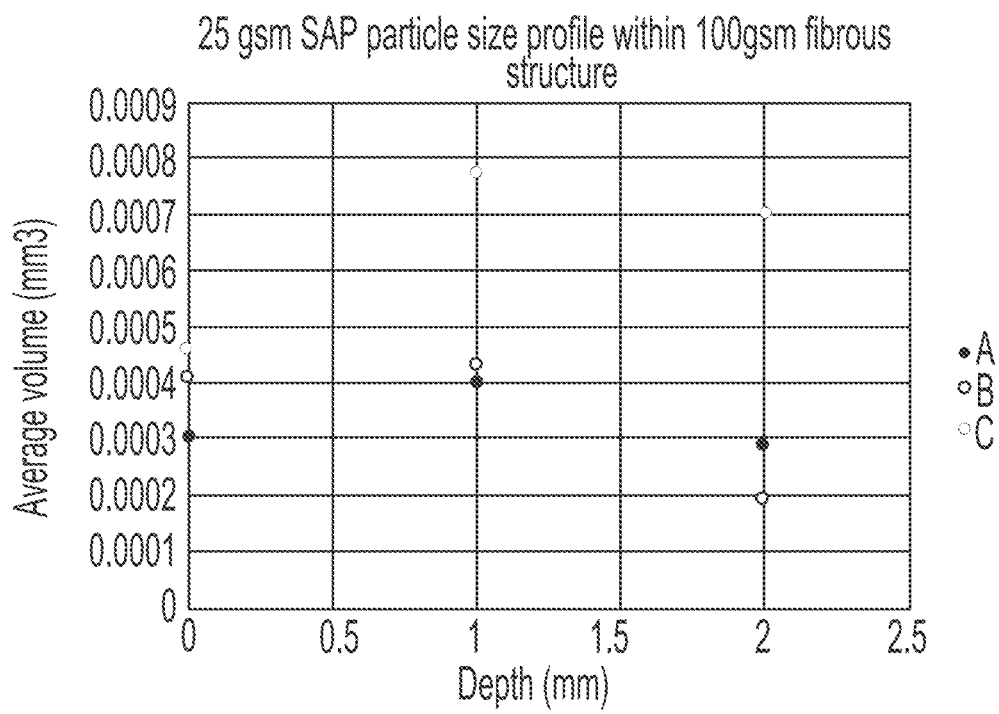
FIG. 14A is a graph of the SAP particle size distribution profile (x axis=Depth (mm) and y axis=Average Volume ($mm^3$)) of the fibrous structure made from Process Example 1a as measured according to the μCT Test Method described herein.
Figure 14B:
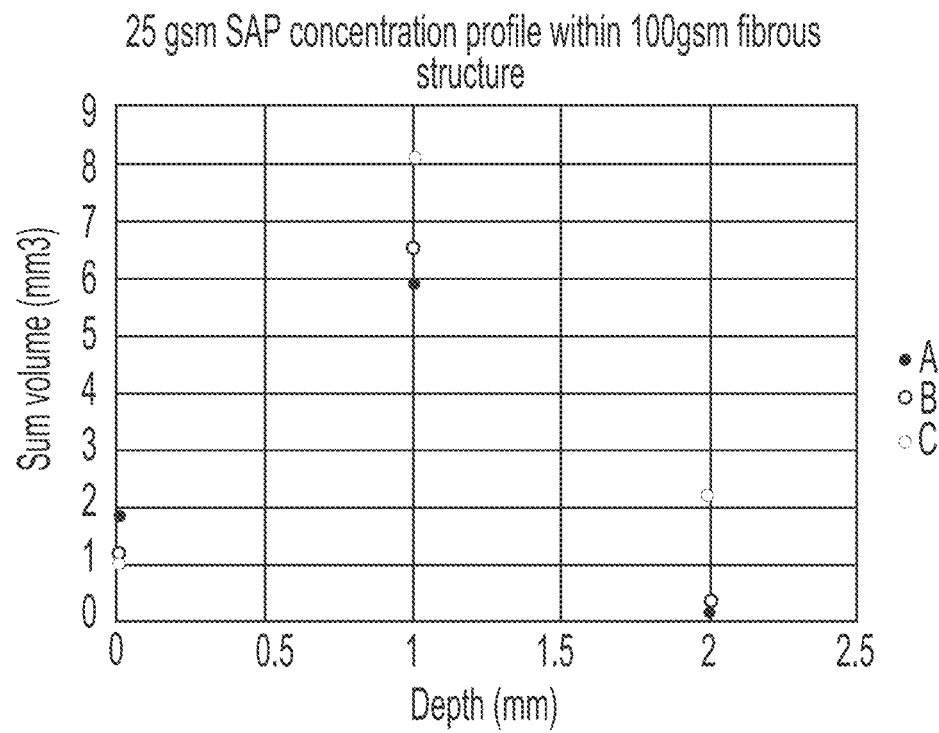
FIG. 14B is a graph of the SAP particle size distribution profile (x axis=Depth (mm) and y axis=Sum Volume ($mm^3$)) of the fibrous structure made from Process Example 1a as measured according to the μCT Test Method described herein.
Figure 14C:
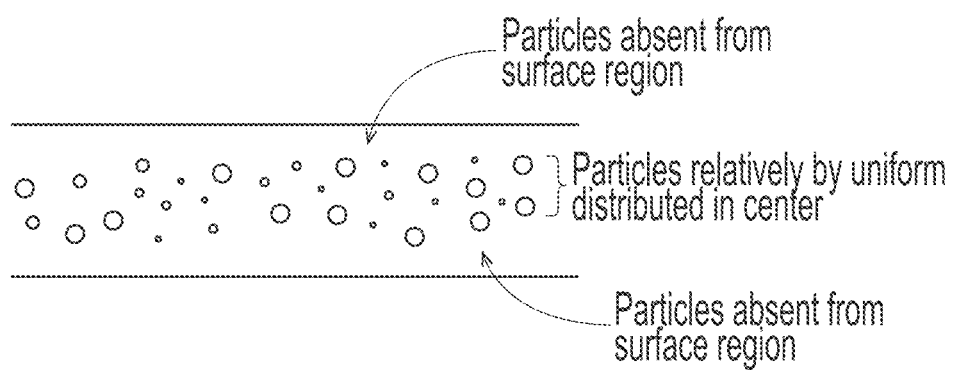

The structure formed by Process Example 1a exhibits a non-random arrangement of the particles in the fibrous structure formed as shown in FIGS. 14A, 14B, and 14C.

Process Example 1b (High Basis Weight, 200 Gsm, SAP Particle Size Gradient, Low Presence of SAP in Surface Regions):

Creation of a structure for intended use as absorbent system in hygienic disposable article, with larger SAP particles distributed towards the top of the material, and smaller SAP particles towards the bottom to prevent gel-blocking and better utilization of material. A single beam in FIG. 13 is utilized for Process Example 1b. Optionally, one or more scrim beams may be utilized to produce a scrim on either or both sides of the structure formed by Process Example 1b. The details for Process Example 1b are set forth below in Table 5.

TABLE 5

| Beam | Beam A (bottom layer of product) ELN AW4841-1A | Beam B: Not used | Beam C: Not used |
|---|---|---|---|
| Material Class 72 (discrete fibers such as pulp) | Material: SSK semi-treated pulp (Golden Isle 4725). Process: Mass flow set to deliver 140 gsm to collection belt | | |
| Material Class 24 (continuous filaments such as melt-blown PP) | Material: PP blend: LB 650W PP 27.5% MFR 500 LB 650X PP 47.5% MFR 1200 Exxon 3155 MFR 35 20% Hydrophilic melt additive 5% Process: Spinning conditions set to deliver 60 gsm to collection belt, and air velocities set to deliver app 3.5 mm diameter (average). | | |
| Material Class 20 (particles such as SAP) | Material: Nippon Shokubai Co Ltd, Gr. L705/Nippon/ 90711868 (wide particle size distribution) Process: SAP federate adjusted to deliver 80 gsm on collection belt. Nozzle in CD position at upstream side of beam, angled at 90-120 degrees, app 8 m/s air velocity | | |

Figure 15A:
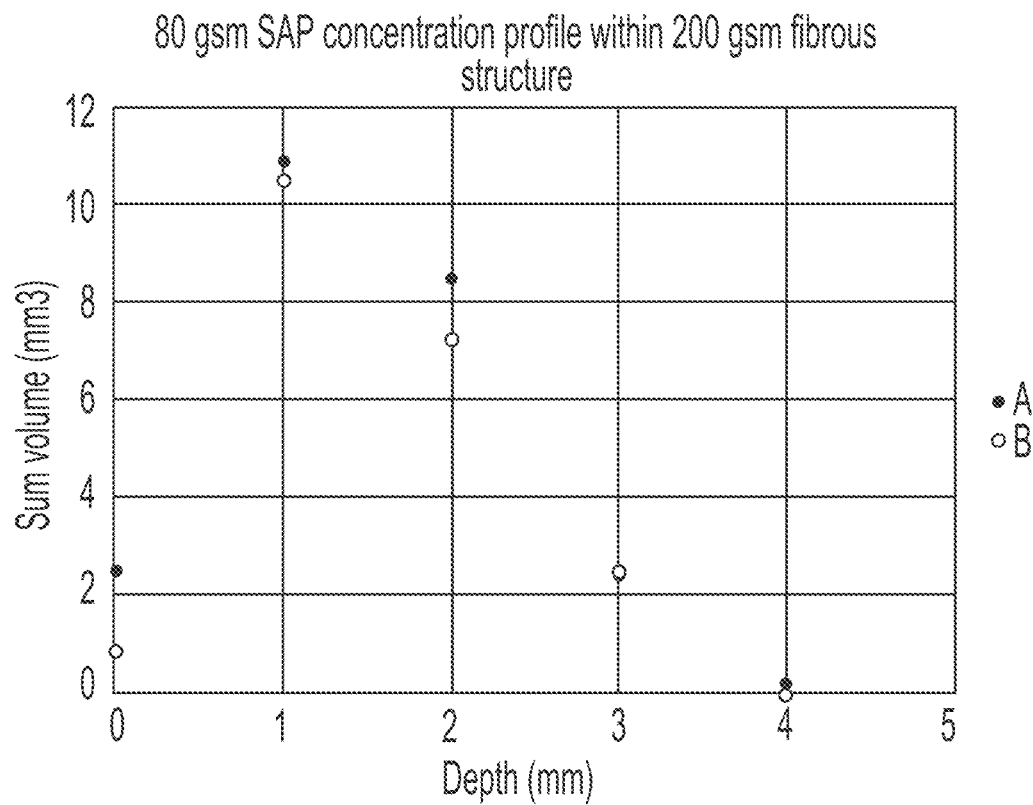
FIG. 15A is a graph of the SAP particle size distribution profile (x axis=Depth (mm) and y axis=Sum Volume ($mm^3$)) of the fibrous structure made from Process Example 1b as measured according to the μCT Test Method described herein.
Figure 15B:
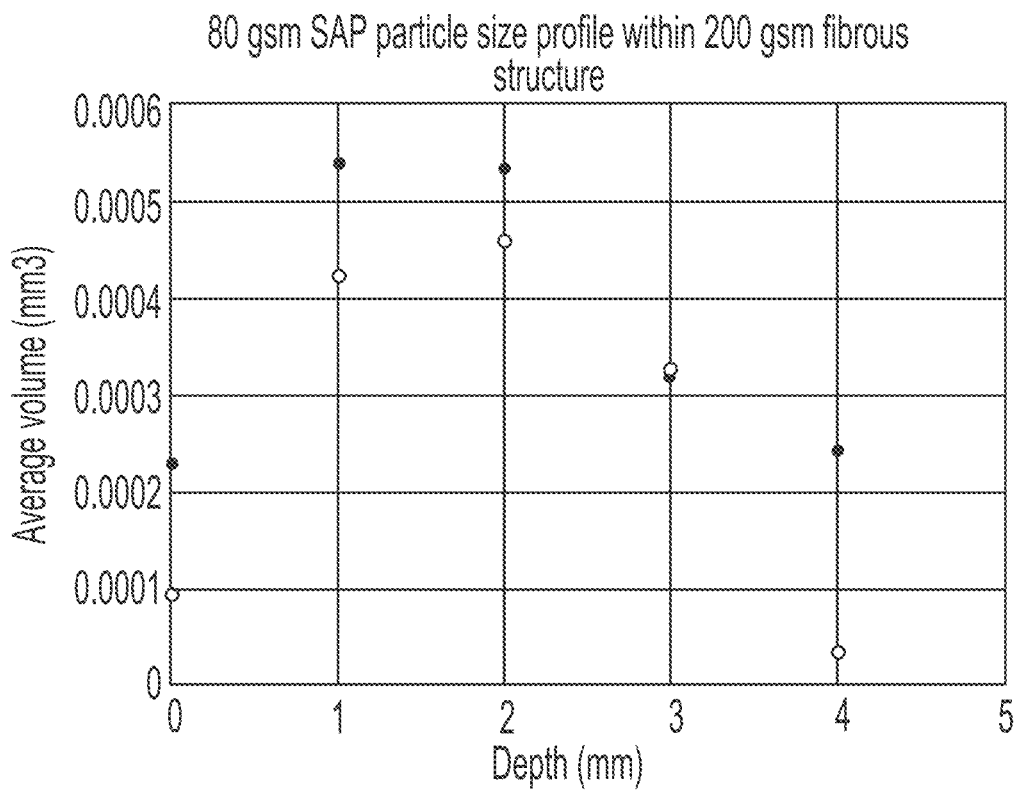
FIG. 15B is a graph of the SAP particle size distribution profile (x axis=Depth (mm) and y axis=Average Volume ($mm^3$)) of the fibrous structure made from Process Example 1b as measured according to the μCT Test Method described herein.

The structure formed by Process Example 1b exhibits a non-random arrangement of the particles in the fibrous structure formed as shown in FIGS. 15A, 15B, and 4C.

Process Example 2

Creation of a structure for intended use as absorbent system in hygienic disposable article, with efficient initial movement of liquid into material in z-direction, and spreading of liquid towards bottom of material away from skin. Multiple beams (three in this case) in FIG. 13 are utilized for Process Example 2. Optionally, one or more scrim beams may be utilized to produce a scrim on either or both sides of the structure formed by Process Example 2. The details for Process Example 2 are set forth below in Table 6.

TABLE 6

| Beam | A (bottom layer of product) | B (Middle layer of product) | C (top layer of product) |
|---|---|---|---|
| Material class 72 (discrete fibers such as pulp) | Small pulp fibers such as Eucalyptus, providing small PVD, high capillary suction, mass flow to deliver 35 gsm to collection belt | Standard pulp such as semi-treated SSK, mass flow to deliver 35 gsm to collection belt | Heavily treated cellulose fibers that resist wet collapse, such as CS10, mass flow to deliver 35 gsm to collection belt |
| Material class 24 (continuous filaments such as melt-blown PP) | PP blend with melt additive, spinning conditions to create thin filaments of 3-5 micrometer diameter, mass flow adjusted to deliver 15 gsm to collection belt | PP blend with melt additive, spinning conditions to create medium size filaments of 5-10 micrometers, mass flow adjusted to deliver 15 gsm to collection belt | PP blend with melt additive, spinning conditions to create thick fibers of 10-20 micrometer diameter, mass flow adjusted o deliver 15 gsm to collection belt |
| Material class 20 (particles such as SAP) | SAP with wide particle size distribution, nozzle in CD position at upstream side of beam, angled at 90-120 degrees, massflow adjusted to deliver 40 gsm to collection belt | SAP with more narrow particle size distribution, with high average particle size, nozzle in CD position at upstream side of beam, angled at 90-120 degrees, massflow adjusted to deliver 40 gsm to collection belt | No SAP introduced |

Resulting structure (modelled SAP size distribution) and exhibited a total basis weight of 150 gsm with 80 gsm SAP particles added).

Process Example 3

Creation of a structure for intended use as pre-moistened cleaning pad (for example a floor cleaning pad) for cleaning of floors and other hard surfaces. Cleaning pad to be usable on both sides, and with high capacity to store liquid at manufacturing and storage, and efficient release during product use. Liquid transport occurring from storage layer in center of pad to surface layers that are in contact with surface to be cleaned (e.g. floor). Multiple beams (three in this case) in FIG. 13 are utilized for Process Example 3. Optionally, one or more scrim beams may be utilized to produce a scrim on either or both sides of the structure formed by Process Example 3. The details for Process Example 3 are set forth below in Table 7.

TABLE 7

| Beam | A (bottom layer of product) | B (Middle layer of product) | C (top layer of product) |
|---|---|---|---|
| Material class 72 (discrete fibers such as pulp) | Small pulp fibers such as Eucalyptus, providing small PVD, high capillary suction | Standard pulp such as semi-treated SSK | Small pulp fibers such as Eucalyptus, providing small PVD, high capillary suction |
| Material class 24 (continuous filaments such as melt-blown PP) | PP blend with melt additive, spinning conditions to create thin filaments of 3-5 micrometer diameter | PP blend with melt additive, spinning conditions to create medium size filaments of 5-10 micrometers | PP blend with melt additive, spinning conditions to create thin filaments of 3-5 micrometer diameter |
| Material class 20 (particles such as SAP) | low X-link SAP with wide particle size distribution, nozzle in CD position at downstream side of beam, angled at 90-120 degrees. Smaller SAP particles are thus kept away from surface of product to prevent smearing | No SAP introduced | low X-link SAP with wide particle size distribution, nozzle in CD position at upstream side of beam, angled at 90-120 degrees. Smaller SAP particles are thus kept away from surface of product to prevent smearing |

Process Example 4

Creation of a structure for intended use as absorbent system in hygienic disposable article, where SAP with wide particle size distribution is used, where the smaller SAP particles are absent from the surface layer in order to prevent gel blocking, using a single beam. Single beam in FIG. 13 is utilized for Process Example 4. Optionally, one or more scrim beams may be utilized to produce a scrim on either or both sides of the structure formed by Process Example 4.

The process deposits the materials onto a pre-existing nonwoven web material, for example a topsheet, such as a 24 gsm carded nonwoven secondary topsheet from YanJan, riding on a collection device.

The details for Process Example 4 are set forth below in Table 8.

TABLE 8

| Beam | A (bottom layer of product) | B (Middle layer of product) | C (top layer of product) |
|---|---|---|---|
| Material class 72 (discrete fibers such as pulp) | Standard pulp such as semi-treated SSK | Not used | Not used |
| Material class 24 (continuous filaments such as melt-blown PP) | PP blend with melt additive, spinning conditions to create thin filaments of 5-10 micrometer diameter | Not used | Not used |
| Material class 20 (particles such as SAP) | SAP with wide particle size distribution, nozzle in CD position at upstream side of beam, angled at 70-110 degrees with high velocity air. Smaller SAP particles are thus kept away from zone close to surface of product to prevent gel blocking | Not used | Not used |

Example 5

Creation of a structure for intended use as absorbent system in hygienic disposable article, where SAP with wide particle size distribution is used, where the larger SAP particles are absent from the surface layer in order to prevent a grainy hard feel of the material by embedding the larger SAP particles in the middle of the fibrous structure. Multiple beams (two in this case) in FIG. 13 are utilized for Process Example 5. Optionally, one or more scrim beams may be utilized to produce a scrim on either or both sides of the structure formed by Process Example 5. The details for Process Example 5 are set forth below in Table 9.

TABLE 9

| Beam | A (bottom layer of product) | B (Middle layer of product) | C (top layer of product) |
|---|---|---|---|
| Material class 72 (discrete fibers such as pulp) | Standard pulp such as semi-treated SSK | Standard pulp such as semi-treated SSK | Not used |
| Material class 24 (continuous filaments such as melt-blown PP) | PP blend with melt additive, spinning conditions to create thin filaments of 5-10 micrometer diameter | PP blend with melt additive, spinning conditions to create thin filaments of 5-10 micrometer diameter | Not used |
| Material class 20 (particles such as SAP) | SAP with wide particle size distribution, nozzle in CD position at upstream side of beam, angled at 70-110 degrees with high velocity air (10-15 m/s). Smaller SAP particles are thus kept away from zone close to surface of product to prevent gel blocking | SAP with wide particle size distribution, nozzle in CD position at downstream side of beam, angled at 70-110 degrees with high velocity air (10-15 m/s). Smaller SAP particles are thus kept away from zone close to surface of product to prevent gel blocking | Not used |

Process Example 6

Creation of a structure for intended use as absorbent system in hygienic disposable article, where SAP is present only in a portion of the product (e.g. towards the center) to reduce cost of SAP material that does not contribute to product performance. Multiple beams (two in this case) in FIG. 13 are utilized for Process Example 6. Optionally, one or more scrim beams may be utilized to produce a scrim on either or both sides of the structure formed by Process Example 6. The details for Process Example 6 are set forth below in Table 10.

TABLE 10

| Beam | A (bottom layer of product) | B (Middle layer of product) | C (top layer of product) |
|---|---|---|---|
| Material class 72 (discrete fibers such as pulp) | Standard pulp such as semi-treated SSK | Standard pulp such as semi-treated SSK | Not used |
| Material class 24 (continuous filaments such as melt-blown PP) | PP blend with melt additive, spinning conditions to create thin filaments of 5-10 micrometer diameter | PP blend with melt additive, spinning conditions to create thin filaments of 5-10 micrometer diameter | Not used |
| Material class 20 (particles such as SAP) | SAP with wide particle size distribution, nozzle in CD position at downstream side of beam, with slots in nozzle depositing SAP on zones of app 50-70 mm width, separated by 50-70 mm zones absent of SAP | Not used | Not used |

Structures

The structures, for example fibrous structures, such as an absorbent material, for example an absorbent core material, of the present invention made by the inventive process of the present invention comprise a plurality of filaments and a plurality of particles. In one example, the plurality of filaments and the plurality of particles are commingled together to form a coform structure. In addition to the filaments and the particles, the structures of the present invention may further comprise a plurality of non-particle solid additives, such as fibers, for example pulp fibers, such as wood pulp fibers.

The structures, for example a fibrous structures, such as non-elastic fibrous structures, of the present invention comprise a plurality of filaments and a plurality of super absorbent polymer particles, and optionally a plurality of pulp fibers. The filaments and the super absorbent polymer particles, and optionally the pulp fibers, may be commingled together. In one example, the structure is a coform structure. The filaments may be present in the structures of the present invention at a level of less than 90% and/or less than 80% and/or less than 65% and/or less than 50% and/or greater than 5% and/or greater than 10% and/or greater than 20% and/or from about 10% to about 50% and/or from about 25% to about 45% by weight of the structure on a dry basis.

The particles may be present in the structures of the present invention at a level of greater than 10% and/or greater than 25% and/or greater than 50% and/or less than 100% and/or less than 95% and/or less than 90% and/or less than 85% and/or from about 30% to about 95% and/or from about 50% to about 85% by weight of the structure on a dry basis.

The non-particle solid additives, when present, may be present in the structures of the present invention at a level of greater than 10% and/or greater than 25% and/or greater than 50% and/or less than 100% and/or less than 95% and/or less than 90% and/or less than 85% and/or from about 30% to about 95% and/or from about 50% to about 85% by weight of the structure on a dry basis.

The filaments and particles may be present in the structures of the present invention at a weight ratio of filaments to particles of greater than 10:90 and/or greater than 20:80 and/or less than 90:10 and/or less than 80:20 and/or from about 25:75 to about 50:50 and/or from about 30:70 to about 45:55. In one example, the filaments and particles are present in the structures of the present invention at a weight ratio of filaments to particles of greater than 0 but less than 1.

The filaments and non-particle solid additives, when present, may be present in the structures of the present invention at a weight ratio of filaments to non-particle solid additives of greater than 10:90 and/or greater than 20:80 and/or less than 90:10 and/or less than 80:20 and/or from about 25:75 to about 50:50 and/or from about 30:70 to about 45:55. In one example, the filaments and non-particle solid additives, when present, are present in the structures of the present invention at a weight ratio of filaments to non-particle solid additives of greater than 0 but less than 1.

In one example, the structures of the present invention exhibit a basis weight of from about 10 gsm to about 1000 gsm and/or from about 10 gsm to about 500 gsm and/or from about 15 gsm to about 400 gsm and/or from about 15 gsm to about 300 gsm as measured according to the Basis Weight Test Method described herein. In another example, the structures of the present invention exhibit a basis weight of from about 10 gsm to about 200 gsm and/or from about 20 gsm to about 150 gsm and/or from about 25 gsm to about 125 gsm and/or from about 30 gsm to about 100 gsm and/or from about 30 gsm to about 80 gsm as measured according to the Basis Weight Test Method described herein. In still another example, the structures of the present invention exhibit a basis weight of from about 80 gsm to about 1000 gsm and/or from about 125 gsm to about 800 gsm and/or from about 150 gsm to about 500 gsm and/or from about 150 gsm to about 300 gsm as measured according to the Basis Weight Test Method described herein.

In one example the structure of the present invention is a coform fibrous structure, for example a non-elastic coform fibrous structure, comprises a core component comprising a plurality of particles, such as SAP particles, and optionally non-particle solid additives, for example fibers, such as pulp fibers, for example wood pulp fibers, and a plurality of core filaments, that are commingled with the particles and the non-particle solid additives, when present. The coform fibrous structure may further comprise a scrim component, which may be void or substantially void of particles and non-particle solid additives, comprising a plurality of scrim filaments, which may be the same and/or different for example in chemical composition as the core filaments and which are deposited, for example spun, directly onto one or more surfaces of the core component. The scrim component, for example the scrim filaments, may be bonded, for example thermally bonded, to the core component, for example the core component filaments and/or particles and/or non-particle solid additives, when present.

In one example, the core component is the component that exhibits the greatest basis weight within the coform fibrous structure. In one example, the core component present in the coform fibrous structure of the present invention exhibits a basis weight that is greater than 50% and/or greater than 55% and/or greater than 60% and/or greater than 65% and/or greater than 70% and/or less than 100% and/or less than 95% and/or less than 90% of the total basis weight of the coform fibrous structure as measured according to the Basis Weight Test Method described herein. In another example, the core component exhibits a basis weight of less than 20 gsm and/or less than 15 gsm and/or less than 12 gsm and/or less than 10 gsm and/or less than 8 gsm and/or less than 6 gsm and/or greater than 2 gsm and/or greater than 4 gsm as measured according to the Basis Weight Test Method described herein.

In one example, at least one of the core components of the coform fibrous structure comprises a plurality of non-particle solid additives, for example pulp fibers, such as comprise wood pulp fibers and/or non-wood pulp fibers.

In one example, the scrim component exhibits a basis weight that is less than 25% and/or less than 20% and/or less than 15% and/or less than 10% and/or less than 7% and/or less than 5% and/or greater than 0% and/or greater than 1% of the total basis weight of the coform fibrous structure as measured according to the Basis Weight Test Method described herein. In another example, the scrim component exhibits a basis weight of 10 gsm or less and/or less than 10 gsm and/or less than 8 gsm and/or less than 6 gsm and/or greater than 5 gsm and/or less than 4 gsm and/or greater than 0 gsm and/or greater than 1 gsm as measured according to the Basis Weight Test Method described herein.

In one example, at least one scrim component is adjacent to at least one core component within the coform fibrous structure. In another example, at least one core component is positioned between two scrim components within the coform fibrous structure.

In one example, at least one of the scrim filaments exhibits an average fiber diameter of less than 50 and/or less than 25 and/or less than 10 and/or at least 1 and/or greater than 1 and/or greater than 3 µm as measured according to the Average Diameter Test Method described herein.

The average fiber diameter of the core filaments is less than 250 and/or less than 200 and/or less than 150 and/or less than 100 and/or less than 50 and/or less than 30 and/or less than 25 and/or less than 10 and/or greater than 1 and/or greater than 3 µm as measured according to the Average Diameter Test Method described herein.

In one example, the coform fibrous structures of the present invention may comprise any suitable amount of filaments (core filaments and/or scrim filaments) and any suitable amount of solid additives. For example, the coform fibrous structures may comprise from about 10% to about 70% and/or from about 20% to about 60% and/or from about 30% to about 50% by dry weight of the coform fibrous structure of filaments and from about 90% to about 30% and/or from about 80% to about 40% and/or from about 70% to about 50% by dry weight of the coform fibrous structure of solid additives, such as wood pulp fibers.

In one example, the filaments and particles of the present invention may be present in the coform fibrous structures according to the present invention at weight ratios of filaments to particles of from at least about 1:1 and/or at least about 1:1.5 and/or at least about 1:2 and/or at least about 1:2.5 and/or at least about 1:3 and/or at least about 1:4 and/or at least about 1:5 and/or at least about 1:7 and/or at least about 1:10.

In one example, the non-particle solid additives, when present in the coform fibrous structure may be present in the coform fibrous structures according to the present invention at weight ratios of filaments to non-particle solid additives of from at least about 1:1 and/or at least about 1:1.5 and/or at least about 1:2 and/or at least about 1:2.5 and/or at least about 1:3 and/or at least about 1:4 and/or at least about 1:5 and/or at least about 1:7 and/or at least about 1:10.

In one example, the non-particle solid additives, for example fibers, such as pulp fibers, for example wood pulp fibers, may be selected from the group consisting of softwood kraft pulp fibers, hardwood pulp fibers, and mixtures thereof. Non-limiting examples of hardwood pulp fibers include fibers derived from a fiber source selected from the group consisting of: *Acacia, Eucalyptus*, Maple, Oak, Aspen, Birch, Cottonwood, Alder, Ash, Cherry, Elm, Hickory, Poplar, Gum, Walnut, Locust, Sycamore, Beech, *Catalpa, Sassafras, Gmelina, Albizia, Anthocephalus*, and *Magnolia*. Non-limiting examples of softwood pulp fibers include fibers derived from a fiber source selected from the group consisting of: Pine, Spruce, Fir, Tamarack, Hemlock, Cypress, and Cedar. In one example, the hardwood pulp fibers comprise tropical hardwood pulp fibers. Non-limiting examples of suitable tropical hardwood pulp fibers include *Eucalyptus* pulp fibers, *Acacia* pulp fibers, and mixtures thereof.

In one example, the wood pulp fibers comprise softwood pulp fibers derived from the kraft process and originating from southern climates, such as Southern Softwood Kraft (SSK) pulp fibers. In another example, the wood pulp fibers comprise softwood pulp fibers derived from the kraft process and originating from northern climates, such as Northern Softwood Kraft (NSK) pulp fibers.

The wood pulp fibers present in the coform fibrous structure may be present at a weight ratio of softwood pulp fibers to hardwood pulp fibers of from 100:0 and/or from 90:10 and/or from 86:14 and/or from 80:20 and/or from 75:25 and/or from 70:30 and/or from 60:40 and/or about 50:50 and/or to 0:100 and/or to 10:90 and/or to 14:86 and/or to 20:80 and/or to 25:75 and/or to 30:70 and/or to 40:60. In one example, the weight ratio of softwood pulp fibers to hardwood pulp fibers is from 86:14 to 70:30.

In one example, the fibrous structures of the present invention comprise one or more trichomes. Non-limiting examples of suitable sources for obtaining trichomes, especially trichome fibers, are plants in the Labiatae (Lamiaceae)

family commonly referred to as the mint family. Examples of suitable species in the Labiatae family include *Stachys byzantina*, also known as *Stachys lanata* commonly referred to as lamb's ear, woolly betony, or woundwort. The term *Stachys byzantina* as used herein also includes cultivars *Stachys byzantina* 'Primrose Heron', *Stachys byzantina* 'Helene von Stein' (sometimes referred to as *Stachys byzantina* 'Big Ears'), *Stachys byzantina* 'Cotton Boll', *Stachys byzantina* 'Variegated' (sometimes referred to as *Stachys byzantina* 'Striped Phantom'), and *Stachys byzantina* 'Silver Carpet'.

Non-limiting examples of suitable polypropylenes for making the filaments, for example filaments of the present invention are commercially available from LyondellBasell and Exxon-Mobil.

Any hydrophobic or non-hydrophilic materials within the coform fibrous structure, such as the thermoplastic filaments, for example the polypropylene filaments, may be surface treated and/or melt treated with a hydrophilic modifier. Non-limiting examples of surface treating hydrophilic modifiers include surfactants, such as Triton X-100. Non-limiting examples of melt treating hydrophilic modifiers that are added to the polymer composition (polymer melt), such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at any suitable level known in the art. In one example, the hydrophilic modifier is associated with the polymer composition, such as the hydrophobic and/or non-hydrophilic material within the polymer composition at a level of greater than 0% to less than about 20% and/or greater than 0% to less than about 15% and/or greater than 0.1% to less than about 10% and/or greater than 0.1% to less than about 5% and/or greater than 0.5% to less than about 3% by dry weight of the hydrophobic or non-hydrophilic material. In another example, the hydrophilic modifier may be present in the filaments at a level of from about 0.1% to about 10% and/or from about 0.5% to about 7% and/or from about 1% to about 5% by weight of the filaments.

In one example, a fibrous structure according to the present invention comprises a plurality of filaments and a plurality of solid particles wherein the plurality of filaments and the plurality of solid particles are commingled together to form the fibrous structure such that the plurality of solid particles are present through the fibrous structure's thickness at different average particle size values.

The plurality of filaments may comprise a plurality of filaments, for example water-insoluble filaments.

The plurality of filaments may comprise a plurality of fibers, for example water-insoluble fibers.

The filaments may comprise a polymer, for example a thermoplastic polymer, such as a thermoplastic polymer is selected from the group consisting of: polyolefins, polyesteramides, polycaprolactones, polyhydroxyalkanoates, polylactic acids, and mixtures thereof. In one example, the thermoplastic polymer is a polyolefin, such as a polyolefin selected from the group consisting of: polypropylene, polypropylene copolymers, polyethylene, polyethylene copolymers, and mixtures thereof.

In one example, the thermoplastic polymer is a biodegradable thermoplastic polymer.

In one example, the thermoplastic polymer is a compostable thermoplastic polymer.

In one example, the fibrous structure comprises a plurality of particles selected from the group consisting of: inorganic particles, organic particles, and mixtures thereof.

In one example, the fibrous structure comprises a plurality of solid particles comprising odor controlling particles and/or perfume particles, and/or abrasive particles.

In one example, the SAP particles of the fibrous structure comprise absorbent material particles, for example absorbent material particles comprising a superabsorbent polymer particles, such as carboxylic acid, for example crosslinked carboxylic acid.

In one example, the SAP particles exhibit a D50 particle size of from about 20 μm to about 2000 μm and/or from about 50 μm to about 2000 μm and/or from about 100 μm to about 2000 μm and/or from about 250 μm to about 1200 μm and/or from about 250 μm to about 850 μm and/or from about 150 μm to about 850 μm and/or from about 100 μm to about 600 μm and/or from about 100 μm to about 400 μm as measured according to the Particle Size Distribution Test Method.

In one example, the SAP particles are present in the fibrous structure at a basis weight of from about 10 gsm to about 1000 gsm.

The fibrous structure of the present invention may comprise a first group of solid particles comprising a first composition, such as the SAP particles, and second group of solid particles comprising a second composition different from the first composition.

In one example, the SAP particles comprise a first group of SAP particles that exhibit a first Stokes Number and second group of SAP particles that exhibit a second Stokes Number different from the first Stokes Number. In one example, the first Stokes Number is at least 20% and/or at least 30% different from the second Stokes Number.

The plurality of SAP particles may be present in the fibrous structure's thickness in an average particle size value gradient.

The plurality of solid particles may be present in the fibrous structure's thickness in an average particle size value continuous gradient The fibrous structure may further comprise a plurality of pulp fibers commingled together with the plurality of filaments and the plurality of SAP particles.

The plurality of pulp fibers may comprise wood pulp fibers.

The plurality of pulp fibers may comprise non-wood pulp fibers.

In one example, the particles are added in the process such that the resulting structure, for example fibrous structure, comprises a non-uniform concentration of the particles in the fibrous structure's z-direction.

In one example, the particles are added in the process such that the resulting structure, for example fibrous structure, comprises a first region comprising particles that exhibit a first particle size and a second region different from the first region comprising particles that exhibit a second particle size different from the first particle size.

Figure 16:
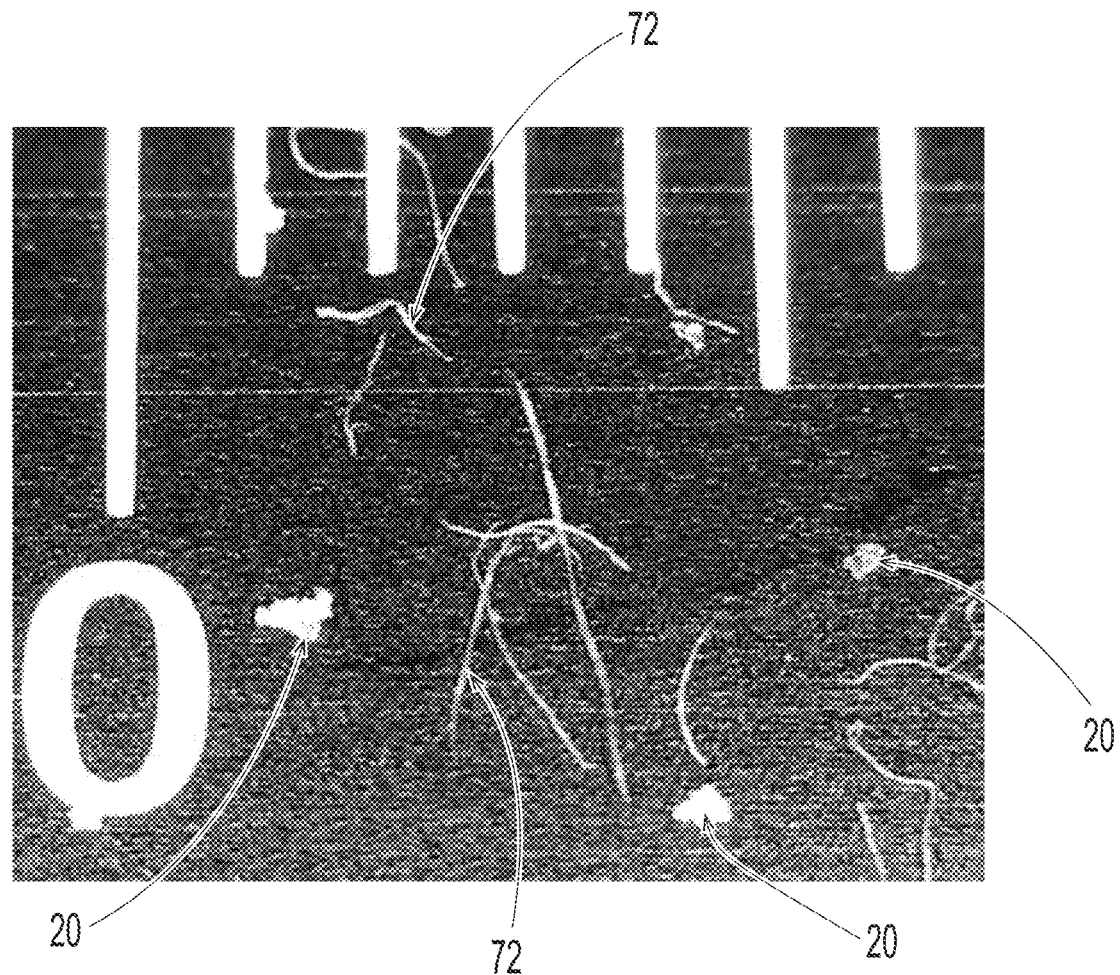
FIG. 16 is a magnified image of a portion of a ruler showing SAP particles and pulp fibers.
Figure 17A:
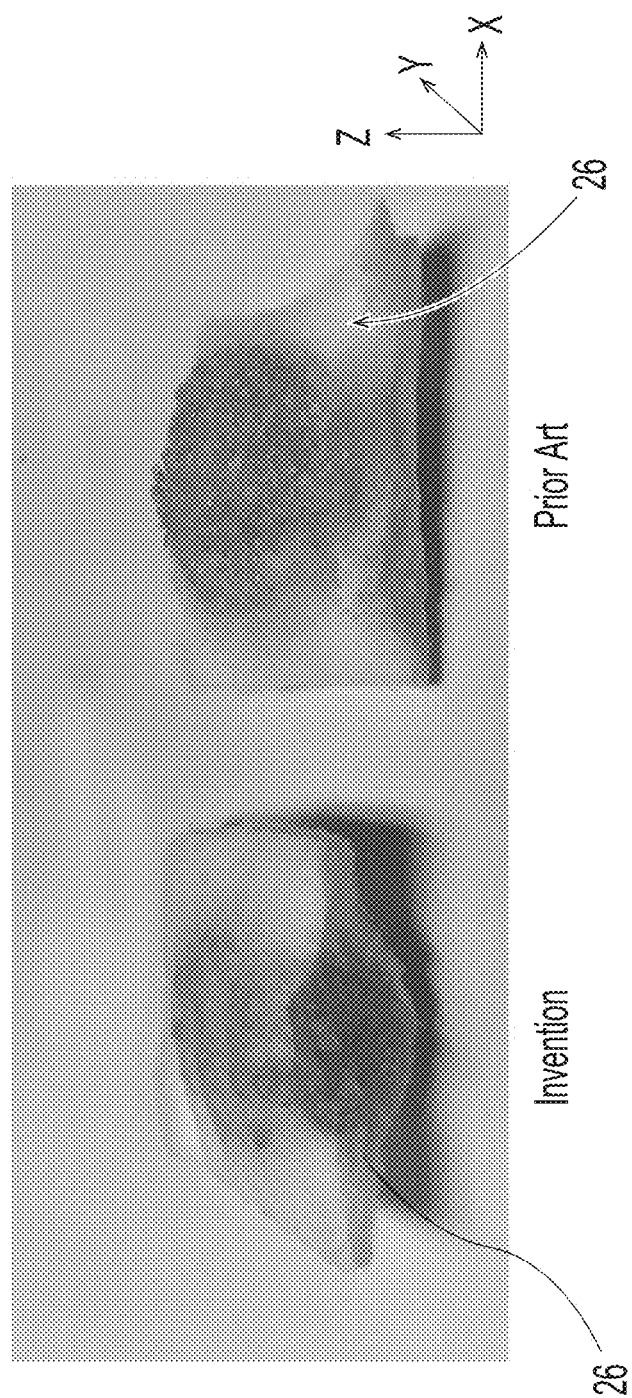
FIG. 17A is an image showing a fibrous structure made according to the present invention on the left side, which shows larger SAP (AGM) particles closer to the top (less or no small SAP particles near top), which prevents less gel blocking, compared to a comparative fibrous structure on the right side, which shows much more smaller SAP (AGM) particles closer to the top, which creates gel blocking during liquid absorption from the top.
Figure 17B:
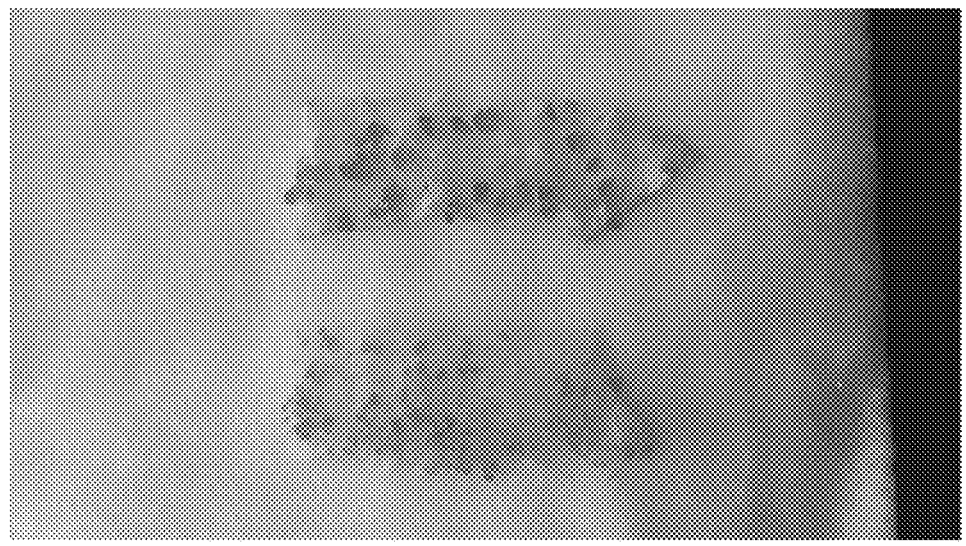
FIG. 17B is an image showing a tape stripped portion from the top (T) of the fibrous structure on the left side in FIG. 17A (inventive fibrous structure) and an image showing a tape stripped portion from the bottom (B) of the fibrous structure on the left side in FIG. 17A (inventive fibrous structure).

FIG. 16 shows non-limiting examples of particles 20, for example SAP particles, and non-particle solid additives, for example pulp fibers 72. As can be seen from FIG. 16, one reason for SAP particles having a larger stokes number is their larger geometric mean of major and minor axis vs pulp fibers.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 24 hours prior to the test. These will be considered standard conditioning temperature and humidity. All plastic and paper board packaging articles of manufacture, if any, must be carefully removed from the samples prior to testing. Except where noted all tests are conducted in such conditioned room, under the same environmental conditions in such conditioned room. Discard any damaged product. Do not test samples that have defects such as wrinkles, tears, holes, and like. All instruments are calibrated according to manufacturer's specifications. The stated number of replicate samples to be tested is the minimum number.

Basis Weight Test Method

Basis weight of a structure, such as a fibrous structure, for example an absorbent material, such as an absorbent core material is measured on stacks of eight to twelve structures using a top loading analytical balance with a resolution of ±0.001 g. A precision cutting die, measuring 8.890 cm by 8.890 cm or 10.16 cm by 10.16 cm is used to prepare all samples.

Condition samples under the standard conditioning temperature and humidity for a minimum of 10 minutes prior to cutting the sample. With a precision cutting die, cut the samples into squares. Combine the cut squares to form a stack eight to twelve samples thick. Measure the mass of the sample stack and record the result to the nearest 0.001 g.

Calculations:

$$\text{Basis Weight, g/m}^2 = \frac{\text{mass of stack}}{(\text{area of 1 square in stack})(\text{\# squares in stack})}$$

Report result to the nearest 0.1 g/m². Sample dimensions can be changed or varied using a similar precision cutter as mentioned above, so as at least 645 square centimeters of sample area is in the stack.

Individual fibrous structures that are ultimately combined to form and article may be collected during their respective making operation prior to combining with other fibrous structures and then the basis weight of the respective fibrous structure is measured as outlined above.

Average Diameter Test Method

There are many ways to measure the diameter of a fibrous element, for example a filament and/or fiber. One way is by optical measurement. A fibrous structure comprising fibrous elements, for example filaments, is cut into a rectangular shape sample, approximately 20 mm by 35 mm. The sample is then coated using a SEM sputter coater (EMS Inc, PA, USA) or equivalent with gold so as to make the filaments relatively opaque. Typical coating thickness is between 50 and 250 nm. The sample is then mounted between two standard microscope slides and compressed together using small binder clips. The sample is imaged using a 10× objective on an Olympus BHS microscope or equivalent with the microscope light-collimating lens moved as far from the objective lens as possible. Images are captured using a Nikon D1 digital camera or equivalent. A glass microscope micrometer is used to calibrate the spatial distances of the images. The approximate resolution of the images is 1 µm/pixel. Images will typically show a distinct bimodal distribution in the intensity histogram corresponding to the filaments and the background. Camera adjustments or different basis weights are used to achieve an acceptable bimodal distribution. Typically 10 images per sample are taken and the image analysis results averaged.

The images are analyzed in a similar manner to that described by B. Pourdeyhimi, R. and R. Dent in "Measuring fiber diameter distribution in nonwovens" (Textile Res. J. 69(4) 233-236, 1999). Digital images are analyzed by computer using the MATLAB (Version. 6.1) or equivalent and the MATLAB Image Processing Tool Box (Version 3) or equivalent. The image is first converted into a grayscale. The image is then binarized into black and white pixels using a threshold value that minimizes the intraclass variance of the thresholded black and white pixels. Once the image has been binarized, the image is skeletonized to locate the center of each fiber in the image. The distance transform of the binarized image is also computed. The scalar product of the skeletonized image and the distance map provides an image whose pixel intensity is either zero or the radius of the fiber at that location. Pixels within one radius of the junction between two overlapping fibers are not counted if the distance they represent is smaller than the radius of the junction. The remaining pixels are then used to compute a length-weighted histogram of filament diameters contained in the image.

Micro-CT (µCT) Test Method 3D x-ray sample imaging is obtained on a micro-CT instrument such as the Scanco µCT 50 or Scanco µCT 100HE (Scanco Medical AG, Switzerland). The micro-CT instrument is a cone beam microtomograph with a shielded cabinet. A maintenance-free x-ray tube is used as the source with an adjustable focal spot diameter. The x-ray beam passes through the sample, where some of the x-rays are attenuated based on the sample composition, structure and total volume. In other words, the extent of attenuation correlates to the mass density of the sample the x-rays pass through. The transmitted/attenuated x-rays continue to the digital detector array and generate a 2D projection image of the sample. A 3D image of the sample is generated by collecting hundreds of individual 2D projections at different directional angles as the sample is rotated. These direction dependent 2D projections are then reconstructed into a single 3D image. The instrument is interfaced with a computer running software to control the image acquisition and save the raw data.

Micro-Computed for Determining Average Particle Size Distributions with Fibrous Structures (FS):

Porosity is the ratio between void-space to the total space occupied by a fibrous structure. Porosity under this test method is calculated from µCT scans of a fibrous structure by segmenting the void space via thresholding and determining the ratio of void voxels to total voxels. Similarly, solid volume fraction (SVF) is calculated from µCT scans of a fibrous structure and is the ratio between solid space to the total space, and SVF is calculated as the ratio of solid voxels to total voxels. Both Porosity and SVF are an average scalar-value that do not provide structural information, different from, "pore-size distribution" in the height-direction of the fibrous structure, or the "average thickness of fibrous structure fibers" in the machine direction (MD) or "particle (for example SAP particle) size distribution" as a function of fibrous structure depth.

To characterize the 3D structure of the fibrous structure, samples are imaged using a µCT X-ray scanning instrument capable of acquiring a dataset at high isotropic spatial resolution. One example of suitable instrumentation is the SCANCO system model 50 µCT scanner or 100HE µCT (Scanco Medical AG, Brüttisellen, Switzerland) operated with the following settings: energy level of 45 kVp at 104

µA; 3000 projections; 19 mm field of view; 400 ms integration time; an averaging of 6; and a voxel size of 6 µm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned fibrous structure samples are normally prepared by punching a core of approximately 32 mm in diameter from the fibrous structure to be scanned. The fibrous structure punch is laid flat on a low-attenuating foam and then mounted in a 34 mm diameter plastic cylindrical tube for scanning. Scans of the fibrous structure punch samples are acquired such that a 19 mm inner volume is included in the dataset as to avoid structural modifications from the edge while punching-out the sample. From this dataset, a smaller sub-volume of the sample dataset is extracted from the total cross section of the scanned fibrous structure punch, creating a 3D slab of data, where the fibrous structure can be qualitatively assessed, accurately and promptly.

To characterize particle, for example SAP particle distribution, the particle, for example SAP particle must be separated from the fibrous structure. This was easily accomplished by thresholding and segmentation. The particle, for example SAP particle has a higher mass density than that of the surrounding fibrous elements, thus a high threshold is implemented to separate particle components from the fibrous structure, for example fibrous elements. To then characterize particle distribution in the height-direction, Local Thickness Map algorithm, or LTM, was implemented on the subvolume dataset. The LTM Method starts with a Euclidean Distance Mapping (EDM) which assigns grey level values equal to the distance each solid-voxel is from its nearest boundary. Based on the EDM data, the 3D solid space representing particle is tessellated with spheres sized to match the EDM values. Voxels enclosed by the spheres are assigned the radius value of the largest sphere. In other words, each solid voxel is assigned the radial value of the largest sphere that both fits within the solid space boundary and includes the assigned voxel. The 3D labelled sphere distribution output from the LTM data scan can be treated as a stack of two-dimensional images in the height-direction (or Z-direction) and used to estimate the change in sphere diameter from slice to slice as a function of fibrous structure depth. The particle thickness is treated as a 3D dataset and an average value can be assessed for the whole or parts of the subvolume. The calculations and measurements were done using AVIZO Lite (9.2.0) from Thermo Fisher Scientific and MATLAB (R2018b) from Mathworks.

Also, to characterize particle distribution, the thresholded smaller particle dataset can be used to identify connected or separate components. For instance, a connected object is a set of adjacent voxels with intensity values lying inside the selected threshold range. Once the regiosn are identified, statistical quantities for the regions are outputted such as individual particle Volumes (Number of voxels times size of a single voxel) and CenterX, CenterY, Center: [X, Y, Z] correspond to coordinate of the particle's center. Data processing in Matlab can provide detailed histograms of distributions as a function of depth.

On the other hand, the thresholded smaller dataset can be used to generate Iso-surface in Avizo without smoothing. An isosurface is a 3D analog to an isocontour that is rendered for a mesh of polygons. The Surface Area to Contained Volume function in Avizo adds up the area of all patche's triangles, and also assessed the volume surrounded by the triangles, and outputs the data in an excel sheet.

Particle Size Distribution Test Method: The particle size distribution test is conducted to determine characteristic sizes of solid additives, for example particles. It is conducted using ASTM D 502-89, "Standard Test Method for Particle Size of Soaps and Other Detergents", approved May 26, 1989, with a further specification for sieve sizes and sieve time used in the analysis. Following section 7, "Procedure using machine-sieving method," a nest of clean dry sieves containing U.S. Standard (ASTM E 11) sieves #4 (4.75 mm), #6 (3.35 mm), #8 (2.36 mm), #12 (1.7 mm), #16 (1.18 mm), #20 (850 micrometer), #30 (600 micrometer), #40 (425 micrometer), #50 (300 micrometer), #70 (212 micrometer), #100 (150 micrometer), #170 (90 micrometer), #325 (44 micrometer) and pan is required to cover the range of particle sizes referenced herein. The prescribed Machine-Sieving Method is used with the above sieve nest. A suitable sieve-shaking machine can be obtained from W. S. Tyler Company, Ohio, U.S.A. The sieve-shaking test sample is approximately 100 grams and is shaken for 5 minutes.

The data are plotted on a semi-log plot with the micrometer size opening of each sieve plotted on the logarithmic abscissa and the cumulative mass percent finer (CMPF) is plotted on the linear ordinate. An example of the above data representation is given in ISO 9276-1:1998, "Representation of results of particle size analysis—Part 1: Graphical Representation", FIG. A.4. A characteristic particle size (Dx, x=10, 50, 90), for the purpose of this invention, is defined as the abscissa value at the point where the cumulative mass percent is equal to x percent, and is calculated by a straight line interpolation between the data points directly above (a) and below (b) the x value using the following equation:

$$Dx = 10^{\wedge}\left[\text{Log}(Da) - (\text{Log}(Da) - \text{Log}(Db)) * (Qa - x\ \%)/(Qa - Qb)\right]$$

where Log is the base 10 logarithm, Qa and Qb are the cumulative mass percentile values of the measured data immediately above and below the $x^{th}$ percentile, respectively; and Da and Db are the micrometer sieve size values corresponding to these data.

Example Data and Calculations

| sieve size (micrometer) | weight on sieve (g) | cumulative mass % finer (CMPF) |
|---|---|---|
| 1700 | 0 | 100% |
| 1180 | 0.68 | 99.3% |
| 850 | 10.40 | 89.0% |
| 600 | 28.73 | 60.3% |
| 425 | 27.97 | 32.4% |
| 300 | 17.20 | 15.2% |
| 212 | 8.42 | 6.8% |
| 150 | 4.00 | 2.8% |
| Pan | 2.84 | 0.0% |

For D10 (x=10), the micrometer screen size where CMPF is immediately above 10% (Da) is 300 micrometer, the screen below (Db) is 212 micrometer. The cumulative mass immediately above 10% (Qa) is 15.2%, below (Qb) is 6.8%. D10=10^[Log(300)−(Log(300)−Log(212))*(15.2%−10%)/(15.2%−6.8%)]=242 micrometer.

For D90 (x=90), the micrometer screen size where CMPF is immediately above 90% (Da) is 1180 micrometer, the screen below (Db) is 850 micrometer. The cumulative mass immediately above 90% (Qa) is 99.3%, below (Qb) is 89.0%. D90=10^[Log(1180)−(Log(1180)−Log(850))* (99.3%−90%)/(99.3%−89.0%)]=878 micrometer.

For D50 (x=50), the micrometer screen size where CMPF is immediately above 50% (Da) is 600 micrometer, the screen below (Db) is 425 micrometer. The cumulative mass immediately above 50% (Qa) is 60.3%, below (Qb) is 32.4%. D50=10^[Log(600)−(Log(600)−Log(425))* (60.3%−50%)/(60.3%−32.4%)]=528 micrometer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for forming a composite fluid stream comprising:
    mixing a stream comprising a plurality of fibrous elements with a stream of particles exiting a nozzle in a machine direction having a range of particle sizes;
    wherein the stream of particles exhibits an injection angle that is substantially non-vertical towards a collection belt and oriented in the machine direction of the collection belt;
    wherein the stream of particles has a substantially lower air velocity than the stream comprising a plurality of fibrous elements, resulting in a bent trajectory of particles towards the collection belt;
    wherein the bent trajectory of larger particles in the stream of particles exhibits a substantially larger turning radius towards the collection belt compared to smaller particles, resulting in the larger particles being embedded in the fibrous elements at a further distance in the machine direction versus the nozzle, and the bent trajectory of the smaller particles of the stream of particles exhibits a substantially smaller turning radius towards the collection belt, resulting in the smaller particles being embedded in the fibrous elements at a shorter distance in the machine direction versus the nozzle.

2. The process according to claim 1, wherein the stream comprising a plurality of fibrous elements is additionally mixed with a second stream comprising a plurality of filaments.

3. The process according to claim 2, wherein the stream comprising a plurality of fibrous elements and the second stream comprising a plurality of filaments are commingled.

4. The process according to claim 1, wherein the stream of particles exhibits a range of Stokes Numbers.

5. The process according to claim 1, wherein the stream of particles comprises absorbent material particles.

6. The process according to claim 5, wherein the absorbent material particles comprise super absorbent polymer particles.

7. The process according to claim 1, wherein the stream of particles exits the nozzle in the same direction as the movement of the collection belt.

8. A fibrous structure produced by the process of claim 7, wherein larger particles are present at the top side of the fibrous structure.

9. The process according to claim 1, wherein the stream of particles exits the nozzle in the opposite direction as the movement of the collection belt.

10. A fibrous structure produced by the process of claim 9, wherein larger particles are present at the bottom side of the fibrous structure.

11. The process according to claim 1, wherein the stream of particles exits the nozzle in the same direction as the movement of the collection belt and a second stream of particles having a range of particle sizes exit a nozzle in a machine direction opposite the direction of the movement of the collection belt;
    wherein the second stream of particles exhibits an injection angle that is substantially non-vertical towards a collection belt and substantially oriented in the machine direction of the collection belt, a substantially lower air velocity than the stream comprising a plurality of fibrous elements, resulting in a bent trajectory of particles towards the collection belt;
    wherein the bent trajectory of larger particles of the stream of particles exhibits a substantially larger turning radius towards the collection belt as compared to smaller particles, resulting in the larger particles being embedded in the fibrous elements at a further distance in the machine direction versus the nozzle, and the bent trajectory of the smaller particles of the stream of particles exhibits a substantially smaller turning radius towards the collection belt, resulting in the smaller particles being embedded in the fibrous elements at a shorter distance in the machine direction versus the nozzle.

12. A fibrous structure produced by the process of claim 11, wherein larger particles are present at the top and bottom of the fibrous structure, and smaller particles are present in the center of the fibrous structure.

13. The process according to claim 1, further comprising a second process for forming a composite fluid stream comprising:
    mixing a stream comprising a plurality of fibrous elements with a stream of particles exiting a nozzle in a machine direction having a range of particle sizes;
    wherein the stream of particles exhibits an injection angle that is substantially non-vertical towards a collection belt and substantially oriented in the machine direction of the collection belt, a substantially lower air velocity than the stream comprising a plurality of fibrous elements, resulting in a bent trajectory of particles towards the collection belt;
    wherein the bent trajectory of larger particles of the stream of particles exhibits a substantially larger turning radius towards the collection belt as compared to smaller particles, resulting in the larger particles being embedded in the fibrous elements at a further distance in the machine direction versus the nozzle, and the bent trajectory of the smaller particles of the stream of particles exhibits a substantially smaller turning radius towards the collection belt, resulting in the smaller particles being embedded in the fibrous elements at a shorter distance in the machine direction versus the nozzle.

14. The process according to claim 13, wherein the second process occurs after the process of claim 1 in the machine direction.

15. The process according to claim 1, wherein the fluid stream is applied to a scrim layer present on the collection belt.

16. The process according to claim 15, wherein a scrim layer is applied to the fluid stream present on the collection belt.

17. The process according to claim 1, wherein a scrim layer is applied to the fluid stream present on the collection belt.

* * * * *